(12) United States Patent
Tomigahara et al.

(10) Patent No.: US 8,524,729 B2
(45) Date of Patent: Sep. 3, 2013

(54) CINNAMOYL DERIVATIVES AND USE THEREOF

(75) Inventors: Yoshitaka Tomigahara, Toyonaka (JP); Kiyoshi Higashi, Osaka (JP); Junya Takahashi, Kawabe-gun (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1968 days.

(21) Appl. No.: 10/572,705

(22) PCT Filed: Sep. 16, 2004

(86) PCT No.: PCT/JP2004/013989
§ 371 (c)(1),
(2), (4) Date: Mar. 17, 2006

(87) PCT Pub. No.: WO2005/028441
PCT Pub. Date: Mar. 31, 2005

(65) Prior Publication Data
US 2007/0123521 A1    May 31, 2007

(30) Foreign Application Priority Data

| Sep. 17, 2003 | (JP) | 2003-324150 |
| Sep. 17, 2003 | (JP) | 2003-324155 |
| Sep. 17, 2003 | (JP) | 2003-324156 |
| Sep. 17, 2003 | (JP) | 2003-324157 |

(51) Int. Cl.
*A61K 31/435* (2006.01)
*C07D 213/69* (2006.01)
*C07D 213/70* (2006.01)

(52) U.S. Cl.
USPC .................................. 514/277; 546/296

(58) Field of Classification Search
USPC ........................... 514/277; 546/296
See application file for complete search history.

(56) References Cited

U.S. PATENT DOCUMENTS

| 4,017,633 A | 4/1977 | Willis |
| 5,268,378 A | 12/1993 | Baker et al. |
| 6,215,016 B1 | 4/2001 | Kawai et al. |
| 2002/0010169 A1 | 1/2002 | Drewe et al. |
| 2004/0259877 A1 | 12/2004 | Muto et al. |
| 2006/0019958 A1 | 1/2006 | Muto et al. |
| 2006/0100257 A1 | 5/2006 | Muto et al. |
| 2006/0111409 A1 | 5/2006 | Muto et al. |
| 2006/0122243 A1 | 6/2006 | Muto et al. |
| 2006/0211680 A1 | 9/2006 | Tomigahara et al. |
| 2007/0265228 A1 | 11/2007 | Tomigahara |
| 2009/0143368 A1 | 6/2009 | Shiraki et al. |
| 2009/0275650 A1 | 11/2009 | Reddy et al. |

FOREIGN PATENT DOCUMENTS

| JP | 41-1412 | 2/1966 |
| JP | 50-46666 | 4/1975 |
| JP | 9-227547 | 9/1997 |
| JP | 2001-89412 | 4/2001 |
| JP | 2002-371078 | 12/2002 |
| JP | 2004-123620 | 4/2004 |
| JP | 2004-123621 | 4/2004 |
| SU | 189308 | 10/1965 |
| WO | 89/07939 | 9/1989 |
| WO | 92/18483 | 10/1992 |
| WO | 96/22021 | 7/1996 |
| WO | 97/35565 | 10/1997 |
| WO | 00/20371 | 4/2000 |
| WO | 00/61576 | 10/2000 |
| WO | 01/79187 | 10/2001 |
| WO | 02/49632 | 6/2002 |
| WO | 03/080592 | 10/2003 |
| WO | 03/103647 | 12/2003 |
| WO | 03/103648 | 12/2003 |
| WO | 03/103658 | 12/2003 |
| WO | 03/103665 | 12/2003 |

OTHER PUBLICATIONS

Schubert et al., European Journal of Pharmaceutics and Biopharmaceutics, 55 (2003) 125-131.*
Database CAS Online on STN, Chem. Abstr., Accession No. 1968:39432, Vul'fson et al., Khimiya Geterotsiklicheskikh Soedinenii (1967), (4), 682-6.,abstract only.*
Canadian Office Action issued Apr. 11, 2011 in corresponding Canadian Application No. 2,539,162.
International Search Report mailed Jan. 11, 2005 in International (PCT) Application No. PCT/JP2004/013989.
V. K. Mahesh et al., "Condensation Products of Dehydracetic Acid with Aromatic Aldehydes & Pyrazolines Derived from Them", Indian Journal of Chemistry, vol. 12, pp. 956-957 (1974).
M. Abass, "Chemistry of Substituted Quinolinones. Part II Synthesis of Novel 4-Pyrazolylquinolinone Derivatives", Synthetic Communications, 30(15), pp. 2735-2757 (2000).
S. S. Ibrahim et al., "New Quinolones and Naphthyridinones Bearing Heterocyclic Rings", Chem. Papers, 53(1), pp. 53-64 (1999).
S. S. Ibrahim et al., "Synthesis of New 3-Acryloyl-1,2-dihydro-4-hydroxy-1-methyl-2-oxoquinoline Derivatives and their Behaviour towards Some Nucleophiles", Chem. Papers 51(1), pp. 33-42 (1997).
Alekseyev et al., Journal of Applied Spectroscopy, V. 61, N 3-4, pp. 234-236 (1994), with English Abstract.
E. A. Mohamed et al., "Synthesis of 3-Heteroaryl-4-Hydroxybenzocarbostyrils", Journal of Indian Chem. Soc., vol. 69, pp. 82-84 (1992).

(Continued)

Primary Examiner — Rebecca Anderson
(74) Attorney, Agent, or Firm — Wenderoth, Lind & Ponack, L.L.P.

(57) ABSTRACT

The present invention relates to a cinnamoyl compound represented by the formula (I):

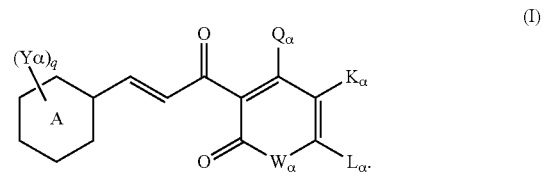

(I)

6 Claims, No Drawings

(56) References Cited

OTHER PUBLICATIONS

Ali A. Z. El Fayoumi, "Thermal Degradation of Epoxidized Polydienes III. Thermal Behaviour of Some Cross-linked Epoxidized Polydienes", Journal of Thermal Analysis, vol. 23, pp. 135-141 (1982).

A. A. Z. El Fayoumi et al., "3-Substituted-4-Hydroxycarbostyrils as Curing Agents for Epoxidized Polydienes", Egypt. J. Chem. 23, No. 3, pp. 191-200 (1980).

A. A. Sayed et al., "The Behaviour of some 3-Substituted 4-Hydroxy-1-alkyl (or phenyl) Carbostyrils towards Amines and Hydrazines", Egypt. J. Chem., vol. 19, No. 5, pp. 811-826 (1976).

H. H. Zoorob et al., "Reactivity of 3-Cinnamoyl-1-Phenyl-2,4 (1H,3H)—Quinoline-Dione Towards Oxidation and Oximation Reactions. Formation of Fused Heterocyclic Quinolines", Egypt. J. Chem., vol. 29, No. 3, pp. 325-331 (1986).

Katsuhide Matoba et al., "Synthetic Studies of Azaflavonoids. II. Synthesis of 6-Azaflavonoids", Chem. Pharm. Bull., 27(1), pp. 242-246 (1979).

Okatov et al., Journal of Applied Spectroscopy, vol. 7(4), pp. 638-643 (1967), with English Abstract.

Ali A. Z. El Fayoumi, "Thermal Behavior of Some Crosslinked Epoxidised Polydienes", The Muslim Scientist, pp. 489-498 (1981).

K. Sucheta et al., "Synthesis of Novel 1,5-Benzothiazepines Containing 2H(1)-Quinolin-2-One Heterocycle", Heterocyclic Communications, No. 020413, pp. 569-572 (2002).

Y. Rachedi et al., "Synthesis of 4-Hydroxy 6-Methyl 3-β-Arylpropionyl 2-Pyrones by Selective Catalytic Hydrogenation of 3-Cinnamoyl 4-Hydroxy 6-Methyl 2-Pyrones", Synthetic Communications, 19(20), pp. 3437-3442 (1989).

Tyunosin Ukita et al., "In vitro Screening of Tricarbonylmethane and Related Compounds for their Anti-tumor Effect by Cylinder Agar Plate (CAP) Method", Chemical and Pharmaceutical Bulletin, vol. 8, pp. 1016-1020 (1960).

G. V. Kalechits et al., "Synthesis and Properties of 3-Cynnamoyl-4-hydroxy-2-quinolone", Russian Journal of General Chemistry, vol. 71, No. 8, pp. 1257-1260 (2001).

Canadian Office Action issued Jan. 16, 2012 in corresponding Canadian Application No. 2,539,162.

Matoba et al., "Synthetic Studies of Azaflavonoids. II. Synthesis of 6-Azaflavonoids", Chemical & Pharmaceutical Bulletin, vol. 27, Issue 1, 1979, pp. 242-246.

European Office Action issued Mar. 11, 2013 in corresponding European Patent Application 04 773 379.5.

Database Caplus, Database accession No. 1968:109814 (2013).
Database Caplus, Database accession No. 1968:39432 (2013).

* cited by examiner

CINNAMOYL DERIVATIVES AND USE THEREOF

This application is a U.S. national stage of International Application No. PCT/JP2004/013989 filed Sep. 16, 2004.

TECHNICAL FIELD

The present invention relates to cinnamoyl derivatives use thereof.

BACKGROUND ART

In diseases and disorders such as hepatic cirrhosis, interstitial pulmonary disease, chronic renal failure (or disease resulting in chronic renal failure), hyperplasia scar after inflammation, postoperative scars or burn scars, scleroderma, arteriosclerosis, hypertension and the like, excessive accumulation of an extracellular matrix, a representative of which is collagen, causes fibrosis and sclerosis of tissues, resulting in decreased functions, cicatrization and the like in the organs or tissues. Such excessive accumulation of an extracellular matrix is induced by increased production of collagen due to a breakdown of balance between biosynthesis and degradation of collagen and the like. In fact, it has been observed that expression of a collagen gene, in particular, a Type I collagen gene has been increased in a fibrotic tissue [e.g. J. Invest. Dermatol., 94, 365, (1990) and Proc. Natl. Acad. Sci. USA, 88, 6642, (1991)]. It has been also observed that the amount of TGF-β, which is a cytokine, has been increased in a fibrotic tissue [e.g. J. Invest. Dermatol., 94, 365, (1990) and Proc. Natl. Acad. Sci. USA, 88, 6642, (1991)]. It has been shown that TGF-β has increased expression of a Type I collagen gene and been involved in increased production of collagen and, consequently, fibrosis of a tissue [e.g. Lab. Invest., 63, 171, (1990) and J. Invest. Dermatol., 94, 365, (1990)]. It has been also shown that by administering an anti-TGF-β antibody or a soluble anti-TGF-β receptor to a model animal of tissue fibrosis, improvement of tissue fibrosis has been achieved and thereby the tissue function has been also improved [e.g. Diabetes, 45, 522-530, (1996), Proc. Natl. Acad. Sci. USA, 96, 12719-12724, (1999) and Proc. Natl. Acad. Sci. USA, 97, 8015-8020, (2000)]. It has been also known that by administering a compound which suppressively acts on intracellular signal transduction via TGF-β, improvement in fibrosis of a tissue has been achieved and thereby the tissue function has been also improved [e.g. Autoimmunity, 35, 277-282, (2002), J. Hepatol., 37, 331-339, (2002) and Life Sci., 71, 1559-1606, (2002)].

Thus, there is a need for development and provision of a drug which improves fibrosis of a tissue by decreasing expression of a Type I collagen gene in the tissue to reduce accumulation of collagen (i.e. a collagen accumulation-suppressing agent and a fibrosing disease-treating agent).

DISCLOSURE OF THE INVENTION

Under these circumstances, the present inventors have intensively studied and, as a result, found out that compounds represented by the following formulas (I) to (V), (VII), (VIII), (X), (XI), (XIII), and (XV) to (XIV) has the ability to suppress transcription of I type collagen gene. Thus, the present invention has been completed.

That is, the present invention provides:

1. A I type collagen gene transcription suppressing composition, which comprises a cinnamoyl compound represented by the formula (I):

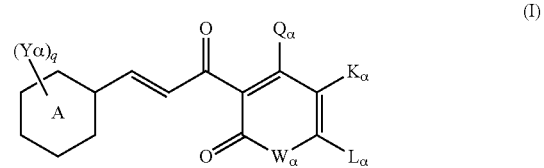

(I)

[wherein

I. A represents a benzene ring or a pyridine ring, in $(Y_\alpha)_q$, $Y_\alpha$ is a substituent on a carbon atom, and represents a substituent of the following $X_0$ group or $Y_0$ group, q represents 0, 1, 2, 3, 4 or 5, when q is 2 or more, $Y_\alpha$'s are the same or different and, when q is 2 or more, the adjacent two same or different $Y_\alpha$'s constitute a group of a $Z_0$ group, and may be fused with an A ring;

(1) a $X_0$ group:

a $M_a$-group [$M_a$ represents a $R_b$-group ($R_b$ represents a C1-C10 alkyl group optionally substituted with a halogen atom), a halogen atom, a nitro group, a cyano group, a hydroxy group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, $R_d$ represents a single bond or a C1-C10 alkylene group), a $HOR_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_e$O—CO—$R_d$-group ($R_e$ and $R_d$ are as defined above), a HO—CO—CH=CH-group, a $R_eR_e'$N—$R_d$-group ($R_e$ and $R_e'$ are the same or different, $R_e$ is as defined above, $R_e'$ has the same meaning as that of $R_e$, and $R_d$ is as defined above), a $R_bO$—CO—$NR_e'$—$R_d$-group ($R_b$, $R_e'$ and $R_d$ are as defined above), a $R_bO$—CO—$N(R_e)$—$R_d$-group ($R_b$, $R_e$ and $R_d$ are as defined above), a $R_eR_e'$N—CO—$R_d$-group ($R_e$, $R_e'$ and $R_d$ are as defined above), a $R_eR_e'$N—CO—$NR_e''$—$R_d$-group ($R_e$, $R_e'$ and $R_e''$ are the same or different, $R_e$ and $R_e'$ are as defined above, $R_e''$ has the same meaning as that of $R_e$, and $R_d$ is as defined above), a $R_eR_e'$N—C(=N$R_e''$)—$R_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—$SO_2$—$NR_e$—$R_d$-group ($R_b$, $R_e$ and $R_d$ are as defined above), a $R_eR_e'$N—$SO_2$—$R_d$-group ($R_e$, $R_e'$ and $R_d$ are as defined above), a C2-C10 alkenyl group or a C2-C10 alkynyl group.];

(2) a $Y_0$ group:

a $M_{b0}$-$R_d$-group [$M_{b0}$ represents a $M_{c0}$-group {$M_{c0}$ represents a $M_{d0}$-$R_d'$-group {$M_{d0}$ represents a 6 to 10-membered aryl group optionally substituted with a $M_a$-group ($M_a$ is as defined above), or 5 to 10-membered heteroaryl group optionally substituted with $M_a$ group ($M_a$ is as defined above), or a 3 to 10-membered hydrocarbon ring or heterocycle optionally substituted with a $M_a$-group ($M_a$ is defined above) and optionally containing an unsaturated bond, or

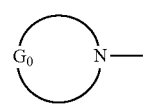

(b₀)

a ($b_0$)-group (in ($b_0$), $G_0$ constitutes a saturated or unsaturated non-aromatic 5 to 14-membered hydrocarbon ring or heterocycle optionally having a substituent),

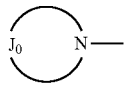

($c_0$)

a ($c_0$)-group (in ($C_0$), $J_0$ may contain a nitrogen atom, and constitutes an aromatic 5 to 7-membered ring),

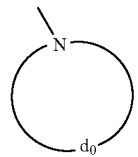

($d_0$)

a ($d_0$)-group {$d_0$ represents a 5 to 12-membered hydrocarbon ring substituted with carbonyl group or a thiocarbonyl group and, further, optionally substituted with an oxy group, a thio group, a —$NR_1$-group {$R_1$ represents a hydrogen atom, or a C1-C10 alkyl group, or a C2-C10 alkyl group substituted with halogen atom or a $R_2$—$B_1$-group ($R_2$ represents a C1-C10 alkyl group, a C3-C10 alkenyl group or a C3-C10 alkenyl group, and $B_1$ represents an oxy group, a thio group, a sulfinyl group or a sulfonyl group), or a C3-C10 alkenyl group, or a C3-C10 alkenyl group}, a sulfinyl group, or a sulfonyl group} or

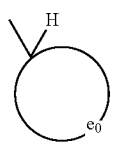

($e_0$)

an ($e_0$)-group {$e_0$ constitutes a 5 to 12-membered hydrocarbon ring optionally substituted with a carbonyl group, a thiocarbonyl group, an oxy group, a thio group, a —$NR_1$-group ($R_1$ is as defined above), a sulfinyl group or a sulfonyl group}, $R_d'$ is the same as or different from $R_d$, and has the same meaning as that of $R_d$}}, a $M_{c0}$-$B_a$-group ($M_{c0}$ and $B_a$ are as defined above), a $M_{c0}$-CO-group ($M_{c0}$ is as defined above), a $M_{c0}$-CO—O group ($M_{c0}$ is as defined above), a $M_{c0}$O—CO-group ($M_{c0}$ is as defined above), a $M_{c0}R_eN$-group ($M_{c0}$ and $R_e$ are as defined above), a $M_{c0}$-CO—$NR_e$-group ($M_{c0}$ and $R_e$ are as defined above), a $M_{c0}$O—CO—$NR_e$-group ($M_{c0}$ and $R_e$ are as defined above), a $M_{c0}R_eN$—CO-group ($M_{c0}$ and $R_e$ are as defined above), a $M_{c0}R_eN$—CO—$NR_e'$-group ($M_{c0}$, $R_e$ and $R_e'$ are as defined above), a $M_{c0}R_eN$—C(=$NR_e'$)—$NR_e''$-group ($M_{c0}$, $R_e$, $R_e'$ and $R_e''$ are as defined above), a $M_{c0}$-$SO_2$—$NR_e$-group ($M_{c0}$ and $R_e$ are as defined above) or $M_{c0}R_eN$—$SO_2$-group ($M_{c0}$ and $R_e$ are as defined above), and $R_d$ is as defined above.];

(3) a $Z_0$ group: a group which is a 5 to 12-membered hydrocarbon ring or heterocycle having a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group or a sulfonyl group, is an aromatic or non-aromatic monocyclic or fused ring, and is fused with an A ring;

II. $Q_\alpha$ represents an optionally substituted hydroxyl group, or an optionally substituted amino group;

III. $W_\alpha$ represents an oxygen atom or a-$NT_\alpha$-group ($T_\alpha$ represents a hydrogen atom, or a substituent on a nitrogen atom.);

IV. $K_\alpha$ and $L_\alpha$ are the same or different, and represent a hydrogen atom, or a substituent on a carbon atom, or $K_\alpha$ and $L_\alpha$ may form a C1-C10 alkylene group optionally having a substituent or a C1-C10 alkenylene group optionally having a substituent; provided that when an A ring is a benzene ring, $W_\alpha$ is an oxygen atom, $L_\alpha$ is a methyl group, $K_\alpha$ is a hydrogen atom, and $Q_\alpha$ is a C1-C4 alkoxy group, a C3-C4 alkenyloxy group or a C3-C4 alkynyloxy group, then q is not 0 and, when an A ring is a benzene ring, $W_\alpha$ is an oxygen atom, $L_\alpha$ is a methyl group, $K_\alpha$ is a hydrogen atom, and $Q_\alpha$ is a C1-C4 alkoxy group, a C3-C4 alkenyloxy group or a C3-C4 alkynyloxy group, then q is 1, and $Y_\alpha$ is not a halogen atom, or a C1-C4 alkyl group optionally substituted with a halogen atom or a C1-C4 alkoxy group, or a nitro group, or a C1-C4 alkoxy group, or a RB-group (R represents a C1-C4 haloalkyl group, and B represents an oxy group or a thio group) and, when A is a benzene ring, $W_\alpha$ is an oxygen atom, $L_\alpha$ and $K_\alpha$ form a 1,3-butadienylene group, and $Q_\alpha$ is a methoxy group, then q is 1, and $Y_\alpha$ is not a methoxy group or an ethoxy group and, when A is a benzene ring, $W_\alpha$ is an oxygen atom, $L_\alpha$ and $K_\alpha$ form a 1,3-butadienylene group, and $Q_\alpha$ is a hydroxyl group, then q is 1, and $Y_\alpha$ is not an ethoxy group; and the "as defined above" in the same symbol between a plurality of substituents indicates that the plurality of substituents independently represent the same meaning as that described above and, between the plurality of substituents, a selection range of selected substituents is the same, while the selected substituents may be the same or the different as far as they are selected in the range]; and an inert carrier;

2. A I type collagen gene transcription suppressing composition, which comprises a cinnamoyl compound represented by the formula (II):

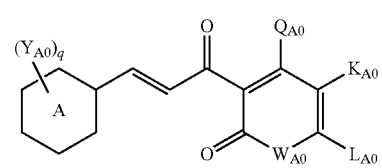

(II)

[wherein
I. A represents a benzene ring or pyridine ring;
II. In ($Y_{A0}$)q, $Y_{A0}$ is a substituent on a carbon atom, and represents a substituent of the following $X_0$ group and $Y_0$ group, q represents 0, 1, 2, 3, 4 or 5, when q is 2 or more, $Y_{A0}$'s are the same or different and, when q is 2 or more, the adjacent two same or different $Y_{A0}$'s constitute a group of a $Z_0$ group, and may be fused with an A ring;
(1) a $X_0$ group:
a $M_a$-group [$M_a$ represents a $R_b$ group ($R_b$ represents a C1-C10 alkyl group optionally substituted with a halogen atom), a halogen atom, a nitro group, a cyano group, a hydroxyl group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a $HOR_d$-group ($R_d$ is as defined above), a $R_e$—CO—$R_d$-group ($R_e$ represents hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_eO$—CO—$R_d$-group ($R_e$ and $R_d$ are as defined above), a HO—CO—CH=CH-group, a $R_eR_e'N$—$R_d$-group ($R_e$ and $R_e'$ are the same or different, $R_e'$ has the same meaning as that of $R_e$ and $R_d$ is as defined above), a $R_e$—CO—$NR_e'$—$R_d$-group ($R_e$, $R_e'$ and $R_d$ are as defined above), a $R_bC$—CO—$N(R_e)$—$R_d$-group ($R_b$, $R_e$ and $R_d$ are as defined above), a $R_eR_e'N$—CO—$R_d$-group ($R_e$, $R_e'$ and $R_d$ are as defined above), a $R_eR_e'N$—CO—$NR_e''$—$R_d$-group ($R_e$, $R_e'$ and $R_e''$ are the same or different, $R_e$ and $R_e'$ are as defined above, $R_e''$ has the same meaning as that of $R_e$ and $R_d$ is as defined above), a $R_eR_e'N$—C(=$NR_e''$)—$NR_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—$SO_2$—$NR_e$—$R_d$-group ($R_b$, $R_e$ and $R_d$ are as defined above), a $R_eR_e'N$—$SO_2$—$R_d$-group ($R_e$, $R_e'$ and $R_d$ are as defined above), a C2-C10 alkenyl group or a C2-C10 alkynyl group.];

(2) a $Y_0$ group:

a $M_{b0}$-$R_d$-group [$M_{b0}$ represents a $M_{c0}$ group {$M_{c0}$ represents a $M_{d0}$-$R_d'$-group {$M_{d0}$ represents a 6 to 10-membered aryl group optionally substituted with a $M_a$-group ($M_a$ is as defined above), or a 5 to 10-membered heteroaryl group optionally substituted with a $M_a$-group ($M_a$ is as defined above), a 3 to 10-membered hydrocarbon ring or heterocycle optionally substituted with a $M_a$-group ($M_a$ is as defined above) and optionally containing an unsaturated bond, or

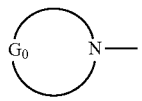

($b_0$)

a ($b_0$)-group (in ($b_0$), $G_0$ constitutes a saturated or unsaturated non-aromatic 5 to 14-membered hydrocarbon ring or heterocycle optionally having a substituent),

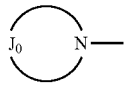

($c_0$)

a ($c_0$)-group (in ($c_0$), $J_0$ may contain a nitrogen atom, and constitutes an aromatic 5 to 7-membered ring),

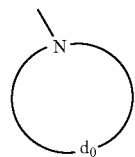

($d_0$)

a ($d_0$)-group {$d_0$ constitutes a 5 to 12-membered hydrocarbon ring substituted with a carbonyl group or a thiocarbonyl group and, further, optionally substituted with an oxy group, a thio group, a —$NR_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or sulfonyl group), or a C3-C10 alkenyl group, or a C3-C10 alkynyl group}, a sulfinyl group or a sulfonyl group} or

($e_0$)

an ($e_0$)-group {$e_0$ represents a 5 to 12-membered hydrocarbon ring optionally substituted with a carbonyl group, a thiocarbonyl group, an oxy group, a thio group, a —$NR_1$-group ($R_1$ is as defined above), a sulfinyl group or a sulfonyl group}, $R_d'$ is the same as or different from $R_d$, and has the same meaning as that of $R_d$}}, a $M_{c0}$-$B_a$-group ($M_{c0}$ and $B_a$ are as defined above), a $M_{c0}$-CO-group ($M_{c0}$ is as defined above), a $M_{c0}$-CO—O-group ($M_{c0}$ is as defined above), a $M_{c0}$O—CO-group ($M_{c0}$ is as defined above), a $M_{c0}R_eN$-group ($M_{c0}$ and $R_e$ are as defined above), a $M_{c0}$-CO—$NR_e$-group ($M_{c0}$ and $R_e$ are as defined above), a $M_{c0}$O—CO—$NR_e$-group ($M_{c0}$ and $R_e$ are as defined above), a $M_{c0}R_eN$—CO-group ($M_{c0}$ and $R_e$ are as defined above), a $M_{c0}R_eN$—CO—$NR_e'$-group ($M_{c0}$, $R_e$ and $R_e'$ are as defined above), a $M_{c0}R_eN$—C(=$NR_e'$)—$NR_e''$-group ($M_{c0}$, $R_e$, $R_e'$ and $R_e''$ are as defined above), a $M_{c0}$-$SO_2$—$NR_e$-group ($M_{c0}$ and $R_e$ are as defined above) or $M_{c0}R_eN$—$SO_2$-group ($M_{c0}$ and $R_e$ are as defined above), and $R_d$ is as defined above.];

(3) a $Z_0$ group: a group which is a 5 to 12-membered hydrocarbon ring or heterocycle ring optionally having a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group or a sulfonyl group, is an aromatic or non-aromatic monocyclic or fused ring, and is fused with an A ring;

III. $Q_{A0}$ represents a hydroxyl group, a ($b_0$)-group (($b_0$) is as defined above), an $A_9$-$B_6$—$B_c$-group [$A_9$ represents a substituent of the following $A_7$ group or $A_8$ group, $B_6$ represents a carbonyl group or a thiocarbonyl group, and $B_c$ represents an oxy group or a —$N((O)_mR_1)$-group {m represents 0 or 1, and $R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group}, provided that when $A_9$ is a hydrogen atom, then $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1R_1'N$—$SO_2$—$B_c$-group ($R_1$ is as defined above, $R_1'$ and $R_1$ are the same or different, and has the same meaning as that of $R_1$, and $B_c$ is as defined above), a ($b_0$)—$SO_2$—$B_c$-group (($b_0$) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_{c0}$-$B_3$—$B_c$-group ($B_3$ represents a carbonyl group, a thiocarbonyl group or a sulfonyl group, and $M_{c0}$ and $B_c$ are as defined above) or a $M_{c0}$-$B_c$-group ($M_{c0}$ and $B_c$ are as defined above);

(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$-group, and $R_4$ is as defined above}, a $(b_0)$-$R_4$-group ($(b_0)$ is as defined above, and $R_4$ is as defined above), a $(c_0)$-$R_4$-group ($(c_0)$ is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a $(b_0)$-group ($(b_0)$ is as defined above), a $(c_0)$-group ($(c_0)$ is as defined above) or a $R_1R_1'N$-group ($R_1$ and $R_1'$ are as defined above), and $R_4$ is as defined above} or an $A_2$-CO—$R_4$-group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$-group ($D_4$ and $R_4'$ are as defined above), a $D_1$-$R_4'$-group ($D_1$ and $R_4'$ are as defined above), a $(b_0)$-$R_4'$-group ($(b_0)$ and $R_4'$ are as defined above), a $(c_0)$-$R_4'$-group ($(c_0)$ and $R_4'$ are as defined above), a $D_2$-$R_4$-group ($D_2$ and $R_4$ are as defined above), a $D_3$-$R_4'$-group ($D_3$ and $R_4'$ are as defined above) or an $A_2$-CO—$R_4$-group ($A_2$ and $R_4$ are as defined above);

(4) an $A_8'$ group: a C1-C10 alkyl group or C2-C10 haloalkyl group;

(5) an $A_7''$ group: a C2-C10 alkenyl group, a C3-C10 alkenyl group substituted with a halogen atom, a C3-C10 alkynyl group optionally substituted with a halogen atom, a $R_2$—$B_1$—$R_4'$-group ($R_2$, $B_1$ and $R_4'$ are as defined above), a $D_4$-$R_4'$-group ($D_4$ and $R_4'$ are as defined above), a $D_5$-$R_4'$-group ($D_5$ and $R_4$ are as defined above), a $D_1$-$R_4'$-group ($D_1$ and $R_4'$ are as defined above), $(b_0)$-$R_4'$-group ($(b_0)$ and $R_4'$ are as defined above), a $(c_0)$-$R_4'$-group ($(c_0)$ and $R_4'$ are as defined above), a $D_2$-$R_4$-group ($D_2$ and $R_4$ are as defined above), a $NO_2$-$R_4$-group ($R_4$ is as defined above) or an $A_2$-CO—$R_4$-group ($A_2$ and $R_4$ are as defined above);

(i) a $D_4$-group: a hydroxy group or an $A_1$-O-group [$A_1$ represents a $R_3$—$(CHR_0)_m$—$(B_2$—$B_3)_{m'}$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —$N((O)_nR_1')$-group ($R_1'$ is as defined above, and n represents 0 or 1), $B_3$ is as defined above, m' represents 0 or 1 and, when $B_3$ is a sulfonyl group, then m is 0, and $R_3$ is not a hydrogen atom}];

(ii) a $D_5$ group: an O=C($R_3$)-group ($R_3$ is as defined above), an $A_1$-(O)—N=C($R_3$)-group ($A_1$, n and $R_3$ are as defined above), a $R_1$—$B_0$—CO—$R_4$—$(O)_n$—N=C($R_3$)-group [$R_1$, $R_4$, n and $R_3$ are as defined above, and $B_0$ represents an oxy group, a thio group or a —$N((O)_mR_1')$-group ($R_1'$ and m are as defined above)], a $D_2$-$R_4$—$(O)_n$—N=C($R_3$)-group ($D_2$, $R_4$, n and $R_3$ are as defined above) or a $R_1A_1N$—N=C($R_3$)-group ($R_1$, $A_1$ and $R_3$ are as defined above);

(iii) a $D_1$ group: a $(R_1$—$(O)_k$-$)A_1N$—$(O)_{k'}$-group ($R_1$ and $A_1$ are as defined above, and k and k' are the same or different and represent 0 or 1);

(iv) a $D_2$ group: a cyano group, a $R_1R_1'NC(=N$—$(O)_n$-$A_1$)-group ($R_1$, $R_1'$, n and $A_1$ are as defined above), an $A_1N=C(-OR_2)$-group ($A_1$ and $R_2$ are as defined above) or a $NH_2$—CS-group;

(v) a $D_3$ group: a nitro group or a $R_1OSO_2$-group ($R_1$ is as defined above);

(vi) an $A_2$ group:
1) an $A_3$-$B_4$-group
[$A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_a$—$(R_4)_m$-group ($R_a$ represents a phenyl group, a pyridyl group, a furyl group or a thienyl group, optionally substituted with a halogen atom, C1-C10 alkyl group, a C1-C10 alkoxy group or a nitro group, $R_4$ and m are as defined above), or a C1-C10 alkyl group substituted with a $(b_0)$-$R_4$-group ($(b_0)$ and $R_4$ are as defined above), a $((c_0)$-$R_4$-group ($(c_0)$ and $R_4$ are as defined above), a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $R_4$—$SO_2$—$R_4$-group {$A_4$ is as defined above, and $R_4$ is as defined above};
$B_4$ represents an oxy group, a thio group or a —$N((O)_mR_1)$ group ($R_1$ and m are as defined above), provided that when $B_4$ is a thio group, then $A_3$ is not a hydrogen atom.];

2) a $R_1$—$B_4$—CO—$R_4$—$B_4'$-group ($R_1$, $B_4$ and $R_4$ are as defined above, $B_4'$ is the same as or different from $B_4$, and has the same meaning as that of $B_4$, provided that when $B_4$ is a thio group, then $R_2$ is not hydrogen atom) or a $D_2$-$R_4$—$B_4$-group ($D_2$, $R_4$ and $B_4$ are as defined above);

3) a $R_2$—$SO_2$—$NR_1$-group ($R_2$ is as defined above, provided that a hydrogen atom is excluded; $R_1$ is as defined above);

4) a $(b_0)$-group ($(b_0)$ is as defined above);

5) a $(c_0)$-group ($(c_0)$ is as defined above); or 6) a $R_1$-$A_1N$—$NR_1'$-group ($R_1$, $A_1$ and $R_1'$ are as defined above);

IV. $W_{A0}$ represents an oxygen atom or a —$NT_{A0}$-group [$T_{A0}$ represents a hydrogen atom, an $A_9'$ group ($A_9'$ is as defined above), a $D_5$-$R_4$-group ($D_5$ and $R_4$ are as defined above) or a $M_{c0}$-group ($M_{c0}$ is as defined above)];

V. $K_{A0}$ represents a hydrogen atom, a halogen atom or a C1-C10 alkyl group, $L_{A0}$ represents a hydrogen atom, a C1-C10 alkyl group or a $M_{b0}$-group ($M_{b0}$ is as defined above), or $K_{A0}$ and $L_{A0}$ may form a C1-C10 alkylene group, or a C1-C10 alkenylene group optionally substituted with single or the same or different plural $M_a$ groups, provided that when an A ring is a benzene ring, $W_{A0}$ is an oxygen atom, $L_{A0}$ is a methyl group, $K_{A0}$ is a hydrogen atom, and $Q_{A0}$ is a C1-C4 alkoxy group, a C3-C4 alkenyloxy group or a C3-C4 alkynyloxy group, then q is not 0 and, when an A ring is a benzene ring, $W_{A0}$ is an oxygen atom, $L_{A0}$ is a methyl group, $K_{A0}$ is a hydrogen atom, and $Q_{A0}$ is a C1-C4 alkoxy group, a C3-C4 alkenyloxy group or a C3-C4 alkynyloxy group, then q is 1, and $Y_{A0}$ is not a halogen atom, or a C1-C4 alkyl group optionally substituted with a halogen atom or a C1-C4 alkoxy group, or a nitro group, or a C1-C4 alkoxy group, or a RB-group (R represents a C1-C4 haloalkyl group, and B represents an oxy group or a thio group) and, when A is a benzene ring, $W_{A0}$ is an oxygen atom, $L_{A0}$ and $K_{A0}$ form a 1,3-butadienylene group, and $Q_{A0}$ is a methoxy group, q is 1, and $Y_{A0}$ is not a methoxy group or an ethoxy group and, when A is a benzene ring, $W_{A0}$ is an oxygen atom, $L_{A0}$ and $K_{A0}$ form a 1,3-butadienylene group, and $Q_{A0}$ is a hydroxy group, then q is 1, and $Y_{A0}$ is not an ethoxy group; and the "as defined above" in the same symbol between a plurality of substituents indicates that the plurality of the substituents independently represent the same meaning as that described above and, between the plurality of substituents, a selection range of selected substituents is the same, while the selected substituents may be the same or the different as far as they are selected in the range]; and an inert carrier;

3. A I type collagen gene transcription suppressing composition, which comprises a cinnamoyl compound represented by the formula (III):

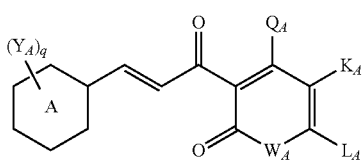

(III)

[wherein

I. A represents a benzene ring or a pyridine ring;

II. In $(Y_A)_q$, $Y_A$ is a substituent on a carbon atom, and represents a substituent of the following X group or Y group, q represents 0, 1, 2, 3, 4 or 5, when q is 2 or more, $Y_A$'s are the same or the different and, when q is 2 or more, the adjacent two same or different $Y_A$'s constitute a group of a Z group, and may be fused with an A ring;

(1) a X group: a $M_a$-group [$M_a$ represents a $R_b$-group ($R_b$ represents a C1-C10 alkyl group optionally substituted with a halogen atom), a halogen atom, a nitro group, a cyano group, a hydroxy group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_eO$—CO—$R_d$-group ($R_e$ and $R_d$ are as defined above), a HO—CO—CH=CH-group, a $R_eR_e'$N—$R_d$— group ($R_e$ and $R_e'$ are the same or different, $R_e$ is as defined above, $R_e'$ has the same meaning as that of $R_e$, and $R_d$ is as defined above), a $R_e$—CO—NR$_e'$—$R_d$-group ($R_e$, $R_e'$—$R_d$ are as defined above), a $R_bO$—CO—N($R_e$)—$R_d$-group ($R_b$, $R_e$ and $R_d$ are as defined above), a $R_eR_e'$N—CO—$R_d$-group ($R_e$, $R_e'$ and $R_d$ are as defined above), a $R_eR_e'$N—CO—NR$_e''$—$R_d$-group ($R_e$, $R_e'$ and $R_e''$ are the same or different $R_e$ and $R_e'$ are as defined above, $R_e''$ has the same meaning as that of $R_e$, and $R_d$ is as defined above), a $R_eR_e'$N—C(=NR$_e''$)—NR$_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$ and $R_d$ is as defined above), a $R_b$—SO$_2$—NR$_e$—$R_d$-group ($R_b$, $R_e$ and $R_d$ are as defined above), $R_eR_e'$N—SO$_2$—$R_d$-group ($R_e$, $R_e'$ and $R_d$ are as defined above), a C2-C10 alkenyl group or a C2-C10 alkynyl group];

(2) a Y group: a $M_b$-$R_d$-group [$M_b$ represents a $M_c$-group {$M_c$ represents a $M_d$-$R_d'$-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

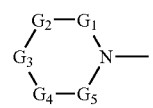

(b)

a (b)-group {in (b), $G_1$, $G_2$, $G_4$ and $G_5$ represent a methylene group which is connected to an adjacent atom with a single bond and may be substituted with a methyl group, or a methine group which is connected to an adjacent atom with a double bond, $G_3$ represents a single bond, or a double bond, or a C1-C10 alkylene group optionally substituted with a methyl group, an oxy group, a thio group, a sulfinyl group, a sulfonyl group or a-NR$_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group), or a C2-C10 alkenylene group optionally substituted with a methyl group, an oxy group, a thio group, a sulfinyl group, a sulfonyl group or a —NR$_1$-group ($R_1$ is as defined above)},

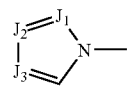

(c)

a (c)-group (in (c), $J_1$, $J_2$ and $J_3$ are the same or different, and represent a methine group optionally substituted with a methine group, or a nitrogen atom),

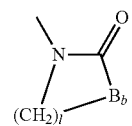

(d)

a (d)-group (l is 2, 3 or 4, and $B_b$ represents an oxy group or a thio group) or

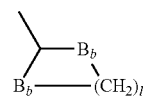

(e)

an (e)-group (l and $B_b$ are as defined above), $R_d'$ is the same as or different from $R_d$, and has the same meaning as that of $R_d$}}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_e$N-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_c R_e N$—CO-group ($M_c$ and $R_e$ are as defined above), a $M_c R_e N$—CO—$NR_e$'-group ($M_c$, $R_e$ and $R_e$' are as defined above), a $M_c R_e N$—C(=$NR_e$')—$NR_e$"-group ($M_c$, $R_e$, $R_e$' and $R_e$" are as defined above), a $M_c$-$SO_2$—$NR_e$-group ($M_c$ and $R_e$ are as defined above) or a $M_c R_e N$—$SO_2$-group ($M_c$ and $R_e$ are as defined above), and $R_d$ is as defined above];

(3) a Z group: a —N=C($Y_a$)—$Y_a$'-group ($Y_a$ represents a hydrogen atom, or a C1-C10 alkyl group optionally substituted with a halogen atom, or a C1-C10 alkoxy group, $Y_a$' represents an oxy group, or a thio group, or an imino group optionally substituted with a C1-C10 alkyl group), a —$Y_b$—$Y_b$'—$Y_b$"-group ($Y_b$ and $Y_b$" are the same or different, and represent a methylene group, or an oxy group, or a thio group, or a sulfinyl group, or an imino group optionally substituted with a C1-C10 alkyl group, and $Y_b$' represents a C1-C4 alkylene group optionally substituted with a halogen atom, or a C1-C4 alkylene group optionally having an oxo group) or a —$Y_c$—O—$Y_c$'—O-group ($Y_c$ and $Y_c$' are the same or different, and represent a C1-C10 alkylene group);

III. $Q_A$ represents a hydroxyl group, a (b)-group ((b) is as defined above), an $A_9$-$B_6$—$B_c$-group ($A_9$ represents a substituent of the following $A_7$ group or $A_8$ group, $B_6$ represents a carbonyl group or a thiocarbonyl group, $B_c$ represents an oxy group or a —N(($O)_m R_1$)-group (m represents 0 or 1, and $R_1$ is as defined above), provided that when $A_9$ is a hydrogen atom, $B_c$ is not a sulfonyl group], an $A_7$"-$SO_2$—$B_c$-group ($A_7$" represents a substituent of the following $A_7$" group, and $B_c$ is as defined above), an $A_8$-$SO_2$—$B_c$-group ($A_8$ represents a substituent of the following $A_8$ group, $B_c$ is as defined above, provided that $A_8$ is not a hydrogen atom), a $R_1 R_1$'N—$SO_2$—$B_c$-group ($R_1$ is as defined above, $R_1$' is the same as or different from $R_1$, and has the same meaning as that of $R_1$, and $B_c$ is as defined above), a (b)-$SO_2$—$B_c$-group ((b) and $B_c$ are as defined above), an $A_9$'-$B_c$-group ($A_9$' represents a substituent of the following $A_7$' group or $A_8$' group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above) or a $M_c$-$B_c$-group ($M_c$ and $B_c$ are as defined above);

(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1 R_1$'N-group ($R_1$ and $R_1$' are as defined above), and $R_4$ is as defined above} or an $A_2$-CO—$R_4$-group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7$' group: a C3-C10 alkenyl group optionally substituted with a halogen atom, a C3-C10 alkynyl group optionally substituted with a halogen atom, a $R_2$—$B_1$—$R_4$'-group ($R_2$ and $B_1$ are as defined above, and $R_4$' represents a C2-C10 alkylene group), a $D_4$-$R_4$'-group ($D_4$ and $R_4$' are as defined above), a $D_1$-$R_4$'-group ($D_1$ and $R_4$' are as defined above), a (b)-$R_4$'-group ((b) and $R_4$' are as defined above), a (c)-$R_4$'-group ((c) and $R_4$' are as defined above), a $D_2$-$R_4$-group ($D_2$ and $R_4$ are as defined above), a $D_3$-$R_4$'-group ($D_3$ and $R_4$' are as defined above) or an $A_2$-CO—$R_4$-group ($A_2$ and $R_4$ are as defined above);

(4) an $A_8$' group: a C1-C10 alkyl group or a C2-C10 haloalkyl group;

(5) an $A_7$" group: a C2-C10 alkenyl group, a C3-C10 alkenyl group substituted with a halogen atom, a C3-C10 alkynyl group optionally substituted with a halogen atom, a $R_2$—$B_1$—$R_4$'-group ($R_2$, $B_1$ and $R_4$' are as defined above), a $D_4$-$R_4$'-group ($D_4$ and $R_4$' are as defined above), a $D_5$-$R_4$'-group ($D_5$ and $R_4$ are as defined above), a $D_1$-$R_4$'-group ($D_1$ and $R_4$' are as defined above), a (b)-$R_4$'-group ((b) and $R_4$' are as defined above), a (c)-$R_4$'-group ((c) and $R_4$' are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);

(i) a $D_4$ group: a hydroxyl group or an $A_1$-O-group [$A_1$ represents a $R_3$—(CHR$_0$)$_m$—($B_2$—$B_3$)$_{m'}$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —N(O)$_n R_1$'-group ($R_1$' is as defined above, and n represents 0 or 1), $B_3$ is as defined above, m' represents 0 or 1 and, when $B_3$ is a sulfonyl group, m is 0, and $R_3$ is not a hydrogen atom}];

(ii) a $D_5$ group: O=C($R_3$)-group ($R_3$ is as defined above), an $A_1$-(O)$_n$—N=C($R_3$)-group ($A_1$, n and $R_3$ are as defined above), a $R_1$—$B_0$—CO—$R_4$—(O)$_n$—N=C($R_3$)-group [$R_1$, $R_4$, n and $R_3$ are as defined above, and $B_0$ represents an oxy group, a thio group or a —N(O)$_m R_1$')-group ($R_1$' and m are as defined above)], a $D_2$-$R_4$—(O)$_n$—N=C($R_3$)-group ($D_2$, $R_4$, n and $R_3$ are as defined above) or a $R_1 A_1 N$—N=C($R_3$)-group ($R_1$, $A_1$ and $R_3$ are as defined above);

(iii) a $D_1$ group: a ($R_1$—(O)$_k$-)$A_1 N$—(O)$_{k'}$-group ($R_1$ and $A_1$ are as defined above, and k and k' are the same or different, and represent 0 or 1);

(iv) a D group: a cyano group, a $R_1 R_1$'NC'(=N—(O)$_n$-$A_1$)-group ($R_1$, $R_1$', n and $A_1$ are as defined above), an $A_1 N$=C(—O—) group ($A_1$ and $R_2$ are as defined above) or a $NH_2$—CS-group;

(v) a $D_3$ group: a nitro group or a $R_1 OSO_2$-group ($R_1$ is as defined above);

(vi) an $A_2$ group:

1) an $A_3$-$B_4$-group
[$A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_a$—($R_4$)$_m$-group ($R_a$ represents a phenyl group, a pyridyl group, a furyl group or a thienyl group, optionally substituted with a halogen atom, a C1-C10 alkyl group, a C1-C10 alkoxy group or a nitro group, and $R_4$ and m are as defined above), or a C1-C10 alkyl group substituted with a (b)-$R_4$-group ((b) and $R_4$ are as defined above), a (c)-$R_4$-group ((c) and $R_4$ are as defined above), a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $A_4$-$SO_2$—$R_4$-group {$A_4$ is as defined above, and $R_4$ is as defined above};

$B_4$ represents an oxy group, a thio group or a —N(($O)_m$ $R_1$)— group ($R_1$ and m are as defined above) provided that when $B_4$ is a thio group, $A_3$ is not a hydrogen atom];

2) a $R_1$—$B_4$—CO—$R_4$—$B_4$'-group ($R_1$, $B_4$ and $R_4$ are as defined above, $B_4$' is the same as or different from $B_4$, and has the same meaning as that of $B_4$, provided that when $B_4$ is a thio group, a $R_2$ is not a hydrogen atom) or a $D_2$-$R_4$—$B_4$-group ($D_2$, $R_4$ and $B_4$ are as defined above);

3) a $R_2$—$SO_2$—$NR_1$-group ($R_2$ is as defined above, provided that a hydrogen atom is excluded, and $R_1$ is as defined above);

4) a (b)-group ((b) is as defined above);

5) a (c)-group ((c) is as defined above); or 6) a $R_1A_1N$—$NR_1'$-group ($R_1$, $A_1$ and $R_1'$ are as defined above);

IV. $W_A$ represents an oxygen atom or a —$NT_A$-group [$T_A$ represents a hydrogen atom, an $A_9'$-group ($A_9'$ is as defined above), a $D_5$-$R_4$-group ($D_5$ and $R_4$ are as define above) or a $M_c$-group ($M_c$ is as defined above)];

V. $K_A$ represents a hydrogen atom, a halogen atom or a C1-C10 alkyl group, $L_A$ represents a hydrogen atom, a C1-C10 alkyl group or a $M_b$-group ($M_b$ is as defined above), or $K_A$ and $L_A$ may form a C1-C10 alkylene group or a —C($M_a'$)=C($M_a''$)-C($M_a'''$)=C($M_a''''$)-group ($M_a'$, $M_a''$, $M_a'''$ and $M_a''''$ are the same or different, are the same as or different from $M_a$, and represent a hydrogen atom or $M_a$); and provided that when an A ring is a benzene ring, $W_A$ is an oxygen atom, $L_A$ is a methyl group, $K_A$ is a hydrogen atom, and $Q_A$ is a C1-C10 alkoxy group, a C3-10 alkenyloxy group or a C3-C10 alkynyloxy group, then q is not 0 and, when an A ring is a benzyl ring, $W_A$ is an oxygen atom, $L_A$ is a methyl group, $K_A$ is a hydrogen atom, and $Q_A$ is a C1-C10 alkoxy group, a C3-C10 alkenyloxy group or a C3-C10 alkynyloxy group, then q is 1, and $Y_A$ is not a halogen atom, or C1-C10 alkyl group optionally substituted with a halogen atom or a C1-C10 alkoxy group, or a nitro group, or a C1-C10 alkoxy group, or a RB-group (R represents a C1-C10 haloalkyl group and B represents an oxy group or a thio group) and, when A is a benzene ring, $W_A$ is an oxygen atom, $L_A$ and $K_A$ form a 1,3-butadienylene group, and $Q_A$ is a hydroxyl group or a C1-C10 alkoxy group, then q is 1, and $Y_A$ is not a C1-C10 alkoxy group; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range]; and an inert carrier;

4. A I type collagen gene transcription suppressing composition, which comprises a 2H-pyran-2-one compound represented by the formula (IV):

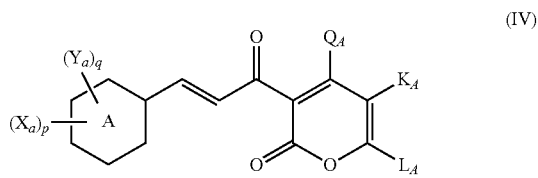

[wherein

I. A represents a benzene ring or a pyridine ring;

II. In $(X_a)_p$, $X_a$ is a substituent on a carbon atom, and represents a halogen atom, or a C1-C10 alkyl group optionally substituted with a halogen atom or a C1-C10 alkoxy group, or a nitro group, a C1-C10 alkoxy group, or a RB-group (R represents a C1-C10 haloalkyl group, and B represents an oxy group or a thio group), p represents 0, 1, 2, 3 or 4 and, when p is 2 or more, $X_a$'s are the same or different;

III. In $(Y_a)_q$, $Y_a$ is a substituent on a carbon atom, and represents a substituent of the following $X_1$ group or $Y_1$ group, q represents 0, 1, 2, 3, 4 or 5, when q is 2 or more, $Y_a$'s are the same or different and, when q is 2 or more, the adjacent two same or different $Y_a$'s constitute a $Z_1$ group, and may be fused with an A ring;

(1) a $X_1$ group:

a $M_a$-group [$M_a$ represents a $R_b$-group ($R_b$ represents a C1-C10 alkyl group optionally substituted with a halogen atom), a halogen atom, a nitro group, a cyano group, a hydroxyl group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_e$O—CO—$R_d$-group ($R_e$ and $R_d$ are as defined above), a HO—CO—CH=CH-group, a $R_eR_e'$N—$R_d$-group ($R_e$ and $R_e'$ are the same or different, $R_e$ is as defined above, $R_e'$ has the same meaning as that of $R_e$, and $R_d$ is as defined above), a $R_e$—CO—$NR_e'$—$R_d$-group ($R_e$, $R_e'$ and $R_d$ are as defined above), a $R_bO$—CO—N($R_e$)—$R_d$-group ($R_b$, $R_e$ and $R_d$ are as defined above), a $R_eR_e'$N—CO—$R_d$-group ($R_e$, $R_e'$ and $R_d$ are as defined above), a $R_eR_e'$N—CO—$NR_e''$—$R_d$-group ($R_e$, $R_e'$ and $R_e''$ are the same or different, $R_e$ and $R_e'$ are as defined above, $R_e''$ has the same meaning as that of $R_e$, and $R_d$ is as defined above), a $R_eR_e'$N—C(=$NR_e''$)—$NR_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—$SO_2$—$NR_e$—$R_d$-group ($R_b$, $R_e$ and $R_d$ are as defined above), a $R_eR_e'$N—$SO_2$—$R_d$-group ($R_e$, $R_e''$ and $R_d$ are as defined above), a C2-C10 alkenyl group or a C2-C10 alkynyl group], provided that when A represents a benzene ring, a $X_a$-group ($X_a$ is as defined above) is excluded;

(2) a $Y_1$ group:

a $M_b$-$R_d$-group [$M_b$ represents a $M_c$-group {$M_c$ represents a $M_d$-$R_d'$-group {$M_d$ represents a phenyl group optionally substituted with a $M_a$-group ($M_a$ is as defined above), or a pyridyl group optionally substituted with a $M_a$-group ($M_a$ is as defined above) or a naphthyl group optionally substituted with a $M_a$-group ($M_a$ is as defined above), or

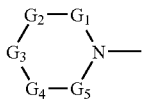
(b)

a (b)-group {in (b), $G_1$, $G_2$, $G_4$ and $G_5$ represent a methylene group which is connected to an adjacent atom with a single bond and may be substituted with a methyl group, or a methine group which is connected to an adjacent atom with a double bond and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —$NR_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C—C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group}, or a C2-C10 alkenylene group optionally substituted with a methyl group, an oxy group, a thio group, a sulfinyl group, a sulfonyl group or a —$NR_1$-group ($R_1$ is as defined above)},

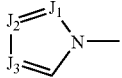
(c)

a (c)-group (in (c), $J_1$, $J_2$ and $J_3$ are the same or different, and represent a methine group optionally substituted with a methyl group, or a nitrogen atom),

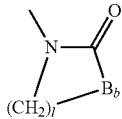
(d)

a (d)-group (l is 2, 3 or 4, and $B_b$ represents an oxy group, or a thio group), or

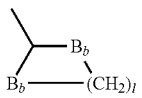
(e)

an (e)-group (l and $B_b$ are as defined above), $R_d'$ is the same as or different from $R_d$, and has the same meaning as that of $R_d$}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_eN$-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_cR_eN$—CO-group ($M_c$ and $R_e$ are as defined above), a $M_cR_eN$—CO—$NR_e'$-group ($M_c$, $R_e$ and $R_e'$ are as defined above), a $M_cR_eN$—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_cR_eN$—$SO_2$-group ($M_c$ and $R_e$ are as defined above), and $R_d$ is as defined above];

(3) a $Z_1$ group:
a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$—$Y_b''$-group ($Y_b$ and $Y_b''$ are the same or different, and represent a methylene group, or an oxy group, or a thio group, or a sulfinyl group, or an imino group optionally substituted with a C1-C10 alkyl group, and $Y_b'$ represents a C1-C4 alkylene group optionally substituted with a halogen atom, or a C1-C4 alkylene group optionally having an oxo group) or a —$Y_c$—O—$Y_c'$—O-group ($Y_c$ and $Y_c'$ are the same or different, and represent a C1-C10 alkylene group);

IV. $Q_A$ represents a hydroxyl group, a (b)-group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, $B_c$ represents an oxy group or a —N(($O)_mR_1$)-group (m represents 0 or 1, and $R_1$ is as defined above), provided that when $A_9$ is a hydrogen atom, $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1R_1'N$—$SO_2$—$B_c$-group ($R_1$ is as defined above, $R_1'$ is the same as or different from $R_1$, and has the same meaning as that of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), $M_c$-$B_3$—$B_c$-group ($B_3$ represents a carbonyl group, a thiocarbonyl group or a sulfonyl group and $M_c$ and $B_c$ are as defined above) or a $M_c$-$B_c$-group ($M_c$ and $B_c$ are as defined above);

(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, $R_4$ is as defined above), a $D_1$-$R_4$-group {$D_1$ represents a substituent of the following $D_1$ group, and $R_4$ is as defined above}, a (b)-$R_4$-group {(b) is as defined above, and $R_4$ is as defined above}, a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1R_1'N$-group ($R_1$ and $R_1'$ are as defined above), and $R_4$ is as defined above} or an $A_2$-CO—$R_4$-group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$-group ($D_4$ and $R_4'$ are as defined above), a D₁-R₄'-group (D₁ and R₄' are as defined above), a (b)-R₄'-group ((b) and R₄' are as defined above), a (c)-R₄'-group ((c) and R₄' are as defined above), a D₂-R₄-group (D₂ and R₄ are as defined above), a D₃-R₄'-group (D₃ and R₄' are as defined above) or an A₂-CO—R₄-group (A₂ and R₄ are as defined above);

(4) an A₈' group: a C1-C10 alkyl group or a C2-C10 haloalkyl group;

(5) an A₇'' group: a C2-C10 alkenyl group, a C3-C10 alkenyl group substituted with a halogen atom, a C3-C10 alkynyl group optionally substituted with a halogen atom, a R₂—B₁—R₄'-group (R₂, B₁ and R₄' are as defined above), a D₄-R₄'-group (D₄ and R₄' are as defined above), a D₅-R₄-group (D₅ and R₄ are as defined above), a D₁-R₄'-group (D₁ and R₄' are as defined above), (b)-R₄'-group ((b) and R₄' are as defined above), a (c)-R₄'-group ((c) and R₄' are as defined above), a D₂-R₄-group (D₂ and R₄ are as defined above), a NO₂—R₄-group (R₄ is as defined above) or an A₂-CO—R₄-group (A₂ and R₄ are as defined above);

(i) a D₄ group: a hydroxyl group or an A₁-O-group [A₁ represents a R₃—(CHR₀)ₘ—(B₂—B₃)ₘ'-group {R₃ represents a hydrogen atom, or a C1-C10 alkyl group optionally substituted with a halogen atom or a R₂—B₁-group (R₂ and B₁ are as defined above), or a C2-C10 alkenyl group, or a C2-C10 alkynyl group, R₀ represents a hydrogen atom, a C1-C10 alkyl group or a C2-C10 haloalkyl group, m is as defined above, B₂ represents a single bond, an oxy group, a thio group or a —N(O)ₙR₁')-group (R₁' is as defined above, and n represents 0 or 1, B₃ is as defined above, m' represents 0 or 1 and, when B₃ is a sulfonyl group, m is 0, and R₃ is not a hydrogen atom)}];

(ii) a D₅ group: an O=C(R₃)-group (R₃ is as defined above), an A₁-(O)ₙ—N=C(R₃)-group (A₁, n and R₃ are as defined above), a R₁—B₀—CO—R₄—(O)ₙ—N=C(R₃)-group [R₁, R₄, n and R₃ are as defined above, and B₀ represents an oxy group, a thio group or a —N((O)ₘR₁')-group (R₁' and m are as defined above)], a D₂-R₄—(O)ₙ—N=C(R₃-group (D₂, R₄, n and R₃ are as defined above) or a R₁A₁N—N=C(R₃)-group (R₁, A₁ and R₃ are as defined above);

(iii) a D₁ group: a (R₁—(O)ₖ-)A₁N—(O)ₖ'-group (R₁ and A₁ are as defined above, and k and k' are the same or different, and represent 0 or 1);

(iv) a D₂ group: a cyano group, a R₁R₁'NC(=N—(O)ₙ-A)-group (R₁, R₁', n and N₁ are as defined above), an A₁N=C(—OR₂)-group (A₁ and R₂ are as defined above) or a NH₂—CS-group.

(v) a D₃ group: a nitro group or a R₁OSO₂-group (R₁ is as defined above);

(vi) an A₂ group:

1) an A₃-B₄-group

[A₃ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a Rₐ—(R₄)ₘ-group (Rₐ represents a phenyl group, a pyridyl group, a furyl group or a thienyl group, optionally substituted with a halogen atom, a C1-C10 alkyl group, a C1-C10 alkoxy group or a nitro group, and R₄ and m are as defined above), or a C1-C10 alkyl group substituted with a (b)-R₄-group ((b) and R₄ are as defined above), a (c)-R₄-group ((c) and R₄ are as defined above), a R₂—B₁—R₄-group (R₂, B₁ and R₄ are as defined above), a D₄-R₄-group (D₄ and R₄ are as defined above), a D₅-group (D₅ is as defined above), a D₁-R₄-group (D₁ and R₄ are as defined above), a D₂-group (D₂ is as defined above), a D₃-R₄-group (D₃ and R₄ are as defined above) or an A₄-SO₂—R₄-group {A₄ is as defined above, and R₄ is as defined above}; B₄ represents an oxy group, a thio group or a —N((O)ₘR₁)-group (R₁ and m are as defined above), provided that when B₄ is a thio group, A₃ is not a hydrogen atom];

2) a R₁—B₄—CO—R₄—B₄'-group (R₁, B₄ and R₄ are as defined above, B₄' is the same as or different from B₄, and has the same meaning as that of B₄, provided that when B₄ is a thio group, R₂ is not a hydrogen atom) or a D₂-R₄—B₄-group (D₂, R₄ and B₄ are as defined above);

3) a R₂—SO₂—NR₁-group (R₂ is as defined above, provided that a hydrogen atom is excluded, and R₁ is as defined above), 4) a (b)-group ((b) is as defined above);

5) a (c)-group ((c) is as defined above); or 6) a R₁A₁N—NR₁'-group (R₁, R₁ and R₁' are as defined above);

V. Kₐ represents a hydrogen atom, a halogen atom or a C1-C10 alkyl group, Lₐ represents a hydrogen atom, a C1-C10 alkyl group or a M_b-group (M_b is as defined above), or Kₐ and Lₐ may form a C1-C10 alkylene group, provided that when Kₐ is a hydrogen atom, Lₐ is a methyl group and an A ring is a benzene ring, p is 2, 3 or 4 in the case that q is 0; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in a range]; and an inert carrier;

5. A 2H-pyran-2-one compound represented by the formula (V):

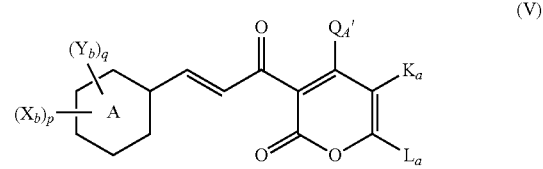

[wherein

I. A represents a benzene ring or a pyridine ring;

II. In (X_b)_p, X_b is a substituent on a carbon atom, and represents a halogen atom, or a C1-C10 alkyl group optionally substituted with a halogen atom or a C1-C10 alkoxy group, or a nitro group, or a C2-C10 alkoxy group, or a RB-group (R represents a C1-C10 haloalkyl group, and B represents an oxy group or a thio group), p represents 0, 1, 2, 3 or 4 and, when p is 2 or more, X_b's are the same or different;

III. In (Y_b)_q, Y_b is a substituent on a carbon atom, and represents a substituent of the following X₂ group or Y₂ group, q represents 0, 1, 2, 3, 4 or 5, when q is 2 or more, Y_b's are the same or different and, when q is 2 or more, the adjacent two same or different Y_b's constitutes a group of a Z₂ group, and may be fused with an A ring;

(1) a X₂ group:

a Mₐ-group [Mₐ represents a R_b-group (R_b represents a C1-C10 alkyl group optionally substituted with a halogen atom), a halogen atom, a nitro group, a cyano group, a hydroxy group, a R_c—Bₐ—R_d-group (R_c represents a C1-C10 alkyl group optionally substituted with a halogen atom, Bₐ represents an oxy group, a thio group, a sulfinyl group or a sulfonyl group, and R_d represents a single bond or a C1-C10 alkylene group), a HOR_d-group (R_d is as defined above), a R_e—CO—R_d-group (R_e represents a hydrogen atom, or a C1-C10 alkyl group optionally substituted with a halogen atom, and R$_d$ is as defined above), a R$_e$—CO—O—R$_d$-group (R$_e$ and R$_d$ are as defined above), a R$_e$O—CO—R$_d$-group (R$_e$ and R$_d$ are as defined above), a HO—CO—CH=CH-group, a R$_e$R$_e$'N—R$_d$-group (R$_e$ and R$_e$' are the same or different, R$_e$ is as defined above, R$_e$' has the same meaning as that of R$_e$, and R$_d$ is as defined above), a R$_e$—CO—NR$_e$'—R$_d$-group (R$_e$, R$_e$' and R$_d$ are as defined above), a R$_b$O—CO—N(R$_e$)—R$_d$-group (R$_b$, R$_e$ and R$_d$ are as defined above), a R$_e$R$_e$'N—CO—R$_d$-group (R$_e$, R$_e$' and R$_d$ are as defined above), a R$_e$R$_e$'N—CO—NR$_d$"—R$_d$-group (R$_e$, R$_e$' and R$_e$" are the same or different, R$_e$ has the same meaning as that of R$_e$', R$_e$" has the same meaning as that of R$_e$, and R$_d$ is as defined above), a R$_e$R$_e$'N—C(=NR$_e$")—NR$_e$'"—R$_d$-group (R$_e$, R$_e$', R$_e$" and R$_e$'" are the same or different, R$_e$, R$_e$' and R$_e$" are as defined above, R$_e$'" has the same meaning as that of R$_e$, and R$_d$ is as defined above), a R$_b$—SO$_2$—NR$_e$—R$_d$-group (R$_b$, R$_e$ and R$_d$ are as defined above), a R$_e$R$_e$'N—SO$_2$—R$_d$-group (R$_e$, R$_e$' and R$_d$ are as defined above), a C2-C10 alkenyl group or a C2-C10 alkynyl group], provided that, when A represents a benzene ring, then, a halogen atom, or a C1-C10 alkyl group optionally substituted with a halogen atom or a C1-C10 alkoxy group, or a nitro group, or a C1-C10 alkoxy group, or a RB-group (R and B are as described above) is excluded;

(2) a Y$_2$ group:

a M$_b$-R$_d$-group [M$_b$ represents a M$_c$-group {M$_c$ represents a M$_d$-R$_d$'-group {M$_d$ represents a phenyl group optionally substituted with a M$_a$-group (M$_a$ is as defined above), or a pyridyl group optionally substituted with a M$_a$-group (M$_a$ is as defined above), or a naphthyl group optionally substituted with a M$_a$-group (M$_a$ is as defined above) or

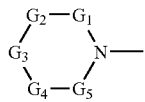

(b)

a (b)-group {in (b), G$_1$, G$_2$, G$_4$ and G$_5$ represent a methylene group which is connected to an adjacent atom with a single bond and may be substituted with a methyl group, or a methine group which is connected to an adjacent atom with a double bond and may be substituted with a methyl group, and G$_3$ represents a single bond, or a double bond, or a C1-C10 alkylene group optionally substituted with a methyl group, an oxy group, a thio group, a sulfinyl group, a sulfonyl group, or a —NR$_1$-group {R$_1$ represents a hydrogen atom, or a C1-C10 alkyl group, or a C2-C10 alkyl group substituted with a halogen atom or a R$_2$—B$_1$-group (R$_2$ represents a C1-C10 alkyl group, a C3-C10 alkenyl group or a C3-C10 alkynyl group, and B$_1$ represents an oxy group, a thio group, a sulfinyl group or a sulfonyl group), or a C3-C10 alkenyl group or a C3-C10 alkynyl group}, or a C2-C10 alkenylene group optionally substituted with a methyl group, an oxy group, a thio group, a sulfinyl group, a sulfonyl group or a NR$_1$— group (R$_1$ is as defined above)},

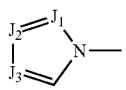

(c)

a (c)-group (in (c), J$_1$, J$_2$ and J$_3$ are the same or different, and represent a methine group optionally substituted with a methyl group, or a nitrogen atom), (d)

a (d) group (l is 2, 3 or 4, and B$_b$ represents an oxy group or a thio group) or (e)

an (e)-group (l and B$_b$ are as defined above), R$_d$' is the same as or different from R$_d$, and has the same meaning as that of R$_d$}, a M$_c$-B$_a$-group (M$_c$ and B$_a$ are as defined above), a M$_c$-CO-group (M$_c$ is as defined above), a M$_c$-CO—O-group (M$_c$ is as defined above), a M$_c$O—CO-group (M$_c$ is as defined above), a M$_c$R$_e$N-group (M$_c$ and R$_e$ are as defined above), a M$_c$-CO—NR$_e$-group (M$_c$ and R$_e$ are as defined above), a M$_c$O—CO—NR$_e$-group (M$_c$ and R$_e$ are as defined above), a M$_c$R$_e$N—CO-group (M$_c$ and R$_e$ are as defined above), a M$_c$R$_e$N—CO—NR$_e$'-group (M$_c$, R$_e$ and R$_d$' are as defined above), a M$_c$R$_e$N—C(=NR$_e$')—NR$_e$"-group (M$_c$, R$_e$, R$_e$' and R$_e$" are as defined above), a M$_c$-SO$_2$—NR$_e$-group (M$_c$ and R$_e$ are as defined above) or M$_c$R$_e$N—SO$_2$-group (M$_c$ and R$_e$ are as defined above), and R$_d$ is as defined above];

(3) a Z$_2$ group:

a —N=C(Y$_a$)Y$_a$'-group (Y$_a$ represents a hydrogen atom, or a C1-C10 alkyl group optionally substituted with a halogen atom, or a C1-C10 alkoxy group, and Y$_a$' represents an oxy group, or a thio group, or an imino group optionally substituted C1-C10 alkyl group), a —Y$_b$—Y$_b$'—Y$_b$"-group (Y$_b$ and Y$_b$" are the same or different, and represent a methylene group, or an oxy group, or a thio group, or a sulfinyl group, or an imino group optionally substituted with a C1-C10 alkyl group, and Y$_b$' represents a C1-C4 alkylene group optionally substituted with a halogen atom, or a C1-C4 alkylene group optionally having an oxo group) or a —Y$_c$—O—Y$_c$'—O-group (Y$_c$ and Y$_c$' are the same or different, and represent a C1-C10 alkylene group);

III. Q$_A$' represents a (b)-group ((b) is as defined above), an A$_9$-B$_6$—B$_c$-group [A$_9$ represents a substituent of the following A$_7$ group or A$_8$ group, B$_6$ represents a carbonyl group or a thiocarbonyl group, and B$_c$ represents an oxy group or a —N((O)$_m$R$_1$-group (m represents 0 or 1, and R$_1$ is as defined above), provided that when A$_9$ is a hydrogen atom, then B$_c$ is not a sulfonyl group], an A$_7$"—SO$_2$—B$_c$-group (A$_7$" represents a substituent of the following A$_7$" group, and B$_c$ is as defined above), an A$_8$-SO$_2$—B$_c$-group (A$_8$ represents a substituent of the following A$_8$ group, and B$_c$ is as defined above, provided that A$_8$ is not a hydrogen atom), a R$_1$R$_1$'N—SO$_2$—B$_c$-group (R$_1$ is as defined above, R$_1$' is the same as or different from R$_1$, and has the same meaning as that of R$_1$ and B$_c$ is as defined above), a (b)-SO$_2$—B$_c$-group ((b) and B$_c$ are as defined above), an A$_9$'-B$_c$-group (A$_9$' represents a substituent of the following A$_7$' group or A$_8$' group, and B$_c$ is as defined above), a D$_5$-R$_4$—B$_c$-group (D$_5$ represents a substituent of the following D$_5$ group, R$_4$ represents a C1-C10 alkylene group, and B$_c$ is as defined above), a M$_c$-B$_3$—B$_c$-group (B$_3$ represents a carbonyl group, a thiocarbonyl group or a sulfonyl group, and $M_c$ and $B_c$ are as defined above) or a $M_c$-$B_c$-group ($M_c$ and $B_c$ are as defined above);

(1) an $A_7$ group:

a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1R_1$'N-group ($R_1$ and $R_1$' are as defined above), and $R_4$ is as defined above} or an $A_2$-CO—$R_4$-group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7$' group: a C3-C10 alkenyl group optionally substituted with a halogen atom, a C3-C10 alkynyl group optionally substituted with a halogen atom, a $C_2$—$B_1$—$R_4$'-group ($C_2$ and $B_1$ are as defined above, and $R_4$' represents a C2-C10 alkylene group), a $D_4$-$R_4$'-group ($D_4$ and $R_4$' are as defined above), a $D_1$-$R_4$'-group ($D_1$ and $R_4$' are as defined above), a (b)-$R_4$'-group ((b) and $R_4$' are as defined above), a (c)-$R_4$'-group ((c) and $R_4$' are as defined above), a $D_2$-$R_4$'-group ($D_2$ and $R_4$ are as defined above), a $D_3$-$R_4$'-group ($D_3$ and $R_4$' are as defined above) or an $A_2$-CO—$R_4$-group ($A_2$ and $R_4$ are as defined above);

(4) an $A_8$-group: a C1-C10 alkyl group or a C2-C10 haloalkyl group;

(5) an $A_7$"-group: a C2-C10 alkenyl group, a C3-C10 alkenyl group substituted with a halogen atom, a C3-C10 alkynyl group optionally substituted with a halogen atom, a $R_2$—$B_1$—$R_4$'-group ($R_2$, $B_1$ and $R_4$' are as defined above), a $D_4$-$R_4$'-group ($D_4$ and $R_4$' are as defined above), a $D_5$-$R_4$'-group ($D_5$ and $R_4$ are as defined above), a $D_1$-$R_4$'-group ($D_1$ and $R_4$" are as defined above), a (b)-$R_4$'-group ((b) and $R_4$' are as defined above), a (c)-$R_4$'-group ((c) and $R_4$' are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);

(i) a $D_4$ group: a hydroxyl group or an $A_1$-O-group [$A_1$ represents a $R_3$—$(CHR_0)_m$—$(B_2$—$B_3)_{m'}$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C1 alkynyl group, $R_0$ represents a hydrogen atom, C1-C10 alkyl group or a C2-C10 haloalkyl group, m is as defined above, $B_2$ represents a single bond, an oxy group, a thio group or a —$N((O)_nR_1'$)-group ($R_1$' is as defined above, and n represents 0 or 1), $B_3$ is as defined above, and m' represents 0 or 1 and, when $B_3$ is a sulfonyl group, m is 0, and $R_3$ is not a hydrogen atom}];

(ii) a $D_5$ group: O=$C(R_3)$ group ($R_3$ is as defined above), an $A_1$-$(O)_n$—N=$C(R_3)$-group ($A_1$, n and $R_3$ are as defined above), an $R_1$—$B_0$—CO—$R_4$—$(O)_n$—N=$C(R_3)$-group [$R_1$, $R_4$, n and $R_3$ are as defined above, and $B_0$ represents an oxy group, a thio group or a —$N((O)_mR_1'$)-group ($R_1$' and m are as defined above)], a $D_2$-$R_4$— $(O)_n$—N=$C(R_3)$-group ($D_2$, $R_4$, n and $R_3$ are as defined above) or a $R_1A_1N$—N=$C(R_3)$ group ($R_1$, $A_1$ and $R_3$ are as defined above);

(iii) a $D_1$ group: a $(R_1$—$(O)_k$-)$A_1N$—$(O)_k$'-group ($R_1$ and $A_1$ are as defined above, and k and k' are the same or different, and represent 0 or 1);

(iv) a $D_2$ group: a cyano group, a $R_1R_1$'NC(=N—$(O)_n$-$A_1$-group ($R_1$, $R_1$', n and $A_1$ are as defined above), an $A_1N$=C(—$OR_2$)-group ($A_1$ and $R_2$ are as defined above) or a $NH_2$—CS-group.

(v) a $D_3$ group: a nitro group or a $R_1OSO_2$-group ($R_1$ is as defined above);

(vi) an $A_2$ group:

1) an $A_3$-$B_4$-group

[$A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_a$—$(R_4)_m$-group ($R_a$ represents a phenyl group, a pyridyl group, a furyl group or a thienyl group, optionally substituted with a halogen atom, a C1-C10 alkyl group, a C1-C10 alkoxy group or a nitro group, and $R_4$ and m are as defined above), or a C1-C10 alkyl group substituted with a (b)-$R_4$-group ((b) and $R_4$ are as defined above), a (c)-$R_4$-group ((c) and $R_4$ are as defined above), a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $A_4$-$SO_2$—$R_4$-group {$A_4$ is as defined above, and $R_4$ is as defined above}, $B_4$ represents an oxy group, a thio group or a —$N((O)_mR_1$)-group ($R_1$ and m are as defined above), provided that when $B_4$ is a thio group, $A_3$ is not a hydrogen atom];

2) a $R_1$—$B_4$—CO—$R_4$—$B_4$'-group ($R_1$, $B_4$ and $R_4$ are as defined above, $B_4$' is the same as or different from $B_4$, and has the same meaning as that of $B_4$ provided that when $B_4$ is a thio group, $R_2$ is not a hydrogen atom) or a $D_2$-$R_4$—$B_4$-group ($D_2$, $R_4$ and $B_4$ are as defined above);

3) a $R_2$—$SO_2$—$NR_1$-group ($R_2$ is as defined above provided that a hydrogen atom is excluded, and $R_1$ is as defined above), 4) a (b)-group ((b) is as defined above);

5) a (c)-group ((c) is as defined above); or 6) a $R_1A_1N$—$NR_1$'-group ($R_1$, $A_1$ and $R_1$' are as defined above);

IV. $K_a$ represents a hydrogen atom, a halogen atom or a C1-C10 alkyl group, $L_a$ represents a hydrogen atom, a C1-C10 alkyl group or a $M_b$-group ($M_b$ is as defined above), or $K_a$ and $L_a$ may form a C1-C10 alkylene group, provided that when an A ring is a benzene ring, p is 2, 3 or 4 in the case that q is 0; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range];

6. A 2H-pyran-2-one compound represented by the formula (VI):

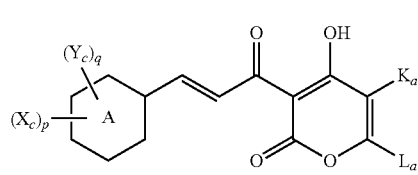

[wherein
I. A represents a benzene ring or a pyridine ring;
II. In $(X_c)_p$, $X_c$ is a substituent on a carbon atom, and represents a hydroxyl group, or a halogen atom, or a C1-C10 alkyl group optionally substituted with a halogen atom or a C1-C10 alkoxy group, or a C2-C10 alkenyl group, or a R'—S(O)$_l$-group (R' represents a C1-C10 alkyl group, and l represents 0, 1 or 2), or a cyano group, or a C1-C10 alkoxycarbonyl group, or an aminocarbonyl group, or a (R')$_2$N-group (R' is as defined above), or a R'CO—NH-group (R' is as defined above), or a nitro group, or a C1-C10 alkoxy group, or a RB-group (R represents a C1-C10 haloalkyl group, and B represents an oxy group or a thio group), p represents 0, 1, 2, 3 or 4 and, when p is 2 or more, $X_c$'s are the same or different;
III. In $(Y_c)_q$, $Y_c$ is a substituent on a carbon atom, and represents a substituent of the following $X_3$ group or $Y_3$ group, q represents 0, 1, 2, 3, 4 or 5, when q is 2 or more, $Y_c$'s are the same or different and, when q is 2 or more, the adjacent two same or different $Y_c$'s constitute a group of a $Z_3$ group, and may be fused with an A ring;
(1) a $X_3$ group:
a $M_a$-group [$M_a$ represents a $R_b$-group ($R_b$ represents a C1-C10 alkyl group substituted with a halogen atom), a halogen atom, a nitro group, a cyano group, a hydroxy group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_e$O—CO—$R_d$-group ($R_e$ and $R_d$ are as defined above), a HO—CO—CH=CH-group, a $R_e R_e$'N—$R_d$-group ($R_e$ and $R_e$' are the same or different, $R_e$ is as defined above, $R_e$' has the same meaning as that of $R_e$, and $R_d$ is as defined above), a $R_e$—CO—NR$_e$'—$R_d$-group ($R_e$, $R_e$' and $R_d$ are as defined above), a $R_b$O—CO—N($R_e$)—$R_d$-group ($R_b$, $R_e$ and $R_d$ are as defined above), a $R_e R_e$'N—CO—$R_d$-group ($R_e$, $R_e$' and $R_d$ are as defined above), a $R_e R_e$'N—CO—NR$_e$''—$R_d$-group ($R_e$, $R_e$' and $R_e$'' are the same or different, $R_e$ and $R_e$' are as defined above, $R_e$'' has the same meaning as that of $R_e$, and $R_d$ is as defined above), a $R_e R_e$'N—C(=NR$_e$'')—NR$_e$'''—$R_d$-group ($R_e$, $R_e$', $R_e$'' and $R_e$''' are the same or different, $R_e$, $R_e$' and $R_e$'' are as defined above, $R_e$''' has the same meaning as that of $R_e$, and $R_d$ is as defined above), a $R_b$—SO$_2$—NR$_e$—$R_d$-group ($R_b$, $R_e$ and $R_d$ are as defined above), a $R_e R_e$'N—SO$_2$—$R_d$-group ($R_e$, $R_e$' and $R_d$ are as defined above), a C2-C10 alkenyl group or a C2-C10 alkynyl group], provided that when A represents a benzene ring, then a hydroxy group, or a halogen atom, or a C1-C10 alkyl group optionally substituted with a halogen atom or a C1-C10 alkoxy group, or a C2-C10 alkenyl group, or a R'—S(O)$_l$-group (R' represents a C1-C10 alkyl group, and l represents 0, 1 or 2), or a cyano group, or a C1-C10 alkoxycarbonyl group, or an aminocarbonyl group, or a (R')$_2$N-group (R' is as defined above), or a R'CO—NH-group (R' is as defined above), or a nitro group or a C1-C10 alkoxy group is excluded;
(2) a $Y_3$ group:
a $M_b$-$R_d$-group [$M_b$ represents a $M_c$-group {$M_c$ represents a $M_d$-$R_d$'-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

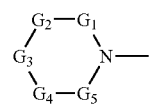

(b)

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —NR$_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group) or a C3-C10 alkenyl group, or a C3-C10 alkynyl group), or a C2-C10 alkenylene group optionally substituted with a methyl group, an oxy group, a thio group, a sulfinyl group, a sulfonyl group or a —NR$_1$-group ($R_1$ is as defined above)},

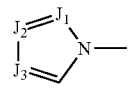

(c)

a (c)-group (in (c), $J_1$, $J_2$ and $J_3$ are the same or different, and represent a methine group optionally substituted with a methyl group, or a nitrogen atom),

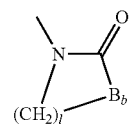

(d)

a (d)-group (l is 2, 3 or 4, and $B_b$ represents an oxy group or a thio group)

or

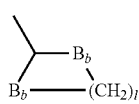

an (e)-group (l and $B_b$ are as defined above), $R_d'$ is the same as or different from $R_d$, and has the same meaning as that of $R_d$]}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_eN$-group ($M_c$ and $R_e$ are as defined above), a $M_c$-CO—$NR_e$-group ($M_c$ and $R_e$ are as defined above), a $M_cO$—CO—$NR_e$-group ($M_c$ and $R_e$ are as defined above), a $M_cR_eN$—CO-group ($M_c$ and $R_e$ are as defined above), a $M_cR_eN$—CO—$NR_e'$-group ($M_c$, $R_e$ and $R_e'$ are as defined above), a $M_cR_eN$—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_cR_eN$—$SO_2$-group ($M_c$ and $R_e$ are as defined above), and $R_d$ is as defined above], provided that when P is 0, then a morpholino group, or a phenyl group, or a phenoxy group substituted with a trifluoromethyl group, or a phenoxy group substituted with single or plural halogen atoms is excluded;

(3) a $Z_3$ group:

a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$—$Y_b''$-group ($Y_b$ and $Y_b''$ are the same or different, and represent a methylene group, or an oxy group, or a thio group, or a sulfinyl group, or an imino group optionally substituted with a C1-C10 alkyl group, and $Y_b'$ represents a C1-C4 alkylene group optionally substituted with a halogen atom, or a C1-C4 alkylene group optionally having an oxo group) or a —$Y_c$—O—$Y_c'$—O-group ($Y_c$ and $Y_c'$ are the same or different, and represent a C1-C10 alkylene group), provided that when p is 0, then $Y_c$ is not fused with an A ring to form a benzo[1,3]dioxol ring;

IV. $K_a$ represents a hydrogen atom, a halogen atom or a C1-C10 alkyl group, $L_a$ represents a hydrogen atom, a C1-C10 alkyl group or a $M_b$-group ($M_b$ is as defined above), or $K_a$ and $L_a$ may form a C1-C10 alkylene group, provided that when an A ring is a benzene ring, then q is not 0 and, when an A ring is a benzene ring or a pyridine ring, then p and q are not 0 at the same time, in either case; and the "as defined above" in the same symbol between a plurality of substituents indicates that the plurality of substituents independently represent the same meaning as that described above, and between the plurality of substituents, a selection range of selected substituents is the same, while the selected range may be the same or different as far as they are selected in the range];

7. A I type collagen gene transcription suppressing composition, which comprises a 2H-pyran-2-one compound represented by the formula (VII):

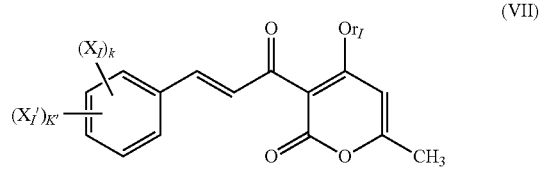

[wherein $X_I$ represents a C2-C4 alkenyl group, a C2-C4 alkynyl group, a $R_I$—S(O)$_l$-group ($R_I$ represents a C1-C4 alkyl group, and l represents an integer of 0 to 2), a cyano group, a carboxy group, a C1-C4 alkoxycarbonyl group, a $(R_I)_2$N-group ($R_I$ is as defined above), a $R_I$—CO—NH-group ($R_I$ is as defined above), a $R_I$O—CO—NH-group ($R_I$ is as defined above), a $R_I$NH—CO—NH-group ($R_I$ is as defined above) or a $(R_I')_2$N—CO-group ($R_I'$ represents a hydrogen atom or a C1-C4 alkyl group), $X_1'$ represents a halogen atom, or a C1-C4 alkyl group optionally substituted with a halogen atom or a C1-C4 alkoxy group, or a nitro group, or a C1-C4 alkoxy group, or a RB-group (B represents an oxygen atom or a sulfur atom, and R represents a C1-C4 alkyl group substituted with a halogen atom), k represents 0 or 1, k' represents an integer of 0 to 4, when k is 0, k' is an integer of 2 to 4 and, when k' is 2 to 4, $X_I'$'s may be different, and $r_I$ is a C1-C4 alkyl group, a C2-C4 alkenyl group or a C2-C4 alkynyl group], and a inert carrier;

8. A 2H-pyran-2-one compound represented by the formula (VIII):

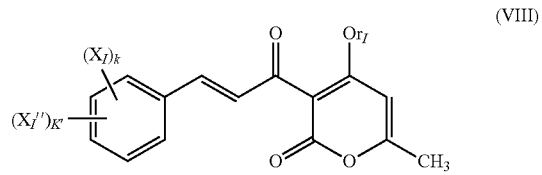

[wherein $X_I$ represents a C2-C4 alkenyl group, a C2-C4 alkynyl group, a $R_I$—S(O)$_l$-group ($R_I$ represents a C1-C4 alkyl group, and l represents an integer of 0 to 2), a cyano group, a carboxy group, a C1-C4 alkoxycarbonyl group, a $(R_I)_2$N-group ($R_I$ is as defined above), a $R_I$—CO—NH-group ($R_I$ is as defined above), a $R_I$O—CO—NH-group ($R_I$ is as defined above), a $R_I$NH—CO—NH-group ($R_I$ is as defined above) or $(R_I')_2$N—CO-group ($R_I'$ represents a hydrogen atom or a C1-C4 alkyl group), $X_I''$ represents a halogen atom, or a C1-C4 alkyl group optionally substituted with a halogen atom or a C1-C4 alkoxy group, or a nitro group, or a C2-C4 alkoxy group, or a RB-group (B represents an oxygen atom or a sulfur atom, and R represents a C1-C4 alkyl group substituted with a halogen atom), k represents 0 or 1, k' represents an integer of 0 to 4, when k is 0, k' is an integer of 2 to 4 and, when k' is 2 to 4, $X_I'''$'s may be different, and $r_I$ is a C1-C4 alkyl group, a C2-C4 alkenyl group or a C2-C4 alkynyl group];

9. A 2H-pyran-2-one compound represented by the formula (IX):

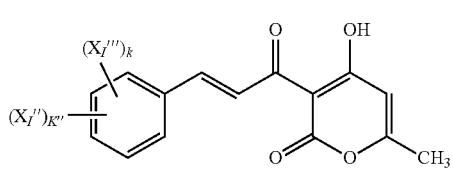

(wherein $X_I'''$ represents a C2-C4 alkenyl group, a C2-C4 alkynyl group, a carboxy group, a C2-C4 alkoxycarbonyl group or a $(R_{II})_2N$-group ($R_{II}$ represents a C2-C4 alkyl group), $X_I''$ represents a halogen atom, or a C1-C4 alkyl group optionally substituted with a halogen atom or a C1-C4 alkoxy group, or a nitro group, or a C2-C4 alkoxy group, or a RB-group (B represents an oxygen atom or a sulfur atom, and R represents a C1-C4 alkyl group substituted with a halogen atom), k represents 0 or 1, k" represents an integer of 0 to 2, when k is 0, k" is 2 and, when k" is 2, X"'s are different];

10. A I type collagen gene transcription suppressing composition, which comprises a 2H-1-benzopyran-2-one compound represented by the formula (X):

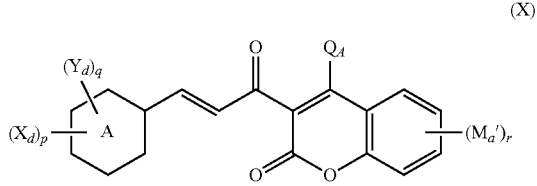

[wherein
I. A represents a benzene ring or a pyridine ring;
II. In $(X_d)_p$, $X_d$ is a substituent on a carbon atom, and represents a methoxy group or an ethoxy group, p represents 0, 1, 2, 3 or 4 and, when p is 2 or more, $X_d$'s are the same or different;
III. In $(Y_d)_q$, $Y_d$ is a substituent on a carbon atom, and represents a substituent of the following $X_4$ group or $Y_4$ group, q represents 0, 1, 2, 3, 4 or 5, when q is 2 or more, $Y_d$'s are the same or different and, q is 2 or more, the adjacent two same or different $Y_d$'s constitute a group of a $Z_4$ group, and may be fused with an A ring;
(1) a $X_4$ group:
a $M_a$-group [$M_a$ represents a $R_b$-group ($R_b$ represents a C1-C10 alkyl group optionally substituted with a halogen atom), a halogen, atom, a nitro group, a cyano group, a hydroxyl group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HO$R_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_e$O—CO—$R_d$-group ($R_e$ and $R_d$ are as defined above), a HO—CO—CH=CH-group, a $R_eR_e'$N—$R_d$-group ($R_e$ and $R_e'$ are the same or different, $R_e$ is as defined above, $R_e'$ has the same meaning as that of $R_e$, and $R_d$ is as defined above), a $R_e$—CO—$NR_e'$—$R_d$-group ($R_e$, $R_e'$ and $R_d$ are as defined above), a $R_bO$—CO—$N(R_e)$—$R_d$-group ($R_b$, $R_e$ and $R_d$ are as defined above), a $R_eR_e'N$—CO—$R_d$-group ($R_e$, $R_e'$ and $R_d$ are as defined above), a $R_eR_e'N$—CO—$NR_e''$—$R_d$-group ($R_e$, $R_e'$ and $R_e''$ are the same or different, $R_e$ and $R_e'$ are as defined above, $R_e''$ has the same meaning as that of $R_e$, and $R_d$ is as defined above), a $R_eR_e'N$—C(=$NR_e''$)—$NR_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—$SO_2$—$NR_e$—$R_d$-group ($R_b$, $R_e$ and $R_d$ are as defined above), a $R_eR_e'N$—$SO_2$—$R_d$-group ($R_e$, $R_e'$ and $R_d$ are as defined above), a C2-C10 alkenyl group or a C2-C10 alkynyl group], provided that when A represents a benzene ring, then a methoxy group and an ethoxy group are excluded;
(2) a $Y_4$ group:
a $M_b$-$R_d$-group [$M_b$ represents a $M_c$-group {$M_c$ represents a $M_d$-$R_d'$-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

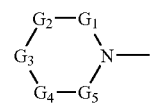

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —$NR_1$-group {$R_1$ represents a hydrogen atom, or a C1-C10 alkyl group, or a C2-C10 alkyl group optionally substituted with a halogen atom or a $R_2$—$B_1$-group ($R_2$ represents a C1-C10 alkyl group, a C3-C10 alkenyl group or C3-C10 alkynyl group, and $B_1$ represents an oxy group, a thio group, a sulfinyl group or a sulfonyl group), or a C3-C10 alkenyl group, or a C3-C10 alkynyl group} or a C2-C10 alkenylene group optionally substituted with a methyl group, an oxy group, a thio group, a sulfinyl group, a sulfonyl group or a —$NR_1$-group ($R_1$ is as defined above)},

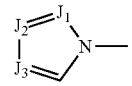

a (c)-group (in (c), $J_1$, $J_2$ and $J_3$ are the same or different, and represent a methine group optionally substituted with a methyl group, or a nitrogen atom),

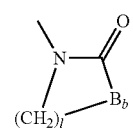

a (d)-group (l is 2, 3 or 4, and $B_b$ represents an oxy group or a thio group)

or

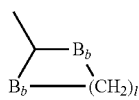
(e)

an (e)-group (l and $B_b$ are as defined above), $R_d'$ is the same as or different from $R_d$, and has the same meaning as that of $R_d$}}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_c R_e$N-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_c R_e$N—CO-group ($M_c$ and $R_e$ are as defined above), a $M_c R_e$N—CO—$NR_e'$-group ($M_c$, $R_e$ and $R_e'$ are as defined above), a $M_c R_e$N—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_c R_e$N—$SO_2$-group ($M_c$ and $R_e$ are as defined above), and $R_d$ is as defined above];
(3) a $Z_4$ group:
a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$—$Y_b''$-group ($Y_b$ and $Y_b''$ are the same or different, a methylene group, or an oxy group, or a thio group, or a sulfinyl group, or an imino group optionally substituted with a C1-C10 alkyl group, and $Y_b'$ represents a C1-C4 alkylene group optionally substituted with a halogen atom, or a C1-C4 alkylene group optionally having an oxo group) or a —$Y_c$—O—$Y_c'$—O-group ($Y_c$ and $Y_c'$ are the same or different, and represent a C1-C10 alkylene group);
IV. $Q_A$ represents a hydroxyl group, a (b) group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, and $B_c$ represents an oxy group or a —N(($O)_m R_1$)-group (m represents 0 or 1, and $R_1$ is as defined above), provided that when $A_9$ is a hydrogen atom, then $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1 R_1'$N—$SO_2$—$B_c$-group ($R_1$ is as defined above, $R_1'$ is the same as or different from $R_1$, and has the same meaning as that of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above) or a $M_c$-$B_c$-group ($M_c$ and $B_c$ are as defined above);
(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1 R_1'$N-group ($R_1$ and $R_1'$ are as defined above), and $R_4$ is as defined above} or an $A_2$-CO—$R_4$-group ($A_2$ represents a substituent of the following $A_2$ group, and $R_4$ is as defined above);
(2) an $A_8$ group: a hydrogen atom, or a C1-C10 alkyl group optionally substituted with a halogen atom;
(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as define above, and $R_4'$ represents a C2-C4 alkylene group), a $D_4$-$R_4'$-group ($D_4$ and $R_4'$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $D_3$-$R_4'$-group ($D_3$ and $R_4'$ are as defined above) or an $A_2$-CO—$R_4$-group ($A_2$ and $R_4$ are as defined above);
(4) an $A_8'$ group: a C1-C10 alkyl group or a C2-C10 haloalkyl group;
(5) an $A_7''$ group: a C2-C10 alkenyl group, a C3-C10 alkenyl group substituted with a halogen atom, a C3-C10 alkynyl group optionally substituted with a halogen atom, a $R_2$—$B_1$—$R_4'$-group ($R_2$, $B_1$ and $R_4'$ are as defined above), a $D_4$-$R_4'$-group ($D_4$ and $R_4'$ are as defined above), a $D_5$-$R_4$-group ($D_5$ and $R_4$ are as defined above), a $D_1$-$R_4'$-group ($D_1$ and $D_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);
(i) a $D_4$ group: a hydroxy group or an $A_1$-O-group [$A_1$ represents a $R_3$—(CHR$_0$)$_m$—($B_2$—$B_3$)$_m'$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —N((O)$_m R_1'$)-group ($R_1'$ is as defined above, and n represents 0 or 1), $B_3$ is as defined above, m' represents 0 or 1 and, when $B_3$ is a sulfonyl group, then m is 0, and $R_3$ is not a hydrogen atom}];
(ii) a $D_5$ group: an O=C($R_3$)-group ($R_3$ is as defined above), an $A_1$-(O)$_n$—N=C($R_3$)-group ($A_1$, n and $R_3$ are as defined above), a $R_1$—$B_0$—CO—$R_4$—(O)$_n$—N=C($R_3$)-group [$R_1$, $R_4$, n and $R_3$ are as defined above, and $B_0$ represents an oxy group, a thio group or a —N((O)$_m R_1'$)-group ($R_1'$ and m are as defined above)], a $D_2$-$R_4$—(O)$_n$—N=C($R_3$)-group ($D_2$, $R_4$, n and $R_3$ are as defined above) or a $R_1 A_1$N—N=C($R_3$)-group ($R_1$, $A_1$ and $R_3$ are as defined above);
(iii) a $D_1$ group: a ($R_1$—(O)$_k$)-$A_1$N—(O)$_{k'}$-group ($R_1$ and $A_1$ are as defined above, and k and k' are the same or different, and represent 0 or 1);
(iv) a $D_2$ group: a cyano group, a $R_1 R_1'$NC(=N—(O)$_n$-$A_1$)-group ($R_1$, $R_1'$, n and $A_1$ are as defined above), an $A_1$N=C(—$OR_2$)-group ($A_1$ and $R_2$ are as defined above) or a $NH_2$—CS-group;

(v) a $D_3$ group: a nitro group or a $R_1OSO_2$-group ($R_1$ is as defined above);

(vi) an $A_2$ group:

1) an $A_3$-$B_4$-group

[$A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_a$—$(R_4)_m$-group ($R_a$ represents a phenyl group, a pyridinyl group, a furyl group or a thienyl group, optionally substituted with a halogen atom, a C1-C10 alkyl group, a C1-C10 alkoxy group or a nitro group, and $R_4$ and m are as defined above), or a C1-C10 alkyl group substituted with a (b)-$R_4$-group ((b) and $R_4$ are as defined above), a (c)-$R_4$-group ((c) and $R_4$ are as defined above), a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $A_4$-$SO_2$—$R_4$-group {$A_4$ is as defined above, and $R_4$ is as defined above}, $B_4$ represents an oxy group, a thio group or a —$N((O)_mR_1)$-group ($R_1$ and m are as defined above), provided that when $B_4$ is a thio group, then $A_3$ is not a hydrogen atom];

2) a $R_1$—$B_4$—CO—$R_4$—$B_4'$-group ($R_1$, $B_4$ and $R_4$ are as defined above, $B_4'$ is the same as or different from $B_4$, and has the same meaning as that of $B_4$, provided that when $B_4$ is a thio group, then $R_2$ is not a hydrogen atom) or a $D_2$-$R_4$—$B_4$-group ($D_2$, $R_4$ and $B_4$ are as defined above);

3) a $R_2$—$SO_2$—$NR_1$-group ($R_2$ is as defined above, provided that a hydrogen atom is excluded, and $R_1$ is as defined above), 4) a (b)-group ((b) is as defined above);

5) a (c)-group ((c) is as defined above) or 6) a $R_1A_1N$—$NR_1'$-group ($R_1$, $A_1$ and $R_1'$ are as defined above);

V. $M_a'$ is the same as or different from $M_a$, and has the same meaning as that of $M_a$, and r represents 0, 1, 2, 3 or 4, provided that when an A ring is a benzene ring, in case that q and r are 0, then p is 2, 2, 3 or 4; and the "as defined above" in the same symbol between a plurality of substituent indicates that the plurality of the substituents independently represent the same meaning as that of described above and, between the plurality of substituents, a selection range of the selected substituents is the same, while the selected substituents may be the same or different as far as they are selected in the range]; and an inert carrier;

11. A 2H-1-benzopyran-2-one compound represented by the formula (XI):

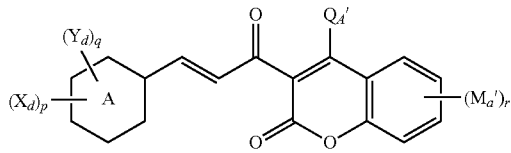

(XI)

[wherein

I. A represents a benzene ring or a pyridine ring;

II. In $(X_d)_p$, $X_d$ is a substituent on a carbon atom, and represents a methoxy group or an ethoxy group, p represents 0, 1, 2, 3 or 4 and, when p is 2 or more, $X_d$'s are the same or different;

III. In $(Y_d)_q$, $Y_d$ is a substituent on a carbon atom, and represents a substituent of the following $X_4$ group or $Y_4$ group, q represents 0, 1, 2, 3, 4 or 5, when q is 2 or more, $Y_d$'s are the same or different and, when q is 2 or more, the adjacent two same or different $Y_d$'s constitute a group of a $Z_4$ group, and may be fused with an A ring;

(1) a $X_4$ group:

a $M_a$-group [$M_a$ represents a $R_b$-group ($R_b$ represents a C1-C10 alkyl group optionally substituted with a halogen atom), a halogen atom, a nitro group, a cyano group, a hydroxy group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_eO$—CO—$R_d$-group ($R_e$ and $R_d$ are as defined above), a HO—CO—CH=CH-group, a $R_eR_e'N$—$R_d$-group ($R_e$ and $R_e'$ are the same or different, $R_e$ is as defined above, $R_e'$ has the same meaning as that of $R_e$, and $R_d$ is as defined above), a $R_e$—CO—$NR_e'$—$R_d$-group ($R_e$, $R_e'$ and $R_d$ are as defined above), a $R_bO$—CO—$N(R_e)$—$R_d$-group ($R_b$, $R_e$ and $R_d$ are as defined above), a $R_eR_e'N$—CO—$R_d$-group ($R_e$, $R_e'$ and $R_d$ are as defined above), a $R_eR_e'N$—CO—$NR_e''$—$R_d$-group ($R_e$, $R_e'$ and $R_e''$ are the same or different, $R_e$ and $R_e'$ are as defined above, $R_e''$ has the same meaning as that of $R_e$, and $R_d$ is as defined above), a $R_eR_e'N$—C(=$NR_e''$)—$NR_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—$SO_2$—$NR_e$—$R_d$-group ($R_b$, $R_e$ and $R_d$ are as defined above), a $R_eR_e'N$—$SO_2$—$R_d$-group ($R_e$, $R_e'$ and $R_d$ are as defined above), a C2-C10 alkenyl group or a C2-C10 alkynyl group], provided that when A represents a benzene ring, then a methoxy group and an ethoxy group are excluded;

(2) $Y_4$ group:

a $M_b$-$R_d$-group [$M_b$ represents a $M_c$-group {$M_c$ represents a $M_d$-$R_d'$-group {$M_d$ represents a phenyl group optionally substituted with a $M_a$-group ($M_a$ is as defined above), a pyridyl group optionally substituted with a $M_a$-group ($M_a$ is as defined above), or a naphthyl group optionally substituted with a $M_a$-group ($M_a$ is as defined above), or

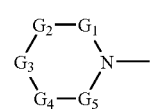

(b)

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —$NR_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, sulfinyl group or a sulfonyl group), or a C3-C10 alkenyl group, or a C3-C10 alkynyl group}, or a C2-C10 alkenylene group optionally substituted with a methyl group, an oxy group, a thio group, a sulfinyl group, a sulfonyl group or a —$NR_1$-group ($R_1$ is as defined above)},

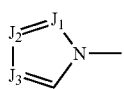

(c)

a (c)-group (in (c), $J_1$, $J_2$, and $J_3$ are the same or different and, represent a methine group optionally substituted with a methyl group, or a nitrogen atom),

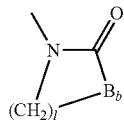

(d)

a (d)-group (l is 2, 3 or 4, and $B_b$ represents an oxy group or a thio group) or

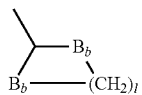

(e)

an (e)-group (l and $B_b$ are as defined above), $R_d'$ is the same as or different from $R_d$, and has the same meaning as that of $R_d$}}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_eN$-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_cR_eN$—CO-group ($M_c$ and $R_e$ are as defined above), a $M_cR_eN$—CO—$NR_e'$-group ($M_c$, $R_e$ and $R_e'$ are as defined above), a $M_cR_eN$—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_cR_eN$—$SO_2$-group ($M_c$ and $R_e$ are as defined above), and $R_d$ is as defined above];
(3) a $Z_4$ group:
a —N=C($Y_a$)—$Y_a'$-group ($Y_a$ represents a hydrogen atom, or C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$-$Y_b''$-group ($Y_b$ and $Y_b'$ are the same or different, and represent a methylene group, or an oxy group, or a thio group, or a sulfinyl group, or an imino group optionally substituted with a C1-C10 alkyl group, $Y_b'$ represents a C1-C4 alkylene group optionally substituted with a halogen atom, or a C1-C4 alkylene group optionally having an oxo group) or a —$Y_c$—O—$Y_c'$—O-group ($Y_c$ and $Y_c'$ are the same or different, and a C1-C10 alkylene group);
IV. $Q_4'$ represents a (b)-group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, $B_c$ represents an oxy group or a —N((O)$_m R_1$)-group (m represents 0 or 1, and $R_1$ is as defined above), provided that when $A_9$ is a hydrogen atom, then $B_c$ is not a sulfonyl group], an $A_7''$-$SO_2$—$B_c$-group ($A_7''$ represents a substituent of the following $A_7$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1R_1'$N—$SO_2$—$B_c$-group ($R_1$ is as defined above, $R_1'$ is the same as or different from $R_1$, and has the same meaning as that of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above) or a $M_c$-$B_c$-group ($M_c$ and $B_c$ are as defined above);
(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1R_1'$N-group ($R_1$ and $R_1'$ are as defined above), and $R_4$ is as defined above} or an $A_2$-CO—$R_4$-group ($A_2$ represents a substituent of the following $A_2$ group, and $R_4$ is as defined above);
(2) an $A_8$ group: a hydrogen atom, or C1-C10 alkyl group optionally substituted with a halogen atom;
(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$ group ($D_4$ and $R_4'$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4'$-group ($D_2$ and $R_4'$ are as defined above), a $D_3$-$R_4'$-group ($D_3$ and $R_4'$ are as defined above) or an $A_2$-CO—$R_4$-group ($A_2$ and $R_4$ are as defined above);
(4) an $A_9'$ group: a C1-C10 alkyl group or a C2-C10 haloalkyl group;
(5) an $A_7''$ group: a C2-C10 alkenyl group, a C3-C10 alkenyl group substituted with a halogen atom, a C3-C10 alkynyl group optionally substituted with a halogen atom, a $R_2$—$B_1$—$R_4'$-group ($R_2$, $B_1$ and $R_4'$ are as defined above), a $D_4$-$R_4'$-group ($D_4$ and $R_4'$ are as defined above), a $D_5$-$R_4'$-group ($D_5$ and $R_4'$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);
(i) a $D_4$ group: a hydoxy group or an $A_1$-O-group [$A_1$ represents a $R_3$—(CH$R_0$)$_m$—($B_2$—$B_3$)$_m'$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —N(($O)_n R_1'$)-group ($R_1'$ is as defined above, and n represents 0 or 1), $B_3$ is as defined above, m' represents 0 or 1 and, when $B_3$ is a sulfonyl group, then m is 0, and $R_3$ is not a hydrogen atom}];

(ii) a $D_5$ group: an O=C($R_3$)-group ($R_3$ is as defined above), an $A_1$-$(O)_n$—N=C($R_3$)-group ($A_1$, n and $R_3$ are as defined above), a $R_1$—$B_0$—CO—$R_4$—$(O)_n$—N=C($R_3$)-group [$R_1$, $R_4$, n and $R_3$ are as defined above, and $B_0$ represents an oxy group, a thio group or a —N(($O)_m R_1'$)-group ($R_1'$ and m are as defined above)], a $D_2$-$R_4$—$(O)_n$—N=C($R_3$)-group ($D_2$, $R_4$, n and $R_3$ are as defined above) or a $R_1 A_1$N—N=C($R_3$)-group ($R_1$, $A_1$ and $R_3$ are as defined above);

(iii) a $D_1$ group: a $(R)$—$(O)_k$)$A_1$N—$(O)_{k'}$-group ($R_1$ and $A_1$ are as defined above, and k and k' are the same or different, and represent 0 or 1);

(iv) a $D_2$ group: a cyano group, a $R_1 R_1'$NC(=N—$(O)_n$-$A_1$)-group ($R_1$, $R_1'$, n and $A_1$ are as defined above), an $A_1$N=C—($OR_2$)-group ($A_1$ and $R_2$ are as defined above) or a $NH_2$—CS-group;

(v) a $D_3$ group: a nitro group or a $R_1 OSO_2$-group ($R_1$ is as defined above);

(vi) an $A_2$ group:

1) an $A_3$-$B_4$-group

[$A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_a$—$(R_4)_m$-group ($R_a$ represents a phenyl group, a pyridyl group, a furyl group or a thienyl group, optionally substituted with a halogen atom, a C1-C10 alkyl group, a C1-C10 alkoxy group or a nitro group, and $R_4$ and m are as defined above), or a C1-C10 alkyl group substituted with a (b)-$R_4$-group ((b) and $R_4$ are as defined above), a (c)-$R_4$-group ((c) and $R_4$ are as defined above), a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $A_4$-$SO_2$—$R_4$-group {$A_4$ is as defined above, and $R_4$ is as defined above}, $B_4$ represents an oxy group, a thio group or a —N(($O)_m R_1$)-group ($R_1$ and m are as defined above), provided that when $B_4$ is a thio group, $A_3$ is not a hydrogen atom];

2) a $R_1$—$B_4$—CO—$R_4$—$B_4'$-group ($R_1$, $B_4$ and $R_4$ are as defined above, $B_4'$ is the same as or different from $B_4$, and has the same meaning as that of $B_4$, provided that when $B_4$ is a thio group, $R_2$ is not a hydrogen atom), or a $D_2$-$R_4$—$B_4$-group ($D_2$, $R_4$ and $B_4$ are as defined above);

3) a $R_2$—$SO_2$—$NR_1$-group ($R_2$ is as defined above, provided that a hydrogen atom is excluded, and $R_1$ is as defined above);

4) a (b)-group ((b) is as defined above);

5) a (c)-group ((c) is as defined above) or 6) a $R_1 A_1$N—$NR_1'$-group ($R_1$, $A_1$ and $R_1'$ are as defined above);

V. $M_a'$ is the same as or different from $M_a$, and has the same meaning as that of $M_a$, and r represents 0, 1, 2, 3 or 4, provided that when an A ring is a benzene ring, in case that q is 0, then p is 2, 3 or 4; and the "as defined above" between a plurality of substituents indicates that the plurality of substituents independently represent the same meaning as that described above and, between the plurality of substituents, a selection range of selected substituents is the same, while the selected substituents may be the same or different as far as they are selected in the range];

12. A 2H-1-benzopyran-2-one compound represented by the formula (XII):

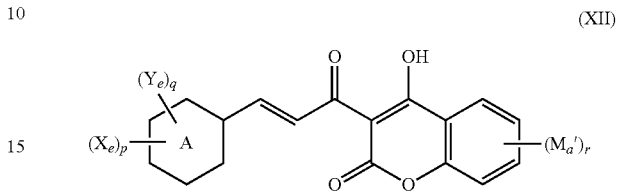

(XII)

[wherein

I. A represents a benzene ring or a pyridine ring;

II. In $(X_e)_p$, $X_e$ represents a hydroxy group, a halogen atom, a C1-C10 alkyl group, a R'—S(O)l- group (R' represents a C1-C10 alkyl group, and l represents 0, 1 or 2), a cyano group, a HOCO—CH=CH-group, a $(R')_2$N-group (R' is as defined above), a R'CO—NH-group (R' is as defined above), a nitro group or a C1-C10 alkoxy group, p represents 0, 1, 2, 3 or 4 and, when p is 2 or more, $X_d$'s are the same or different;

III. In $(Y_e)_q$, $Y_e$ is a substituent on a carbon atom, and represents a substituent of the following $X_5$ group or $Y_5$ group, q represents 0, 1, 2, 3, 4 or 5, when q is 2 or more, $Y_e$'s are the same or different and, when q is 2 or more, the adjacent two same or different $Y_e$'s constitute a group of a $Z_5$ group, and may be fused with an A ring;

(1) a $X_5$ group:

a $M_a$-group [$M_a$ represents a $R_b$-group ($R_b$ represents a C1-C10 alkyl group optionally substituted with a halogen atom), a halogen atom, a nitro group, a cyano group, a hydroxyl group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_d$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_e$O—CO—$R_d$-group ($R_e$ and $R_d$ are as defined above), a HO—CO—CH=CH-group, a $R_e R_e'$N—$R_d$-group ($R_e$ and $R_e'$ are the same or different, $R_e$ is as defined above, $R_e'$ has the same meaning as that of $R_e$, and $R_d$ is as defined above), a $R_e$—CO—$NR_e'$—$R_d$-group ($R_e$, $R_e'$ and $R_d$ are as defined above), a $R_b$O—CO—N($R_e$)—$R_d$-group ($R_b$, $R_e$ and $R_d$ are as defined above), a $R_e R_e'$N—CO—$R_d$-group ($R_e$, $R_e'$ and $R_d$ are as defined above), a $R_e R_e'$N—CO—$NR_e''$—$R_d$-group ($R_e$, $R_e'$ and $R_e''$ are the same or different, $R_e$ and $R_e''$ are as defined above, $R_e''$ has the same meaning as that of $R_e$, and $R_d$ is as defined above), a $R_e R_e'$N—C(=$NR_e''$)—$NR_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—$SO_2$—$NR_e$—$R_d$-group ($R_b$, $R_e$ and $R_d$ are as defined above), a $R_e R_e'$N—$SO_2$—$R_d$-group ($R_e$, $R_e'$ and $R_d$ are as defined above), a C2-C10 alkenyl group or a C2-C10 alkynyl group], provided that when A represents a benzene ring, then a $X_e$-group ($X_e$ is as defined above) is excluded;

(2) a $Y_5$ group:

a $M_b$-$R_d$-group [$M_b$ represents a $M_c$-group {$M_c$ represents a $M_d$-$R_d$'-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

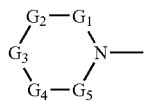
(b)

a (b)-group [in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —$NR_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group or a C3-C10 alkynyl group}, or a C2-C10 alkenylene group optionally substituted with a methyl group, an oxy group, a thio group, a sulfinyl group, a sulfonyl group or a —$NR_1$-group ($R_1$ is as defined above)},

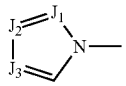
(c)

a (c)-group (in (c), $J_1$, $J_2$ and $J_3$ are the same or different, and represent a methine group optionally substituted with a methyl group, or a nitrogen atom),

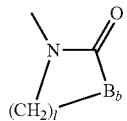
(d)

a (d)-group (l is 2, 3 or 4, and $B_b$ represents an oxy group or a thio group) or

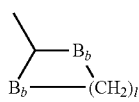
(e)

an (e)-group (l and $B_b$ are as defined above), $R_d$' is the same as or different from $R_d$, and has the same meaning as that of $R_d$]}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_c$R_e$N-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_c$R_e$N—CO-group ($M_c$ and $R_e$ are as defined above), a $M_c$R_e$N—CO—$NR_e$'-group ($M_c$, $R_e$ and $R_e$' are as defined above), a $M_c$R_e$N—C(=$NR_e$')—$NR_e$-group ($M_c$, $R_e$, $R_e$' and $R_e$" are as defined above), a $M_c$-$SO_2$—$NR_e$-group ($M_c$ and $R_e$ are as defined above) or a $M_c$R_e$N—$SO_2$-group ($M_c$ and $R_e$ are as defined above), and $R_d$ is as defined above];

(3) a $Z_5$ group:

a —N=C($Y_a$)—$Y_a$'-group ($Y_a$ represents a hydrogen atom, or a C1-C10 alkyl group optionally substituted with a halogen atom, or a C1-C10 alkoxy group, and $Y_a$' represents an oxy group, or a thio group, or an imino group optionally substituted with a C1-C10 alkyl group), a —$Y_b$—$Y_b$'—$Y_b$"-group ($Y_b$ and $Y_b$" are the same or different, and represent a methylene group, or an oxy group, or a thio group, or a sulfinyl group, or an imino group optionally substituted with a C1-C10 alkyl group, and $Y_b$' represents a C1-C4 alkylene group optionally substituted with a halogen atom, or a C1-C4 alkylene group optionally having an oxo group) or a —$Y_c$—O—$Y_c$'—O-group ($Y_c$ and $Y_c$' are the same or different, and represent a C1-C10 alkylene group), provided that when p is 0, then $Y_e$ is not fused with an A ring to form a benzo[1,3]dioxol ring;

IV. $M_a$' is the same as or different from $M_a$, and has the same meaning as that of $M_a$, and r represents 0, 1, 2, 3 or 4, provided that when an A ring is a benzene ring, then q is not 0; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range];

13. A 2H-1-benzopyran-2-one compound represented by the formula (XIII):

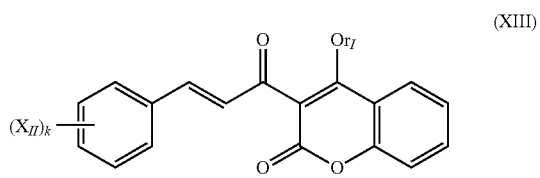
(XIII)

[wherein XII represents a hydrogen atom, or a hydroxyl group, or a halogen atom, or a C1-C4 alkyl group optionally substituted with a halogen atom or a C1-C4 alkoxy group, or a C2-C4 alkenyl group, or a C2-C4 alkynyl group, or a C3-C4 alkoxy group, or a $R_I$—S(O)$_l$-group ($R_I$ represents a C1-C4 alkyl group, and l represents an integer of 0 to 2), or a nitro group, or a cyano group, or a carboxy group, or a C1-C4 alkoxycarbonyl group, or a ($R_I$)$_2$N-group ($R_I$ is as defined above), or a $R_I$—CO—$N_I$-group ($R_I$ is as defined above), or a $R_I$O—CO—NH-group ($R_I$ is as defined above), or a $R_I$NH—CO—NH-group ($R_I$ is as defined above), or a ($R_I$')$_2$N—CO-group ($R_I$' represents a hydrogen atom or a C1-C4 alkyl group), or a RB-group (B represents an oxygen atom or a sulfur atom, and R represents a C1-C4 alkyl group substituted with a halogen atom), k represents an integer of 1 to 4 and, when k is an integer of 2 to 4, $X_{II}$'s may be different, and $r_I$ represents a C1-C4 alkyl group, a C2-C4 alkenyl group or a C2-C4 alkynyl group];

14. A 2H-1-benzopyran-2-one compound represented by the formula (XIV):

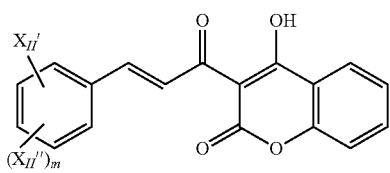

(XIV)

[wherein $X_{II}'$ represents a C1-C4 alkyl group substituted with a halogen atom or a C1-C4 alkoxy group, a C2-C4 alkenyl group, a C2-C4 alkynyl group, a C3-C4 alkoxy group, a $R_I$—S(O)$_l$-group ($R_{II}$ represents a C2-C4 alkyl group, and l represents an integer of 0 to 2), a cyano group, a carboxy group, a C1-C4 alkoxycarbonyl group, a $(R_{II})_2$N-group ($R_{II}$ is as defined above), a $R_I$—CO—NH-group ($R_I$ represents a C1-C4 alkyl group), a $R_I$O—CO—NH-group ($R_I$ is as defined above), a $R_I$NH—CO—NH-group ($R_I$ is as defined above), a $(R_I')_2$N—CO-group ($R_I'$ represents a hydrogen atom or a C1-C4 alkyl group) or a RB-group (B represents an oxygen atom or a sulfur atom, and R represents a C1-C4 alkyl group substituted with a halogen atom), $X_{II}''$ represents a hydrogen atom, a halogen atom, a C1-C4 alkyl group or a C3-C4 alkoxy group, m represents 1 or 2 and, when m is 2, $X_{II}''$'s may be different];

15. A I type collagen gene transcription suppressing composition, which comprises a 2(1H)-pyridinone compound represented by the formula (XV):

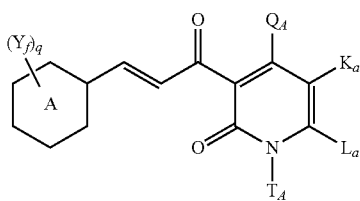

(XV)

[wherein
I. A represents a benzene ring or a pyridine ring;
II. In $(Y_f)_q$, $Y_f$ is a substituent on a carbon atom, and represents a group of the following X group or Y group, q represents 0, 1, 2, 3, 4 or 5, when q is 2 or more, $Y_f$'s are the same or different and, when q is 2 or more, the adjacent two same or different $Y_f$'s constitutes a group of a Z group, and may be fused with an A ring;
(1) a X group:
a $M_a$-group [$M_a$ represents a $R_b$-group ($R_b$ represents a C1-C10 alkyl group optionally substituted with a halogen atom), a halogen atom, a nitro group, a cyano group, a hydroxy group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—R$_d$-group ($R_e$ represents a hydrogen atom, or a C1-C10 alkyl group optionally substituted with a halogen atom, and $R_d$ is as defined above), a $R_e$—CO—O—R$_d$-group ($R_e$ and $R_d$ are as defined above), a $R_e$O—CO—R$_d$-group ($R_e$ and $R_d$ are as defined above), a HO—CO—CH=CH-group, a $R_eR_e'$N—R$_d$-group ($R_e$ and $R_e'$ are the same or different, $R_e$ is as defined above, $R_e'$ has the same meaning as that of $R_e$, and $R_d$ is as defined above), a $R_e$—CO—NR$_e'$—R$_d$-group ($R_e$, $R_e'$ and $R_d$ are as defined above), a $R_b$O—CO—N($R_e$)—R$_d$-group ($R_b$, $R_e$ and $R_d$ are as defined above), a $R_eR_e'$N—CO—R$_d$-group ($R_e$, $R_e'$ and $R_d$ are as defined above), a $R_eR_e'$N—CO—NR$_e''$—R$_d$-group ($R_e$, $R_e'$ and $R_e''$ are the same or different, $R_e$ and $R_e'$ are as defined above, $R_e'''$ has the same meaning as that of $R_e$, and $R_d$ is as defined above), a $R_eR_e'$N—C(=NR$_e''$)—NR$_e'''$—R$_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—SO$_2$—NR$_e$—R$_d$-group ($R_b$, $R_e$ and $R_d$ are as defined above), a $R_eR_e'$N—SO$_2$—R$_d$-group ($R_e$, $R_e'$ and $R_d$ are as defined above), a C2-C10 alkenyl group or a C2-C10 alkynyl group];

(2) a Y group:
a $M_b$-$R_d$-group [$M_b$ represents a $M_c$-group {$M_c$ represents a $M_d$-$R_d'$-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

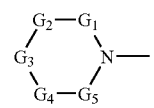

(b)

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —NR$_1$-group {$R_1$ represents a hydrogen atom, or a C1-C10 alkyl group, or a C2-C10 alkyl group substituted with a halogen atom or a $R_2$—B$_1$-group ($R_2$ represents a C1-C10 alkyl group, a C3-C10 alkenyl group or a C3-C10 alkynyl group, and B$_1$ represents an oxy group, a is thio group, a sulfinyl group or a sulfonyl group), or a C3-C10 alkenyl group, or a C3-C10 alkynyl group}, or a C2-C10 alkenylene group optionally substituted with a methyl group, an oxy group, a thio group, a sulfinyl group, a sulfonyl group or a —NR$_1$-group ($R_1$ is as defined above)},

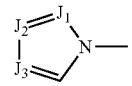

(c)

a (c)-group (in (c), $J_1$, $J_2$ and $J_3$ are the same or different, and represent a methine group optionally substituted with a methyl group, or a nitrogen atom),

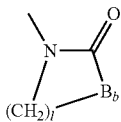

(d)

a (d)-group (l is 2, 3 or 4, and $B_b$ represents an oxy group or a thio group) or

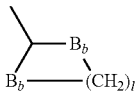

(e)

an (e)-group (l and $B_b$ are as defined above], $R_d'$ is the same as or different from $R_d$, and has the same meaning as that of $R_d$}}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_c R_e$N-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_c R_e$N—CO-group ($M_c$ and $R_e$ are as defined above), a $M_c R_e$N—CO—$NR_e'$-group ($M_c$, $R_e$ and $R_e'$ are as defined above), a $M_c R_e$N—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_c R_e$N—$SO_2$-group ($M_c$ and $R_e$ are as defined above), and $R_d$ is as defined above];
(3) a Z group: a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an imino group optionally substituted with an oxy group, or a thio group, or a C1-C10 alkyl group), a —$Y_b$—$Y_b'$—$Y_b''$-group ($Y_b$ and $Y_b''$ are the same or different, and represent a methylene group, or an oxy group, or a thio group, or a sulfinyl group, or an imino group optionally substituted with a C1-C10 alkyl group, and $Y_b'$ represents a C1-C4alkylene group optionally substituted with a halogen atom, or a C1-C4alkylene group optionally having an oxo group), or a —$Y_c$—O—$Y_c'$—O-group ($Y_c$ and $Y_c'$ are the same or different, and represent a C1-C10 alkylene group);
III. $Q_A$ represents a hydroxyl group, a (b)-group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, and $B_c$ represents an oxy group or a —N(($O)_m R_1$)-group (m represents 0 or 1, and $R_1$ is as defined above), provided that when $A_9$ is a hydrogen atom, then $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1 R_1'$N—$SO_2$—$B_c$ group ($R_1$ is as defined above, $R_1'$ is the same as or different of $R_1$, and has the same meaning of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or a $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above) or a $M_c$-$B_c$-group ($M_c$ and $B_c$ are as defined above);
(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1 R_1'$N-group ($R_1$ and $R_1'$ are as defined above), and $R_4$ is as defined above} or an $A_2$-CO—$R_4$-group ($A_2$ represents a substituent of the following $A_2$ group, and $R_4$ is as defined above);
(2) an $A_8$ group: a hydrogen atom, or a C1-C10 alkyl group optionally substituted with a halogen atom;
(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$-group ($D_4$ and $R_4'$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $D_3$-$R_4'$-group ($D_3$ and $R_4'$ are as defined above) or an $A_2$-CO—$R_4$-group ($A_2$ and $R_4$ are as defined above);
(4) an $A_8'$ group: a C1-C10 alkyl group or a 2-C10 haloalkyl group;
(5) an $A_7''$ group: a C2-C10 alkenyl group, a C3-C10 alkenyl group substituted with a halogen atom, a C3-C10 alkynyl group optionally substituted with a halogen atom, a $R_2$—$B_1$—$R_4'$-group ($R_2$, $B_1$ and $R_4'$ are as defined above), a $D_4$-$R_4'$-group ($D_4$ and $R_4'$ are as defined above), a $D_5$-$R_4$-group ($D_5$ and $R_4$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);
(i) a $D_4$ group: a hydroxy group or an $A_1$-O-group [$A_1$ represents a $R_3$—(CH$R_0$)$_m$—($B_2$—$B_3$)$_{m'}$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —N(($O)_n R_1'$)-group ($R_1'$ is as defined above, and n represents 0 or 1), $B_3$ is as defined above, m' represents 0 or 1 and, when $B_3$ is a sulfonyl group, then m is 0, and $R_3$ is not a hydrogen atom}];
(ii) a $D_5$ group: an O=C($R_3$)-group ($R_3$ is as defined above), an $A_1$-(O)$_n$—N=C($R_3$)-group ($A_1$, n and $R_3$ are as defined above), a $R_1$—$B_0$—CO—$R_4$—(O)$_n$—N=C($R_3$)-group [$R_1$, $R_4$, n and $R_3$ are as defined above, and $B_0$ represents an oxy group, a thio group or a —N(($O)_m R_1'$)-group ($R_1'$ and m are as defined above)], a $D_2$-$R_4$—(O)$_n$—N=C($R_3$)- group ($D_2$, $R_4$, n and $R_3$ are as defined above) or a $R_1A_1N$—N=C($R_3$)-group ($R_1$, $A_1$ and $R_3$ are as defined above);

(iii) a $D_1$ group: a ($R_1$—(O)$_k$-)$A_1$N—(O)$_k$'-group ($R_1$ and $A_1$ are as defined above, and k and k' are the same or different, and represent 0 or 1);

(iv) a $D_2$ group: a cyano group, a $R_1R_1$'NC(=N—(O)$_n$-$A_1$)-group ($R_1$, $R_1$', n and $A_1$ are as defined above), an $A_1$N=C(—O$R_2$)-group ($A_1$ and $R_2$ are as defined above) or a $NH_2$—CS-group;

(v) a $D_3$ group: a nitro group or a $R_1OSO_2$-group ($R_1$ is as defined above);

(vi) an $A_2$ group:

1) an $A_3$-$B_4$-group

[$A_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a $R_a$—($R_4$)$_m$-group ($R_a$ represents a phenyl group, a pyridyl group, a furyl group or a thienyl group, optionally substituted with a halogen atom, a C1-C10 alkyl group, a C1-C10 alkoxy group or a nitro group, and $R_4$ and m are as defined above), or a C1-C10 alkyl group substituted with a (b)-$R_4$-group ((b) and $R_4$ are as defined above), a (c)-$R_4$-group ((c) and $R_4$ are as defined above)], a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $A_4$-$SO_2$—$R_4$-group {$A_4$ is as defined above, and $R_4$ is as defined above}, $B_4$ represents an oxy group, a thio group, or a —N((O)$_m$$R_1$)-group ($R_1$ and m are as defined above), provided that when $B_4$ is a thio group, then $A_3$ is not a hydrogen atom];

2) a $R_1$—$B_4$—CO—$R_4$—$B_4$'-group ($R_1$, $B_4$ and $R_4$ are as defined above, $B_4$' is the same as or different from $R_4$, and has the same meaning as that of $B_4$, provided that when $R_4$ is a thio group, then $R_2$ is not a hydrogen atom) or a $D_2$-$R_4$—$B_4$-group ($D_2$, $R_4$ and $B_4$ are as defined above);

3) a $R_2$—$SO_2$—$NR_1$-group ($R_2$ is as defined above, provided that a hydrogen atom is excluded, and $R_1$ is as defined above);

4) a (b)-group ((b) is as defined above);

5) a (c)-group ((c) is as defined above) or 6) a $R_1A_1N$—$NR_1$'-group ($R_1$, $A_1$ and $R_1$' are as defined above);

IV. $T_A$ represents a hydrogen atom, an $A_9$'-group ($A_9$' is as defined above), a $D_5$-$R_4$-group ($D_5$ and $R_4$ are as defined above) or a $M_c$-group ($M_c$ is as defined above);

V. $K_a$ represents a hydrogen atom, a halogen atom or a C1-C10 alkyl group, $L_a$ represents a hydrogen atom, a C1-C10 alkyl group or a $M_b$-group ($M_b$ is as defined above) or a $K_a$ and $L_a$ may form a C1-C10 alkylene group; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range]; and an inert carrier;

16. A 2(1H)-pyridinone compound represented by the formula (XVI):

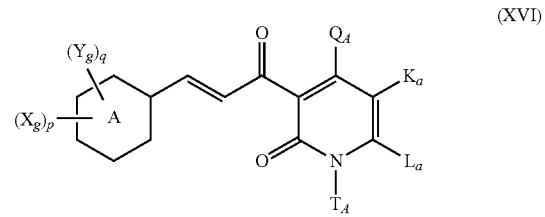

(XVI)

[wherein

I. A represents a benzene ring or a pyridine ring;

II. In ($X_g$)$_p$, $X_g$ represents a hydroxyl group, a halogen atom, a (R')$_2$N-group (R' represents a C1-C10 alkyl group), a nitro group or a C1-C10 alkoxy group, p represents 0, 1, 2, 3 or 4 and, when p is 2 or more, $X_g$'s are the same or different;

III. In ($Y_g$)$_q$, $Y_g$ is a substituent on a carbon atom, and represents a group of the following $X_6$ group or $Y_6$ group, q represents 0, 1, 2, 3, 4 or 5, when q is 2 or more, $Y_g$'s are the same or different and, when q is 2 or more, the adjacent two same or different $Y_g$'s constitutes a group of a $Z_6$ group, and may be fused with an A ring;

(1) a $X_6$ group:

a $M_a$-group [$M_a$ represents a $R_b$-group ($R_b$ represents a C1-C10 alkyl group optionally substituted with a halogen atom), a halogen atom, a nitro group, a cyano group, a hydroxyl group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_e$O—CO—$R_d$-group ($R_e$ and $R_d$ are as defined above), a HO—CO—CH=CH-group, a $R_eR_e$'N—$R_d$-group ($R_e$ and $R_e$' are the same or different, $R_e$ is as defined above, $R_e$' has the same meaning as that of $R_e$, and $R_d$ is as defined above), a $R_e$—CO—$NR_e$'—$R_d$-group ($R_e$, $R_e$' and $R_d$ are as defined above), a $R_b$O—CO—N($R_e$)—$R_d$-group ($R_b$, $R_e$ and $R_d$ are as defined above), a $R_eR_e$'N—CO—$R_d$-group ($R_e$, $R_e$' and $R_d$ are as defined above), a $R_eR_e$'N—CO—$NR_e$"—$R_d$-group ($R_e$, $R_e$' and $R_e$" are the same or different, $R_e$ and $R_e$' are as defined above, $R_e$" has the same meaning as that of a $R_e$, and $R_d$ is as defined above), a $R_eR_e$'N—C(=$NR_e$")—$NR_e$'"—$R_d$-group ($R_e$, $R_e$', $R_e$" and R'" are the same or different, $R_e$, $R_e$' and $R_e$" are as defined above, $R_e$'" has the same meaning as that of $R_e$, and $R_d$ is as defined above), a $R_b$—$SO_2$—$NR_e$—$R_d$-group ($R_b$, $R_e$ and $R_d$ are as defined above), a $R_eR_e$'N—$SO_2$—$R_d$-group ($R_e$, $R_e$' and $R_d$ are as defined above), a C2-C10 alkenyl group or a C2-C10 alkynyl group], provided that when A represents a benzene ring, then a $X_g$-group ($X_g$ is as defined above) is excluded;

(2) a $Y_6$ group:

a $M_b$-$R_d$-group [$M_b$ represents a $M_c$-group {$M_c$ represents a $M_d$-$R_d$'-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

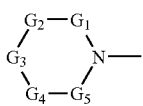

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —$NR_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group}, or a C2-C10 alkenylene group optionally substituted with a methyl group, an oxy group, a thio group, a sulfinyl group, a sulfonyl group or a —$NR_1$-group ($R_1$ is as defined above)}, (c)

a (c)-group (in (c), $J_1$, $J_2$ and $J_3$ are the same or different, and represent a methine group optionally substituted with a methyl group, or a nitrogen atom), (d)

a (d)-group (l is 2, 3 or 4, and $B_b$ represents an oxy group or a thio group) or (e)

an (e)-group (l and $B_b$ are as defined above), $R_d'$ is the same as or different from $R_d$, and has the same meaning as that of $R_d$}}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_eN$-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_cR_eN$—CO-group ($M_c$ and $R_e$ are as defined above), a $M_cR_eN$—CO—$NR_e'$-group ($M_c$, $R_e$ and $R_e'$ are as defined above), a $M_cR_eN$—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_cR_eN$—$SO_2$-group ($M_c$ and $R_e$ are as defined above), and $R_d$ is as defined above];

(3) a $Z_6$ group:
a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$—$Y_b''$-group ($Y_b$ and $Y_b''$ are the same or different, a methylene group, or an oxy group, or a thio group, or a sulfinyl group, or an imino group optionally substituted with a C1-C10 alkyl group, and $Y_b'$ represents a C1-C4 alkylene group optionally substituted with a halogen atom, or a C1-C4 alkylene group optionally having an oxo group) or a —$Y_c$—O—$Y_c'$—O-group ($Y_c$ and $Y_c'$ are the same or different, and represent a C1-C10 alkylene group);

IV. $Q_A$ represents a hydroxyl group, a (b)-group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, and $B_c$ represents an oxy group or a —N(($O)_mR_1$)-group (m represents 0 or 1, and $R_1$ is as defined above), provided that when $A_9$ is a hydrogen atom, then $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, $B_1$ is as defined above, provided that $A_8$ is not a hydrogen atom), a $R_1R_1'N$—$SO_2$—$B_c$-group ($R_1$ is as defined above, $R_1'$ is the same as or different from $R_1$, and has the same meaning as that of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above), or a $M_c$-$B_c$-group ($M_c$ and $B_c$ are as defined above);

(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group ($D_2$ represents a substituent of the following $D_2$ group, and $R_4$ is as defined above), a $D_3$-$R_4$-group {$D_3$ represents a substituent of the following $D_3$ group, and $R_4$ is as defined above}, an $A_4$-$SO_2$—$R_4$-group {$A_4$ represents a -(b)-group ((b) is as defined above), a (c)-group ((c) is as defined above) or a $R_1R_1'N$-group ($R_1$ and $R_1'$ are as defined above), and $R_4$ is as defined above} or an $A_2$-CO—$R_4$ group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$-group ($D_4$ and $R_4'$ are as defined above), a D₁-R₄'-group (D₁ and R₄' are as defined above), a (b)-R₄'-group ((b) and R₄' are as defined above), a (c)-R₄'-group ((c) and R₄' are as defined above), a D₂-R₄-group (D₂ and R₄ are as defined above), a D₃-R₄'-group (D₃ and R₄' are as defined above), and an A₂-CO—R₄-group (A₂ and R₄ are as defined above);

(4) an A₈' group: a C1-C10 alkyl group or a C2-C10 haloalkyl group;

(5) an A₇'' group: a C2-C10 alkenyl group, a C3-C10 alkenyl group substituted with a halogen atom, a C3-C10 alkynyl group optionally substituted with a halogen atom, a R₂—B₁—R₄'-group (R₂, B₁ and R₄' are as defined above), a D₄-R₄'-group (D₄ and R₄' are as defined above), a D₅-R₄-group (D₅ and R₄ are as defined above), a D₁-R₄'-group (D₁ and R₄' are as defined above), a (b)-R₄'-group ((b) and R₄' are as defined above), a (c)-R₄'-group ((c) and R₄' are as defined above), a D₂-R₄-group (D₂ and R₄ are as defined above), a NO₂—R₄-group (R₄ is as defined above) or an A₂-CO—R₄-group (A₂ and R₄ are as defined above);

(i) a D₄ group: a hydroxyl group or an A₁-O-group [A₁ represents a R₃—(CHR₀)ₘ—(B₂—B₃)ₘ'-group {R₃ represents a hydrogen atom, or a C1-10 alkyl group optionally substituted with a halogen atom or a R₂—B₁-group (R₂ and B₁ are as defined above), or a C1-C10 alkenyl group, or a C2-C10 alkynyl group, R₀ represents a hydrogen atom, a C1-C10 alkyl group or a C2-C10 haloalkyl group, m is as defined above, B₂ represents a single bond, an oxy group, a thio group or a —N((O)ₙR₁)— group (R₁' is as defined above, and n represents 0 or 1), B₃ is as defined above, m' represents 0 or 1 and, when B₃ is a sulfonyl group, m is 0, and R₃ is not a hydrogen atom}];

(ii) a D₅ group: an O=C(R₃)-group (R₃ is as defined above), an A₁-(O)ₙ—N=C(R₃)-group (A₁, n and R₃ are as defined above), a R₁—B₀—CO—R₄—(O)ₙ—N=C(R₃)-group [R₁, R₄, n and R₃ are as defined above, and B₀ represents an oxy group, a thio group or a —N((O)ₘR₁')-group (R₁' and m are as defined above)], a D₂-R₄—(O)ₙ—N=C(R₃)-group (D₂, R₄, n and R₃ are as defined above) or a R₁A₁N—N=C(R₃)-group (R₁, A₁ and R₃ are as defined above);

(iii) a D₁ group: a (R₁—(O)ₖ-)A₁N—(O)ₖ'-group (R₁ and A₁ are as defined above, and k and k' are the same or different, and represent 0 or 1);

(iv) a D₂ group: a cyano group, a R₁R₁'NC(=N—(O)ₙ-A₁)-group (R₁, R₁', n and A₁ are as defined above), an A₁N=C(—OR₂)-group (A₁ and R₂ are as defined above) or a NH₂—CS-group;

(v) a D₃ group: a nitro group or a R₁OSO₂-group (R₁ is as defined above);

(vi) an A₂ group:

1) an A₃-B₄-group

[A₃ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a Rₐ—(R₄)ₘ-group (Rₐ represents a phenyl group, a pyridyl group, a furyl group or a thienyl group, optionally substituted with a halogen atom, a C1-C10 alkyl group a C1-C10 alkoxy group or a nitro group, and R₄ and m are as defined above), or a C1-C10 alkyl group substituted with a (b)-R₄-group ((b) and R₄ are as defined above), a (c)-R₄-group ((c) and R₄ are as defined above), a R₂—B₁—R₄-group (R₂, B₁ and R₄ are as defined above), a D₄-R₄-group (D₄ and R₄ are as defined above), a D₅-group (D₅ is as defined above), a D₁-R₄-group (D₁ and R₄ are as defined above), a D₂-group (D₂ is as defined above), a D₃-R₄-group (D₃ and R₄ are as defined above) or an A₄-SO₂—R₄-group {A₄ is as defined above, and R₄ is as defined above}, B₄ represents an oxy group, a thio group or a —N((O)ₘR₁)-group (R₁ and m are as defined above), provided that when B₄ is a thio group, then A₃ is not a hydrogen atom];

2) a R₁—B₄—CO—R₄—B₄'-group (R₁, B₄ and R₄ are as defined above, B₄' is the same as or different from B₄, and has the same meaning as that of B₄, provided that when B₄ is a thio group, then R₂ is not a hydrogen atom) or a D₂-R₄—B₄-group (D₂, R₄ and B₄ are as defined above);

3) a R₂—SO₂—NR₁-group (R₂ is as defined above, provided that a hydrogen atom is excluded, and R₁ is as defined above);

4) a (b)-group ((b) is as defined above);

5) a (c)-group ((c) is as defined above) or 6) a R₁A₁N—NR₁'-group (R₁, A₁ and R₁' are as defined above);

V. T_A represents a hydrogen atom, an A₉'-group (A₉' is as defined above), a D₅-R₄-group (D₅ and R₄ are as defined above) or a M_c-group (m_c is as defined above);

VI. K_a represents a hydrogen atom, a halogen atom or a C1-C10 alkyl group, L_a represents a hydrogen atom, a C1-C10 alkyl group or a M_b-group (M_b is as defined above), or K_a and L_a may form a C1-C10 alkylene group, provided that when an A ring is a benzene ring, then q is not 0; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range];

17. A I type collagen gene transcription suppressing composition, which comprises a 2(1H)-pyridinone compound represented by the formula (XVII):

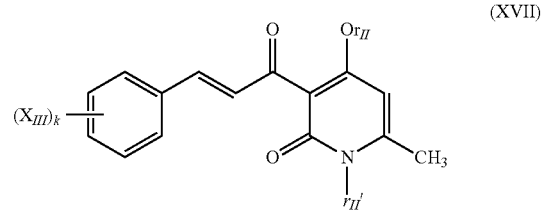

[wherein XIII represents a hydrogen atom, or a hydroxy group, or a halogen atom, or a C1-C4 alkyl group optionally substituted with a halogen atom or a C1-C4 alkoxy group, or a C2-C4 alkenyl group, or a C2-C4 alkynyl group, or a C1-C4 alkoxy group, or a R₁—S(O)₁-group (R₁ represents a C1-C4 alkyl group, and l represents an integer of 0 to 2), or a nitro group, or a cyano group, or a carboxy group, or a C1-C4 alkoxycarbonyl group, or a (R_I)₂N-group (R_I is as defined above), or a R_I—CO—NH-group (R_I is as defined above), or a R_IO—CO—NH-group (R_I is as defined above), or a R_INH—CO—NH-group (R_I is as defined above), or a (R_I')₂N—CO-group (R_I' represents a hydrogen atom or a C1-C4 alkyl group) or a RB-group (B represents an oxygen atom or a sulfur atom, and R represents a C1-C4 alkyl group substituted with a halogen atom), K represents an integer of 1 to 4, when k is an integer of 2 to 4, X_III's may be different, r_II and r_II' are the same or different, and represent a hydrogen atom or a C1-C4 alkyl group];

and an inert carrier;

18. A 2(1H)-pyridinone compound represented by the formula (XVIII):

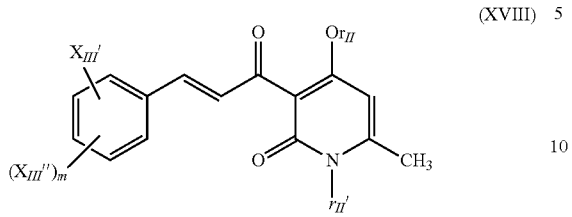

[wherein $X_{III}'$ represents a C2-C4 alkyl group, or a C1-C4 alkyl group substituted with a halogen atom or a C1-C4 alkoxy group, or a C2-C4 alkenyl group, or a C2-C4 alkynyl group, or a C2-C4 alkoxy group, or a $R_J$—S(O)$_l$-group ($R_J$ represents a C1-C4 alkyl group, and l represents an integer of 0 to 2), or a cyano group, or a carboxy group, or a C1-C4 alkoxycarbonyl group, a $(R_{II})_2$N-group ($R_{II}$ represents a C2-C4 alkyl group), or a $R_J$—CO—NH-group ($R_J$ is as defined above), or a $R_JO$—CO—NH-group ($R_J$ is as defined above), or a $R_JNH$—CO—NH-group ($R_J$ is as defined above), or a $(R_J')_2$N—CO-group ($R_J'$ represents a hydrogen atom or a C1-C4 alkyl group), or a RB-group (B represents an oxygen atom or a sulfur atom, and R represents a C1-C4 alkyl group substituted with a halogen atom), $X_{III}''$ represents a hydrogen atom, a halogen atom, a C1-C4 alkyl group, or a C1-C4 alkoxy group, m represents 1 or 2, when m is 2, $X_{III}'''$s may be different, and $r_{II}$ and $r_{II'}$ are the same or different, and represent a hydrogen atom or a C1-C4alkyl group];

19. A I type collagen gene transcription suppressing composition, which comprises a 2(1H)-quinolinone compound represented by the formula (XIX):

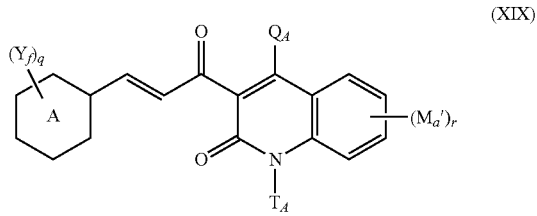

[wherein
I. A represents a benzene ring or a pyridine ring;
II. In $(Y_f)_q$, $Y_f$ is a substituent on a carbon atom, and represents a group of the following X group or Y group, q represents 0, 1, 2, 3, 4 or 5, when q is 2 or more, $Y_f$'s are the same or different and, when q is 2 or more, the adjacent two same or different $Y_f$'s constitute a group of a Z group, and may be fused with an A ring;
(1) a X group:
a $M_a$-group [$M_a$ represents a $R_b$-group ($R_b$ represents a C1-C10 alkyl group optionally substituted with a halogen atom), a halogen atom, a nitro group, a cyano group, a hydroxyl group, a $R_c$—$B_a$—$R_d$-group ($R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), a HOR$_d$-group ($R_d$ is as defined above), a $R_e$—CO—$R_d$-group ($R_e$ represents a hydrogen atom, or a C1-C10 alkyl group optionally substituted with a halogen atom, and $R_d$ is as defined above), a $R_e$—CO—O—$R_d$-group ($R_e$ and $R_d$ are as defined above), a $R_eO$—CO—$R_d$-group ($R_e$ and $R_d$ are as defined above), a HO—CO—CH=CH-group, a $R_eR_e'$N—$R_d$-group ($R_e$ and $R_e'$ are the same or different, $R_e$ is as defined above, $R_e'$ has the same meaning as that of $R_e$, and $R_d$ is as defined above), a $R_e$—CO—NR$_e'$—$R_d$-group ($R_e$, $R_e'$ and $R_d$ are as defined above), a $R_bO$—CO—N($R_e$)—$R_d$-group ($R_b$, $R_e$ and $R_d$ are as defined above), a $R_eR_e'$N—CO—$R_d$-group ($R_e$, $R_e'$ and $R_d$ are as defined above), a $R_eR_e'$N—CO—NR$_e''$—$R_d$-group ($R_e$, $R_e'$ and $R_e''$ are the same or different, $R_e$ and $R_e'$ are as defined above, $R_e''$ has the same meaning as that of $R_e$, and $R_d$ is as defined above), a $R_eR_e'$N—C(=NR$_e''$)—NR$_e'''$—$R_d$-group ($R_e$, $R_e'$, $R_e''$ and $R_e'''$ are the same or different, $R_e$, $R_e'$ and $R_e''$ are as defined above, $R_e'''$ has the same meaning as that of $R_e$, and $R_d$ is as defined above), a $R_b$—SO$_2$—NR$_e$—$R_d$-group ($R_b$, $R_e$ and $R_d$ are as defined above), a $R_eR_e'$N—SO$_2$—$R_d$-group ($R_e$, $R_e'$ and $R_d$ are as defined above), a C2-C10 alkenyl group or a C2-C10 alkynyl group];

(2) a Y group:
a $M_b$-$R_d$-group [$M_b$ represents a $M_c$-group {$M_c$ represents a $M_d$-$R_d'$-group {$M_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

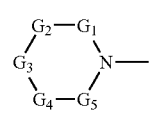

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —NR$_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group}, or a C2-C10 alkenylene group optionally substituted with a methyl group, an oxy group, a thio group, a sulfinyl group, a sulfonyl group or a —NR$_1$-group ($R_1$ is as defined above)},

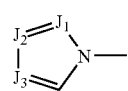

a (c)-group (in (c), $J_1$, $J_2$ and $J_3$ are the same or different, and represent a methine group optionally substituted with a methyl group, or a nitrogen atom),

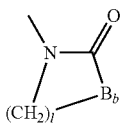

a (d)-group (l is 2, 3 or 4, and $B_b$ represents an oxy group or a thio group)
or

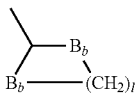

an (e)-group (l and $B_b$ are as defined above), $R_d'$ is the same as or different from $R_d$, and has the same meaning as that of $R_d$}}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_eN$-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_cR_eN$—CO-group ($M_c$ and $R_e$ are as defined above), a $M_cR_eN$—CO—$NR_e'$-group ($M_c$, $R_e$ and $R_e'$ are as defined above), a $M_cR_eN$—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_cR_eN$—$SO_2$-group ($M_c$ and $R_e$ are as defined above), and $R_d$ is as defined above];

(3) a Z group:
a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$—$Y_b''$-group ($Y_b$ and $Y_b'$ are the same or different, and represent a methylene group, or an oxy group, or a thio group, or a sulfinyl group, or an imino group optionally substituted with a C1-C10 alkyl group, and $Y_b'$ represents a C1-C4 alkylene group optionally substituted with a halogen atom, or a C1-C4 alkylene group optionally having an oxo group) or a —$Y_c$—O—$Y_c'$—O-group ($Y_c$ and $Y_c'$ are the same or different, and represent a C1-C10 alkylene group);

III. $Q_A$ represents a hydroxy group, a (b)-group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, and $B_c$ represents an oxy group or a —N((O)$_m$$R_1$)-group (m represents 0 or 1, and $R_1$ is as defined above), provided that when $A_9$ is a hydrogen atom, then $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1R_1'N$—$SO_2$—$B_c$-group ($R_1$ is as defined above, $R_1'$ is the same as or different from $R_1$, and has the same meaning as that of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above) or a $M_c$-$B_c$-group ($M_c$ and $B_c$ are as defined above);

(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1R_1'N$-group ($R_1$ and $R_1'$ are as defined above), and $R_4$ is as defined above} or an $A_2$-CO—$R_4$-group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$-group ($D_4$ and $R_4'$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $D_3$-$R_4'$-group ($D_3$ and $R_4'$ are as defined above) or an $A_2$-CO—$R_4$-group ($A_2$ and $R_4$ are as defined above);

(4) an $A_8'$ group: a C1-C10 alkyl group or a C2-C10 haloalkyl group;

(5) an $A_7''$ group: a C2-C10 alkenyl group, a C3-C10 alkenyl group substituted with a halogen atom, a C3-C10 alkynyl group optionally substituted with a halogen atom, a $R_2$—$B_1$—$R_4'$-group ($R_2$, $B_1$ and $R_4'$ are as defined above), a $D_4$-$R_4'$-group ($D_4$ and $R_4'$ are as defined above), a $D_5$-$R_4$-group ($D_5$ and $R_4$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);

(i) a $D_4$ group: a hydroxy group or an $A_1$-O-group [$A_1$ represents a $R_3$—(CHR$_0$)$_m$—($B_2$—$B_3$)$_m'$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —N((O)$_n$$R_1'$)-group ($R_1'$ is as defined above, and n represents 0 or 1), $B_3$ is as defined above, m' represents 0 or 1 and, when $B_3$ is a sulfonyl group, then m is 0, and $R_3$ is not a hydrogen atom}];

(ii) a $D_5$ group: an O=C($R_3$)-group ($R_3$ is as defined above), an $A_1$-(O)$_n$—N=C($R_3$)-group ($A_1$, n and $R_3$ are as defined above), a $R_1$—$B_0$—CO—$R_4$—(O)$_n$—N=C($R_3$)-group [$R_1$, $R_4$, n and $R_3$ are as defined above, and $B_0$ represents an oxy group, a thio group or a —N((O)$_m$R$_1$')-group (R$_1$' and m are as defined above)], a D$_2$-R$_4$—(O)$_n$—N=C(R$_3$)-group (D$_2$, R$_4$, n and R$_3$ are as defined above) or a R$_1$A$_1$N—N=C(R$_3$)-group (R$_1$, A$_1$ and R$_3$ are as defined above);

(iii) a D$_1$ group: a (R$_1$—(O)$_k$-)A$_1$N—(O)$_k$'-group (R$_1$ and A$_1$ are as defined above, and k and k' are the same or different, and represent 0 or 1);

(iv) a D$_2$ group: a cyano group, a R$_1$R$_1$'NC(=N—(O)$_n$-A$_1$)-group (R$_1$, R$_1$', n and A$_1$ are as defined above), an A$_1$N=C(—OR$_2$)-group (A$_1$ and R$_2$ are as defined above) or a NH$_2$—CS-group;

(v) a D$_3$ group: a nitro group or a R$_{10}$SO$_2$-group (R$_1$ is as defined above);

(vi) an A$_2$ group:

1) an A$_3$-B$_4$-group

[A$_3$ represents a hydrogen atom, or a C1-C10 alkyl group, or a C2-C10 haloalkyl group, or a C2-C10 alkenyl group optionally substituted with a halogen atom, or a C3-C10 alkynyl group optionally substituted with a halogen atom, or a R$_a$—(R$_4$)$_m$-group (R$_a$ represents a phenyl group, a pyridyl group, a furyl group or a thienyl group, optionally substituted with a halogen atom, a C1-C10 alkyl group, a C1-C10 alkoxy group or a nitro group, and R$_4$ and m are as defined above), or a C1-C10 alkyl group substituted with a (b)-R$_4$-group ((b) and R$_4$ are as defined above), a (c)-R$_4$-group ((c) and R$_4$ are as defined above), a R$_2$—B$_1$—R$_4$-group (R$_2$, B$_1$ and R$_4$ are as defined above), a D$_4$-R$_4$-group (D$_4$ and R$_4$ are as defined above), a D$_5$-group (D$_5$ is as defined above), a D$_1$-R$_4$-group (D$_1$ and R$_4$ are as defined above), a D$_2$-group (D$_2$ is as defined above), a D$_3$-R$_4$-group (D$_3$ and R$_4$ are as defined above) or an A$_4$-SO$_2$—R$_4$-group {A$_4$ is as defined above, and R$_4$ is as defined above}, B$_4$ represents an oxy group, a thio group or a —N((O)$_n$R$_1$)-group (R$_1$ and m are as defined above), provided that when B$_4$ is a thio group, then A$_3$ is not a hydrogen atom];

2) a R$_1$—B$_4$—CO—R$_4$—B$_4$'-group (R$_1$, B$_4$ and R$_4$ are as defined above, B$_4$' is the same as or different from B$_4$, and has the same meaning as that of B$_4$, provided that when B$_4$ is a thio group, then R$_2$ is not a hydrogen atom) or a D$_2$-R$_4$—B$_4$-group (D$_2$, R$_4$ and B$_4$ are as defined above);

3) a R$_2$—SO$_2$—NR$_1$-group (R$_2$ is as defined above, provided that a hydrogen atom is excluded, and R$_1$ is as defined above);

4) a (b)-group ((b) is as defined above);

5) a (c)-group ((c) is as defined above) or 6) a R$_1$A$_1$N—NR$_1$'-group (R$_1$, A$_1$ and R$_1$' are as defined above);

IV. T$_A$ represents a hydrogen atom, an A$_9$'-group (A$_9$' is as defined above), a D$_5$-R$_4$-group (D$_5$ and R$_4$ are as defined above) or a M$_c$-group (M$_c$ is as defined above);

V. M$_a$' is the same as or different from M$_a$, and has the same meaning as that of M$_a$, and r represents 0, 1, 2, 3 or 4; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range]; and an inert carrier;

20. A 2(1H)-pyridinone compound represented by the formula (XX):

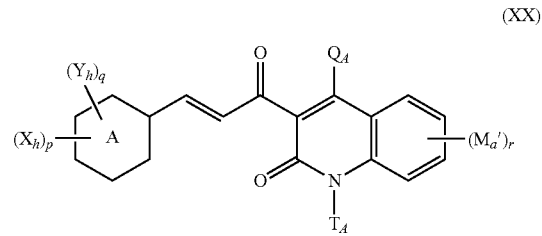

(XX)

[wherein

I. A represents a benzene ring or a pyridine ring;

II. In (X$_h$)$_p$, X$_h$ represents a hydroxy group, a halogen atom, a C1-C10 alkyl group, a C1-C10 alkoxycarbonyl group, a (R')$_2$N-group (R' represents a C1-C10 alkyl group), a nitro group or a C1-C10 alkoxy group, p represents 0, 1, 2, 3 or 4 and, when p is 2 or more, X$_h$'s are the same or different, provided that when p is 2 or more, and in case that X$_h$ is selected from a hydroxy group, a halogen atom, a C1-C10 alkyl group and a C1-C10 alkoxy group, then X$_h$'s do not represent the same group or atom at the same time;

III. In (Y$_h$)$_q$, Y$_h$ is a substituent on a carbon atom, and represents a substituent of the following X$_7$ group or Y$_7$ group, q represents 0, 1, 2, 3, 4 or 5, when q is 2 or more, Y$_h$'s are the same or different and, when q is 2 or more, the adjacent two same or different Y$_h$'s constitute a group of a Z$_7$ group, and may be fused with an A ring;

(1) a X$_7$ group:

a M$_a$-group [M$_a$ represents a R$_b$-group (R$_b$ represents a C1-C10 alkyl group optionally substituted with a halogen atom), a halogen atom, a nitro group, a cyano group, a hydroxy group, a R$_c$—B$_a$—R$_d$-group (R$_c$ represents a C1-C10 alkyl group optionally substituted with a halogen atom, B$_a$ represents an oxy group, a thio group, a sulfinyl group or a sulfonyl group, and R$_d$ represents a single bond or a C1-C10 alkylene group), a HOR$_d$-group (R$_d$ is as defined above), a R$_e$—CO—R$_d$-group (R$_e$ represents a hydrogen atom, or a C1-C10 alkyl group optionally substituted with a halogen atom, and R$_d$ is as defined above), a R$_e$—CO—O—R$_d$-group (R$_e$ and R$_d$ are as defined above), a R$_e$O—CO—R$_d$-group (R$_e$ and R$_d$ are as defined above), a HO—CO—CH=CH-group, a R$_e$R$_e$'N—R$_d$-group (R$_e$ and R$_e$' are the same or different, R$_e$ is as defined above, R$_e$' has the same meaning as that of R$_e$, and R$_d$ is as defined above), a R$_e$—CO—NR$_e$'—R$_d$-group (R$_e$, R$_e$' and R$_d$ are as defined above), a R$_b$O—CO—N(R$_e$)—R$_d$-group (R$_b$, R$_e$ and R$_d$ are as defined above), a R$_e$R$_e$'N—CO—R$_d$-group (R$_e$, R$_e$' and R$_d$ are as defined above), a R$_e$R$_e$'N—CO—NR$_e$"—R$_d$-group (R$_e$, R$_e$' and R$_e$" are the same or different, R$_e$ and R$_e$' are as defined above, R$_e$" has the same meaning as that of R$_e$, and R$_d$ is as defined above), a R$_e$R$_e$"N—C(=NR$_e$")—NR$_e$'"—R$_d$-group (R$_e$, R$_e$', R$_e$" and R$_e$'" are the same or different, R$_e$, R$_e$' and R$_e$" are as defined above, R$_e$'" has the same meaning as that of R$_e$, and R$_d$ is as defined above), a R$_b$—SO$_2$—NR$_e$—R$_d$-group (R$_b$, R$_e$ and R$_d$ are as defined above), a R$_e$R$_e$'N—SO$_2$—R$_d$-group (R$_e$, R$_e$' and R$_d$ are as defined above), a C2-C10 alkenyl group or a C2-C10 alkynyl group], provided that when A represents a benzene ring, then a X$_h$-group (X$_h$ is as defined above) is excluded;

(2) a Y$_7$ group:

a M$_b$-R$_d$-group [M$_b$ represents a M$_c$-group {M$_c$ represents a M$_d$-R$_d$'-group {M$_d$ represents a phenyl group optionally substituted with a $M_a$-group ($M_a$ is as defined above), or a pyridyl group optionally substituted with a $M_a$-group ($M_a$ is as defined above), or a naphthyl group optionally substituted with a $M_a$-group ($M_a$ is as defined above), or

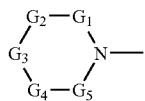
(b)

a (b)-group {in (b), $G_1$, $G_2$, $G_4$ and $G_5$ represent a methylene group which is connected to an adjacent atom with a single bond, and may be substituted with a methyl group, or a methine group which is connected to an adjacent atom with a double bond, and may be substituted with a methyl group, and $G_3$ represents a single bond, or a double bond, or a C1-C10 alkylene group optionally substituted with a methyl group, an oxy group, a thio group, a sulfinyl group, a sulfonyl group or a —$NR_1$-group {$R_1$ represents a hydrogen atom, or a C1-C10 alkyl group, or a C2-C10 alkyl group substituted with a halogen atom or a $R_2$—$B_1$-group ($R_2$ represents a C1-C10 alkyl group, a C3-C10 alkenyl group or a C3-C10 alkynyl group, and $B_1$ represents an oxy group, a thio group, a sulfinyl group or a sulfonyl group), or a C3-C10 alkenyl group, or a C3-C10 alkynyl group), or a C2-C10 alkenylene group optionally substituted with a methyl group, an oxy group, a thio group, a sulfinyl group, a sulfonyl group or a —$NR_1$-group ($R_1$ is as defined above)},

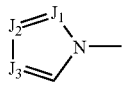
(c)

a (c)-group (in (c), $J_1$, $J_2$ and $J_3$ are the same or different, and represent a methine group optionally substituted with a methyl group, or a nitrogen atom),

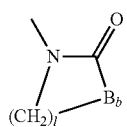
(d)

a (d)-group (l is 2, 3 or 4, and $B_b$ represents an oxy group or a thio group) or

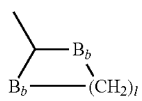
(e)

an (e)-group (l and $B_b$ are as defined above), $R_d'$ is the same as or different from $R_d$, and has the same meaning as that of $R_d$]}, a $M_c$-$B_a$-group ($M_c$ and $B_a$ are as defined above), a $M_c$-CO-group ($M_c$ is as defined above), a $M_c$-CO—O-group ($M_c$ is as defined above), a $M_c$O—CO-group ($M_c$ is as defined above), a $M_cR_eN$-group ($M_c$ and $R_e$ are as defined above), a $M_c$-CO—$NR_e$-group ($M_c$ and $R_e$ are as defined above), a $M_c$O—CO—$NR_e$-group ($M_c$ and $R_e$ are as defined above), a $M_cR_eN$—CO-group ($M_c$ and $R_e$ are as defined above), a $M_cR_eN$—CO—$NR_e'$-group ($M_c$, $R_e$ and $R_e'$ are as defined above), a $M_cR_eN$—C(=$NR_e'$)—$NR_e''$-group ($M_c$, $R_e$, $R_e'$ and $R_e''$ are as defined above), a $M_c$-$SO_2$—$NR_e$-group ($M_c$ and $R_e$ are as defined above) or a $M_cR_eN$—$SO_2$-group ($M_c$ and $R_e$ are as defined above), and $R_d$ is as defined above];

(3) a $Z_7$ group:
a —N=C($Y_a$)—$Y_a'$-group ($Y_a$ represents a hydrogen atom, or a C1-C10 alkyl group optionally substituted with a halogen atom, or a C1-C10 alkoxy group, and $Y_a'$ represents an oxy group, or a thio group, or an imino group optionally substituted with a C1-C10 alkyl group), a —$Y_b$—$Y_b'$—$Y_b''$-group ($Y_b$ and $Y_b''$ are the same or different, and represent a methylene group, or an oxy group, or a thio group, or a sulfinyl group, or an imino group optionally substituted with a C1-C10 alkyl group, and $Y_b'$ represents a C1-C4 alkylene group optionally substituted with a halogen atom or a C1-C4 alkylene group optionally having an oxo group) or a —$Y_c$—O—$Y_c'$—O-group ($Y_c$ and $Y_c'$ are the same or different, or a C1-C10 alkylene group), provided that when p is 0, then $Y_b$ does not fused with an A ring to form a benzo[1,3]dioxol ring;

IV. $Q_4$ represents a hydroxy group, a (b)-group ((b) is as defined above), an $A_9$-$B_6$—$B_c$-group [$A_9$ represents a substituent of the following $A_7$ group or $A_8$ group, $B_6$ represents a carbonyl group or a thiocarbonyl group, and $B_c$ represents an oxy group or a —N(($O)_mR_1$-group (m represents 0 or 1, and $R_1$ is as defined above), provided that when $A_9$ is a hydrogen atom, then $B_c$ is not a sulfonyl group], an $A_7''$-$SO_2$—$B_c$-group ($A_7''$ represents a substituent of the following $A_7''$ group, and $B_c$ is as defined above), an $A_8$-$SO_2$—$B_c$-group ($A_8$ represents a substituent of the following $A_8$ group, and $B_c$ is as defined above, provided that $A_8$ is not a hydrogen atom), a $R_1R_1'N$—$SO_2$—$B_c$-group ($R_1$ is as defined above, $R_1'$ is the same as or different from $R_1$, and has the same meaning as that of $R_1$, and $B_c$ is as defined above), a (b)-$SO_2$—$B_c$-group ((b) and $B_c$ are as defined above), an $A_9'$-$B_c$-group ($A_9'$ represents a substituent of the following $A_7'$ group or $A_8'$ group, and $B_c$ is as defined above), a $D_5$-$R_4$—$B_c$-group ($D_5$ represents a substituent of the following $D_5$ group, $R_4$ represents a C1-C10 alkylene group, and $B_c$ is as defined above), a $M_c$-$B_3$—$B_c$-group ($B_3$ represents a carbonyl group, a thiocarbonyl group or a sulfonyl group, and $M_c$ and $B_c$ are as defined above) or a $M_c$-$B_c$-group ($M_c$ and $B_c$ are as defined above);

(1) an $A_7$ group:
a C2-C10 alkenyl group optionally substituted with a halogen atom, a C2-C10 alkynyl group, a C3-C10 haloalkynyl group, a $R_2$—$B_1$—$R_4$-group ($R_2$ and $B_1$ are as defined above, and $R_4$ is as defined above), a $D_4$-$R_4$-group ($D_4$ represents a substituent of the following $D_4$ group, and $R_4$ is as defined above), a $D_5$-$R_4$-group ($D_5$ represents a substituent of the following $D_5$ group, and $R_4$ is as defined above), a $D_1$-$R_4$-group {$D_1$ represents a substituent of the following $D_1$ group, and $R_4$ is as defined above}, a (b)-$R_4$-group ((b) is as defined above, and $R_4$ is as defined above), a (c)-$R_4$-group ((c) is as defined above, and $R_4$ is as defined above), a $D_2$-$R_4$-group {$D_2$ represents a substituent of the following $D_2$ group, and $R_4$ is as defined above}, a $D_3$-$R_4$-group {$D_3$ represents a substituent of the following $D_3$ group, and $R_4$ is as defined above}, an $A_4$-$SO_2$—$R_4$-group {$A_4$ represents a (b)-group ((b) is as defined above), a (c)-group ((c) is as defined above) or a $R_1R_1'$-N-group ($R_1$ and $R_1'$ are as defined above), and $R_4$ is as defined above) or an $A_2$-$CO_2$—$R_4$-group ($A_2$ represents a substituent of the following $A_2$ group, and $R_4$ is as defined above);

(2) an $A_8$ group: a hydrogen atom, or a C1-C10 alkyl group optionally substituted with a halogen atom;

(3) an $A_7'$ group: a C3-C10 alkenyl group optionally substituted with a halogen atom, a C3-C10 alkynyl group optionally substituted with a halogen atom, a $R_2$—$B_1$—$R_4'$-group ($R_2$ and $B_1$ are as defined above, and $R_4'$ represents a C2-C10 alkylene group), a $D_4$-$R_4'$-group ($D_4$ and $R_4'$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4'$-group ($D_2$ and $R_4$ are as defined above), a $D_3$-$R_4'$-group ($D_3$ and $R_4'$ are as defined above) or an $A_2$-CO—$R_4'$-group ($A_2$ and $R_4$ are as defined above);

(4) an $A_8'$ group: a C1-C10 alkyl group or a C2-C10 haloalkyl group;

(5) an $A_7''$ group: a C2-C10 alkenyl group, a C3-C10 alkenyl group substituted with a halogen atom, a C3-C10 alkynyl group optionally substituted with a halogen atom, a $R_2$—$B_1$—$R_4'$-group ($R_2$, $B_1$ and $R_4'$ are as defined above), a $D_4$-$R_4'$-group ($D_4$ and $R_4'$ are as defined above), a $D_5$-$R_4'$-group ($D_5$ and $R_4$ are as defined above), a $D_1$-$R_4'$-group ($D_1$ and $R_4'$ are as defined above), a (b)-$R_4'$-group ((b) and $R_4'$ are as defined above), a (c)-$R_4'$-group ((c) and $R_4'$ are as defined above), a $D_2$-$R_4$-group ($D_2$ and $R_4$ are as defined above), a $NO_2$—$R_4$-group ($R_4$ is as defined above) or an $A_2$-CO—$R_4$-group ($A_2$ and $R_4$ are as defined above);

(i) a $D_4$ group: a hydroxy group or an $A_1$-O-group [$A_1$ represents a $R_3$—$(CHR_0)_m$—$(B_2$—$B_3)_m'$-group {$R_3$ represents a hydrogen atom, or a C1-C10 alkyl group optionally substituted with a halogen atom or a $R_2$—$B_1$-group ($R_2$ and $B_1$ are as defined above), or a C2-C10 alkenyl group, or a C2-C10 alkynyl group, $R_0$ represents a hydrogen atom, a C1-C10 alkyl group or a C2-C10 haloalkyl group, m is as defined above, $B_2$ represents a single bond, an oxy group, a thio group or a —$N((O)_nR_1')$-group ($R_1'$ is as defined above, and n represents 0 or 1), $B_3$ is as defined above, m' represents 0 or 1 and, when $B_3$ is a sulfonyl group, then m is 0, and $R_3$ is not a hydrogen atom}];

(ii) a $D_5$ group: an O=C($R_3$)-group ($R_3$ is as defined above), an $A_1$-$(O)_n$—N=C($R_3$)-group ($A_1$, N and $R_3$ are as defined above), a $R_1$—$B_0$—CO—$R_4$—$(O)_n$—N=C($R_3$)-group [$R_1$, $R_4$, n and $R_3$ are as defined above, and $B_0$ represents an oxy group, a thio group or a —$N((O)_mR_1')$-group ($R_1'$ and m are as defined above)], a $D_2$-$R_4$—$(O)_n$—N=C($R_3$)-group ($D_2$, $R_4$, n and $R_3$ are as defined above) or a $R_1A_1N$—N=C($R_3$)-group ($R_1$, $A_1$ and $R_3$ are as defined above);

(iii) a $D_1$ group: a ($R_1$—O)$_k$-)$A_1N$—$(O)_k'$-group ($R_1$ and $A_1$ are as defined above, and k and k' are the same or different, and represent 0 or 1);

(iv) a $D_2$ group: a cyano group, a $R_1R_1'NC(=N$—$(O)_n$-$A_1$-group ($R_1$, $R_1'$, N and $A_1$ are as defined above), an $A_1N=C(-OR_2)$-group ($A_1$ and $R_2$ are as defined above) or a $NH_2$—CS-group;

(v) a $D_3$ group: a nitro group or a $R_1OSO_2$-group ($R_1$ is as defined above);

(vi) an $A_2$ group:
1) an $A_3$-$B_4$-group
[$A_3$ represents a hydrogen atom, or a C1-C10 alkyl group, or a C2-C10 haloalkyl group, or a C2-C10 alkynyl group optionally substituted with a halogen atom, or a C3-C10 alkynyl group optionally substituted with a halogen atom, or a $R_a$—$(R_4)_m$-group ($R_a$ represents a phenyl group, a pyridyl group, a furyl group or a thienyl group, optionally substituted with a halogen atom, a C1-C10 alkyl group, a C1-C10 alkoxy group or a nitro group, and $R_4$ and m are as defined above), or a C1-C10 alkyl group substituted with a (b)-$R_4$-group ((b) and $R_4$ are as defined above), a (c)-$R_4$- group ((c) and $R_4$ are as defined above), a $R_2$—$B_1$—$R_4$-group ($R_2$, $B_1$ and $R_4$ are as defined above), a $D_4$-$R_4$-group ($D_4$ and $R_4$ are as defined above), a $D_5$-group ($D_5$ is as defined above), a $D_1$-$R_4$-group ($D_1$ and $R_4$ are as defined above), a $D_2$-group ($D_2$ is as defined above), a $D_3$-$R_4$-group ($D_3$ and $R_4$ are as defined above) or an $A_4$-$SO_2$—$R_4$-group {$A_4$ is as defined above, and $R_4$ is as defined above}, $B_4$ represents an oxy group, a thio group or a —$N((O)_mR_1)$-group ($R_1$ and m are as defined above), provide that when $A_4$ is a thio group, then $A_3$ is not a hydrogen atom];

2) a $R_1$—$B_4$—CO—$R_4$—$B_4'$-group ($R_1$, $B_4$ and $R_4$ are as defined above, $B_4'$ is the same as or different from $B_4$, and has the same meaning as $B_4$, provided that when $B_4$ is a thio group, then $R_2$ is not a hydrogen atom) or a $D_2$-$R_4$—$B_4$-group ($D_2$, $R_4$ and $B_4$ are as defined above);

3) a $R_2$—$SO_2$—$NR_1$-group ($R_2$ is as defined above, provided that a hydrogen atom is excluded, and $R_1$ is as defined above);

4) a (b)-group ((b) is as defined above);

5) a (c)-group ((c) is as defined above) or 6) a $R_1A_1N$—$NR_1'$-group ($R_1$, $A_1$ and $R_1'$ are as defined above);

V. $T_A$ represents a hydrogen atom, an $A_9'$-group ($A_9'$ is as defined above), a $D_5$-$R_4$-group ($D_5$ and $R_4$ are as defined above) or a $M_c$-group ($M_c$ is as defined above);

VI. $M_a'$ is the same as or different from $M_a$, and has the same meaning as that of $M_a$, and r represents 0, 1, 2, 3 or 4, provided that when an A ring is a benzene ring, then q is not 0 and, when an A ring is a benzene ring or a pyridine ring, then p and q are not 0 at the same time, in either case; and the "as defined above" in the same symbol between a plurality of substituents indicates that the plurality of substituents independently represent the same meaning as that described above and, between the plurality of substituents, a selection range of selected substituents is the same, while the selected substituents may be the same or different as far as they are selected in the range];

21. A I type collagen gene transcription suppressing composition, which comprises a 2(1H)-quinolinone compound represented by the formula (XXI):

(XXI)

[wherein $X_{IV}$ represents a hydrogen atom, or a hydroxy group, or a halogen atom, or a C1-C4 alkyl group optionally substituted with a halogen atom or a C1-C4 alkoxy group, or a C2-C4 alkenyl group, or a C2-C4 alkynyl group, or a C1-C4 alkoxy group, or a $R_I$—S(O)$_l$-group ($R_I$ represents a C1-C4 alkyl group, and l represents an integer of 0 to 2), or a nitro group, or a cyano group, or a carboxy group, or a C1-C4 alkoxycarbonyl group, or a $(R_I)_2N$-group ($R_I$ is as defined above), or a $R_I$—CO—NH-group ($R_I$ is as defined above), or a $R_I$—O—CO—NH-group ($R_1$ is as defined above), or a $R_INH$—CO—NH-group ($R_I$ is as defined above), or a $(R_I')_2N$—CO-group ($R_I'$ represents a hydrogen atom or a C1-C4 alkyl group), or a RB-group (B represents an oxygen atom or a sulfur atom, and R represents a C1-C4 alkyl group substituted with a halogen atom), k represents an integer of 1 to 4 and, when k is an integer of 2 to 4, $X_{IV}$'s may be different, and $r_{II}$ and $r_{II}'$ are the same or different, and represent a hydrogen atom or a C1-C4 alkyl group];
and an inert carrier;

22. A 2(1H)-quinolinone compound represented by the formula (XXII):

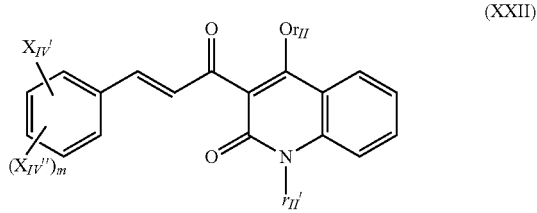

(XXII)

[wherein $X_{IV}'$ represents a C2-C4 alkyl group, or a C1-C4 alkyl group substituted with a halogen atom or a C1-C4 alkoxy group, or a C2-C4 alkenyl group, or a C2-C4 alkynyl group, or a C2-C4 alkoxy group, or a $R_I$—S(O)$_l$-group ($R_I$ represents a C1-C4 alkyl group, and l represents an integer of 0 to 2), or a cyano group, or a carboxy group, or a C2-C4 alkoxycarbonyl group, or a $(R_{II})_2$N-group ($R_{II}$ represents a C2-C4 alkyl group), or a $R_I$—CO—NH-group ($R_I$ is as defined above), or a $R_I$O—CO—NH-group ($R_I$ is as defined above), or a $R_I$NH—CO—NH-group ($R_I$ is as defined above), or a $(R_I')_2$N—CO-group ($R_I'$ represents a hydrogen atom or a C1-C4 alkyl group), or a RB-group (B represents an oxygen atom or a sulfur atom, and R represents a C1-C4 alkyl group substituted with a halogen atom), $X_{IV}''$ represents a hydrogen atom, a halogen atom, a C1-C4 alkyl group or a C1-C4 alkoxy group, m represents 1 or 2 and, when m is 2, $X_{IV}'''$'s may be different, and $r_{II}$ and $r_{II}'$ are the same or different, and represent a hydrogen atom or a C1-C4alkyl group]

23. Use of a compound according to the above item 5, 6, 8, 9, 11, 12, 13, 14, 16, 18, 20 or 22, as an active ingredient for suppressing transcription of a Type I collagen gene;

24. Use of a compound according to the above item 5, 6, 8, 9, 11, 12, 13, 14, 16, 18, 20 or 22, as an active ingredient for decreasing expression of a Type I collagen gene to induce a reduction in accumulation of collagen and thereby improving tissue fibrosis;

25. A composition for improving tissue fibrosis, which comprises a compound according to the above item 5, 6, 8, 9, 11, 12, 13, 14, 16, 18, 20 or 22, and an inert carrier;

26. A method for improving tissue fibrosis, which comprises administering an effective amount of a compound according to the above item 5, 6, 8, 9, 11, 12, 13, 14, 16, 18, 20 or 22 to a mammal in need thereof;

27. Use of a compound according to the above item 5, 6, 8, 9, 11, 12, 13, 14, 16, 18, 20 or 22, as an active ingredient for suppressing the activity of TGF-β;

28. A composition for suppressing the activity of TGF-β, which comprises a compound according to the above item 5, 6, 8, 9, 11, 12, 13, 14, 16, 18, 20 or 22, and an inert carrier;

29. Use of a compound according to the above item 5, 6, 8, 9, 11, 12, 13, 14, 16, 18, 20 or 22, as an active ingredient for inhibiting a promoting effect of TGF-β on transition to a hair regression phase to induce extension of a hair growth phase and thereby providing hair-growing effect;

30. A composition for hair growth which comprises a compound according to the above item 5, 6, 8, 9, 11, 12, 13, 14, 16, 18, 20 or 22, and an inert carrier;

31. A method for growing hair, which comprises administering an effective amount of a compound according to the above item 5, 6, 8, 9, 11, 12, 13, 14, 16, 18, 20 or 22 to a mammal in need thereof;

32. Use of a compound according to the above item 1, 2, 3, 4, 7, 10, 15, 17, 19 or 21, as an active ingredient for suppressing transcription of a Type I collagen gene;

33. Use of a compound according to the above item 1, 2, 3, 4, 7, 10, 15, 17, 19 or 21, as an active ingredient for decreasing expression of a Type I collagen gene to induce a reduction in accumulation of collagen and thereby improving tissue fibrosis;

34. A composition for improving tissue fibrosis, which comprises a compound according to the above item 1, 2, 3, 4, 7, 10, 15, 17, 19 or 21, and an inert carrier;

35. A method for improving tissue fibrosis, which comprises administering an effective amount of a compound according to the above item 1, 2, 3, 4, 7, 10, 15, 17, 19 or 21 to a mammal in need thereof;

36. Use of a compound according to the above item 1, 2, 3, 4, 7, 10, 15, 17, 19 or 21, as an active ingredient for suppressing the activity of TGF-β;

37. A composition for suppressing the activity of TGF-β, which comprises a compound according to the above item 1, 2, 3, 4, 7, 10, 15, 17, 19 or 21, and an inert carrier;

38. Use of a compound according to the above item 1, 2, 3, 4, 7, 10, 15, 17, 19 or 21, as an active ingredient for inhibiting a promoting effect of TGF-β on transition to a hair regression phase to induce extension of a hair growth phase and thereby providing hair-growing effect;

39. A composition for hair growth which comprises a compound according to the above item 1, 2, 3, 4, 7, 10, 15, 17, 19 or 21, and an inert carrier;

40. A method for growing hair, which comprises administering an effective amount of a compound according to the above item 1, 2, 3, 4, 7, 10, 15, 17, 19 or 21 to a mammal in need thereof;

41. A 2(1H)-pyridinone compound represented by the formula (XXIII):

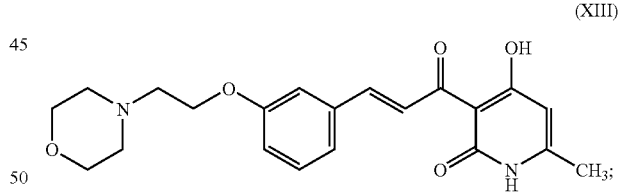

(XIII)

42. A 2(1H)-pyridinone compound represented by the formula (XXIV):

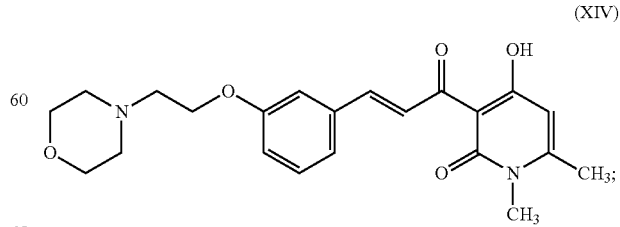

(XIV)

and the like.

BEST MODE FOR CARRYING OUT THE INVENTION

The present invention will be explained in detail below.

In the present invention, a saturated hydrocarbon group in an alkyl group, a haloalkyl group, an alkoxy group, an alkoxycarbonyl group, an alkylthio group, an alkylsulfinyl group, an alkylsulfonyl group and an alkylene group may be branched, and a part or all of carbon atoms thereof may form a ring. An unsaturated hydrocarbon group in an alkenyl group, an alkenyloxy group, an alkynyl group, an alkynyloxy group and an alkenylene group may have a branch, and a part or all of carbon atoms thereof may form a ring, and the number of unsaturated bonds is singular or plural.

In the present invention, examples of an alkyl group include a methyl group, an ethyl group, an isopropyl group, a cyclohexyl group, a cyclopropylmethyl group and the like, examples of a haloalkyl group include a 2,2,2-trifluoroethyl group and the like, examples of an alkoxy group include a methoxy group, an ethoxy group, a cyclopentyloxy group, a 2-cyclohexylethoxy group and the like, examples of an alkylthio group include a methylthio group and the like, examples of an alkylsulfinyl group include a methylsulfinyl group and the like, examples of an alkylsulfonyl group include a methylsulfonyl group and the like, examples of an alkylene group include a methylene group, an ethylethylene group, a 1,4-cyclohexylene group and the like, examples of an alkenyl group include a vinyl group, a 2-propenyl group, a 3-methyl-2-butenyl group, a 1,3-butadienyl group, a 3-cyclohexenyl group and the like, examples of an alkynyl group include an ethynyl group, a 2-propynyl group, a 2-penten-4-ynyl and the like, and examples of an alkenylene group include a vinylene group, a propenylene group, a 1,3-butadienylene group and the like.

In the present invention, examples of a halogen atom include a fluorine atom, a chlorine atom, a bromine atom and an iodine atom.

In the present invention, a pyridyl group includes a 2-pyridyl group, a 3-pyridyl group and a 4-pyridyl group, a furyl group includes a 2-furyl group and a 3-furyl group, a thienyl group includes a 2-thienyl group and a 3-thienyl group, and a naphthyl group includes a 1-naphthyl group and a 2-naphthyl group.

In the present invention, examples of a leaving group include an alkylsulfonyloxy group such as a mesyloxy group and the like, an arylsulfonyloxy group such as a tosyloxy group and the like, an alkoxysulfonyloxy group such as a methoxysulfonyloxy group and the like, and a halogen atom such as a bromine atom and the like.

In a cinnamoyl compound represented by the formulas (I) to (III) (hereinafter, referred to as the present compounds (I) to (III), respectively, in some cases), a 2H-pyran-2-one compound represented by the formula (IV) and (V) (hereinafter, referred to as the present compound (IV) and (V), respectively, in some cases), a 2H-pyran-2-one compound represented by the formula (VI) (hereinafter, referred to as the present intermediate (VI) in some cases), a 2H-1-benzopyran-2-one compound represented by the formulas (X) and (XI) (hereinafter, referred to as the present compounds (X) and (XI), respectively, in some cases), a 2H-1-benzopyran-2-one compound represented by the formula (XII) (hereinafter, referred to as the present intermediate (XII) in some cases), a 2(1H)-pyridinone compound represented by the formulas (XV) and (XVI) (hereinafter, referred to as the present compounds (XV) and (XVI), respectively, in some cases) and a 2(1H)-quinolinone compound represented by the formulas (XIX) and (XX) (hereinafter, referred to as the present compounds (XIX) and (XX), respectively, in some cases), when an A ring is a pyridine ring, a N-oxide thereof is also included.

The present compounds (I) to (V), (VII), (VIII), (X), (XI), (XIII), and (XV) to (XXII) (hereinafter, collectively referred to as the present compound in some cases) represents a pharmacologically acceptable salt thereof at the same time. A pharmacologically acceptable salt represents a salt with an inorganic acid, a salt with an organic acid, a salt with an inorganic base or a salt with an organic base, of the present compound. Examples of a salt with an inorganic acid include hydrochloride, hydrobromide and the like, examples of a salt with an organic acid include acetate, benzoate and the like, examples of a salt with an inorganic base include a potassium salt, a sodium salt and the like, and examples of a base with an organic base include a pyridine salt, a morpholine salt and the like.

$Y_{A0}$, $Q_{A0}$, $K_{A0}$, $L_{A0}$ and $T_{A0}$ in the present compound (II) are independently represented by groups represented by $D_1$, $D_2$, $D_3$, $D_4$, $D_5$, $R_0$, $R_1$, $R_1'$, $R_2$, $R_3$, $R_4$, $R_4'$, $A_1$, $A_2$, $A_3$, $A_4$, $A_7$, $A_7'$, $A_7''$, $A_8$, $A_8'$, $A_9$, $A_9'$, $B_0$, $B_1$, $B_2$, $B_3$, $B_4$, $B_4'$, $B_6$, $(b_0)$, $(c_0)$, $(d_0)$, $(e_0)$, $M_a$, $M_a'$, $M_a''$, $M_a'''$, $M_a''''$, $M_{b0}$, $M_{c0}$, $M_{d0}$, $R_{a0}$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c'$, and integers represented by k, k', l, m, m' and n.

$Y_A$, $Q_A$, $K_A$, $L_A$ and $T_A$ in the present compound (III) are independently represented by groups represented by $D_1$, $D_2$, $D_3$, $D_4$, $D_5$, $R_0$, $R_1$, $R_1'$, $R_2$, $R_3$, $R_4$, $R_4'$, $A_1$, $A_2$, $A_3$, $A_4$, $A_7$, $A_7'$, $A_7''$, $A_8$, $A_8'$, $A_9$, $A_9'$, $B_0$, $B_1$, $B_2$, $B_3$, $B_4$, $B_4'$, $B_6$, (b), (c), (d), (e), $M_a$, $M_a'$, $M_a''$, $M_a'''$, $M_a''''$, $M_b$, $M_c$, $M_d$, $R_a$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c'$, and integers represented by k, k', l, m, m' and n.

$X_a$, $Y_a$, $X_b$, $Y_b$, $X_c$, $Y_c$, $Q_A$, $Q_A'$ and $L_a$ in the present compounds (IV) and (V), and the present intermediate (VI) are independently represented by groups represented by $D_1$, $D_2$, $D_3$, $D_4$, $D_5$, $R_0$, $R_1$, $R_1'$, $R_2$, $R_3$, $R_4$, $R_4'$, $A_1$, $A_2$, $A_3$, $A_4$, $A_7$, $A_7'$, $A_7''$, $A_8$, $A_8'$, $A_9$, $A_9'$, $B_0$, $B_1$, $B_2$, $B_3$, $B_4$, $B_4'$, $B_6$, (b), (c), (d), (e), $M_a$, $M_a'$, $M_a''$, $M_a'''$, $M_a''''$, $M_b$, $M_c$, $M_d$, $R_a$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c'$, and integers represented by k, k', l, m, m' and n.

$X_d$, $Y_d$, $X_e$, $Y_e$, $Q_A$, $Q_A'$ and $M_a'$ in the present compounds (X) and (XI) and the present intermediate (XII) are independently represented by groups represented by $D_1$, $D_2$, $D_3$, $D_4$, $D_5$, $R_0$, $R_1$, $R_1'$, $R_2$, $R_3$, $R_4$, $R_4'$, $A_1$, $A_2$, $A_3$, $A_4$, $A_7$, $A_7'$, $A_7''$, $A_8$, $A_8'$, $A_9$, $A_9'$, $B_0$, $B_1$, $B_2$, $B_3$, $B_4$, $B_4'$, $B_6$, (b), (c), (d), (e), $M_a$, $M_a'$, $M_a''$, $M_a'''$, $M_a''''$, $M_b$, $M_c$, $M_d$, $R_a$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c'$, and integers represented by k, k', l, m, m' and n.

$Y_f$, $X_g$, $Y_g$, $Q_A$, $T_A$ and $L_a$ in the present compounds (XV) and (XVI) are independently represented by groups represented by $D_1$, $D_2$, $D_3$, $D_4$, $D_5$, $R_0$, $R_1$, $R_1'$, $R_2$, $R_3$, $R_4$, $R_4'$, $A_1$, $A_2$, $A_3$, $A_4$, $A_7$, $A_7'$, $A_7''$, $A_8$, $A_8'$, $A_9$, $A_9'$, $B_0$, $B_1$, $B_2$, $B_3$, $B_4$, $B_4'$, $B_6$, (b), (c), (d), (e), $M_a$, $M_a'$, $M_a''$, $M_a'''$, $M_a''''$, $M_b$, $M_c$, $M_d$, $R_a$, $R_b$, $R_c$, $R_d$, $R_d'$, $R_e$, $R_e'$, $R_e''$, $R_e'''$, $B_a$, $B_b$, $B_c$, $Y_a$, $Y_a'$, $Y_b$, $Y_b'$, $Y_b''$, $Y_c$ and $Y_c''$, and integers represented by k, k', l, m, m' and n.

$Y_f$, $X_h$, $Y_h$, $Q_A$, $T_A$ and $M_a'$ in the present compounds (XIX) and (XX) are independently represented by groups represented by $D_1$, $D_2$, $D_3$, $D_4$, $D_5$, $R_0$, $R_1$, $R_1'$, $R_2$, $R_3$, $R_4$, $R_4'$, $A_1$, $A_2$, $A_3$, $A_4$, $A_7$, $A_7'$, $A_7''$, $A_8$, $A_8'$, $A_9$, $A_9'$, $B_0$, $B_1$, $B_2$, $B_3$, $B_4$, $B_4'$, $B_6$, (b), (c), (d), (e), $M_a$, $M_a'$, $M_a''$, $M_a'''$, $M_a''''$, $M_b$, $M_c$, $M_d$, $R_a$, $R_b$, $R_c$, $R_d$, $R_d'$, $R_e$, $R_e'$, $R_e''$, $R'''$, $B_a$, $B_b$, $B_c$, $Y_a$, $Y_a'$, $Y_b$, $Y_b'$, $Y_b''$, $Y_c$ and $Y_c'$ and integers represented by k, k', l, m, m' and n.

In the substituent $Y_0$ group which can be taken by $Y_a$ of the present compound (I), the "6 to 10-membered aryl group" represents a groups constituting a monocyclic or fused aromatic hydrocarbon group, and examples include a phenyl group, a 1-naphthyl group, a 2-naphthyl group, a 6-indanyl group and the like, the "5 to 10-membered heteroaryl group" represents a group constituting a monocyclic or fused aromatic heterocycle, and examples include a 2-furyl group, a 3-furyl group, a 2-thienyl group, a 3-thienyl group, a 2-pyridyl group, a 3-pyridyl group, a 4-pyridyl group, a 2-quinolyl group and the like, and "a group constituting 3 to 10-membered hydrocarbon ring or heterocycle optionally containing an unsaturated bond" includes a monocycle or a fused cycle, and examples include a 2-cyclohexenyl group, a 2-morpholinyl group, a 4-piperidyl group and the like, and these may be substituted with a single or same or different plural aforementioned $M_a$-groups.

In the substituent $Z_0$ group which can be taken by $Y_a$ of the present compound (I), "a group which is fused with an A ring" may have single or the same or different plural atoms or groups selected from a halogen atom, a C1-C10 alkoxy group, a C3-C10 alkenyloxy group, a C3-C10 alkynyloxy group, a carbonyl group, a thiocarbonyl group, an oxy group, a thio group, a sulfinyl group and a sulfonyl group.

In ($d_0$) of the substituent $Y_0$ group which can be taken by $Y_a$ and $Y_{a0}$, of the present compounds (I) and (II), the "5 to 12-membered hydrocarbon ring which is substituted with a carbonyl group or a thiocarbonyl group and, further, may be substituted with an oxy group, a thio group, a —$NR_1$— group ($R_1$ is as defined above), a sulfinyl group or a sulfonyl group" represents a 5 to 12-membered hydrocarbon ring in which one or plural of carbon atoms are substituted with a carbonyl group or a thiocarbonyl group and, further, one or plural of carbon atoms may be substituted with single or the same or different plural groups selected from an oxy group, a thio group, a —$NR_1$-group ($R_1$ is as defined above), a sulfinyl group or a sulfonyl group.

In ($e_0$) of the substituent $Y_0$ group which can be taken by $Y_a$ and $Y_{a0}$, of the present compounds (I) and (II), the "5 to 12-membered hydrocarbon ring optionally substituted with a carbonyl group, a thiocarbonyl group, an oxy group, a thio group, a —$NR_1$-group ($R_1$ is as defined above), a sulfinyl group or a sulfonyl group" represents a 5 to 12-membered hydrocarbon ring in which one or plural of carbon atoms may be substituted with single or the same or different plural groups selected from a carbonyl group, a thiocarbonyl group, an oxy group, a thio group, a —$NR_1$-group ($R_1$ is as defined above), a sulfinyl group and a sulfonyl group.

The groups belonging to a $X_0$ group, a $Y_0$ group and a $Z_0$ group which can be taken by $Y_a$ of the present compound (I) will be exemplified in the following Table X, Table Y and Table Z, respectively.

The groups belonging to a $X_0$ group, a $Y_0$ group and a $Z_0$ group which can be taken by $Y_{A0}$ of the present invention (II) are exemplified in the following Table X, Table Y and Table Z, respectively, and $Q_0$ and $T_0$ are exemplified in the following Table Q and Table T, respectively.

The groups belonging to a X group, a Y group and a Z group which can be taken by $Y_A$ of the present compound (III) are exemplified in the following Table X, Table Y and Table Z, respectively, and Q and T are exemplified in the following Table Q and Table T, respectively.

The groups belonging to the aforementioned $X_0$ group to $Z_0$ group and X group to Z group will be exemplified in the following Table X to Table Z and, when geometrical isomerism is possible, all geometrical isomers thereof are meant and, when tautomerism is possible, all tautomers thereof are meant.

The groups belonging to a $X_0$ group and a X group will be exemplified in Table X.

TABLE X

| No. | Group |
|---|---|
| X-1 | —$CH_3$ |
| X-2 | —$C_2H_5$ |
| X-3 | —$CF_3$ |
| X-4 | —CH=$CHCH_3$ |
| X-5 | —$CH_2$CH=$CH_2$ |
| X-6 | —C≡CH |
| X-7 | —F |
| X-8 | —Cl |
| X-9 | —Br |
| X-10 | —$NO_2$ |
| X-11 | —CN |
| X-12 | —$OCH_3$ |
| X-13 | —$SCH_3$ |
| X-14 | —$SOC_4H_9$ |
| X-15 | —$SO_2C_4H_9$ |
| X-16 | —$OCHF_2$ |
| X-17 | —$OCF_3$ |
| X-18 | —$OCF_2CHF_2$ |
| X-19 | —$SCF_3$ |
| X-20 | —$CH_2OCH_3$ |
| X-21 | —$COCH_3$ |
| X-22 | —$OCOCH_3$ |
| X-23 | —COOH |
| X-24 | —$COOCH_3$ |
| X-25 | —CH=CHCOOH |
| X-26 | —$N(CH_3)_2$ |
| X-27 | —$NHCOCH_3$ |
| X-28 | —$NHCOOCH_3$ |
| X-29 | —$CONH_2$ |
| X-30 | —$CON(CH_3)_2$ |
| X-31 | —$NHCON(CH_3)_2$ |
| X-32 | —NHC(=NH)$NH_2$ |
| X-33 | —$NHSO_2CF_3$ |
| X-34 | —$SO_2N(CH_3)_2$ |

The groups belonging to a $Y_0$ group and a Y group will be exemplified in Table Y.

TABLE Y

| No. | Group |
|---|---|
| Y-1 | morpholine (N, O-containing six-membered ring) |
| Y-2 | N-ethylpyrrole |
| Y-3 | N-methyl-oxazolidinone |
| Y-4 | 2-methyl-1,3-dioxolane |
| Y-5 | 2-methyl-1,3-dithiane |
| Y-6 | 1-methoxy-3-methylbenzene |

TABLE Y-continued

| No. | Group |
|---|---|
| Y-7 | 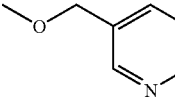 |
| Y-8 | 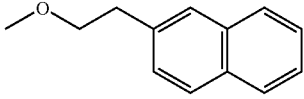 |
| Y-9 | 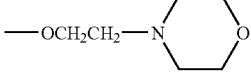 |
| Y-10 | 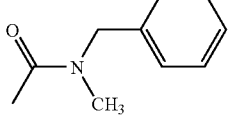 |

An A ring fused with a $Z_0$ group or a Z group will be exemplified in Table Z.

TABLE Z

| No. | Group |
|---|---|
| Z-1 | 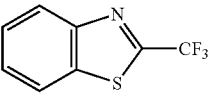 |
| Z-2 | 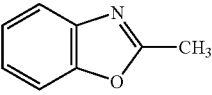 |
| Z-3 | 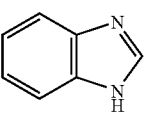 |
| Z-4 | 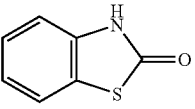 |
| Z-5 | 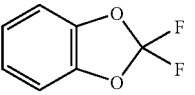 |
| Z-6 | 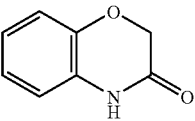 [SMILES: O=C1COc2ccccc2N1] |
| Z-7 | 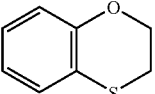 |
| Z-8 | 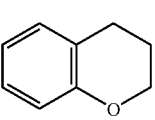 |

TABLE Z-continued

| No. | Group |
|---|---|
| Z-9 | 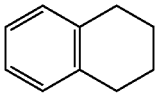 |
| Z-10 | 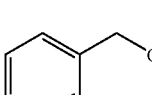 |

$Q_{A0}$ and $Q_A$ will be exemplified in Table Q.

TABLE Q

| No. | Group |
|---|---|
| Q-1 | —OH |
| Q-2 |  |
| Q-3 | 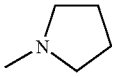 |
| Q-4 | 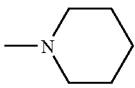 |
| Q-5 | —OCOCH$_3$ |
| Q-6 | —OSO$_2$N(CH$_3$)$_2$ |
| Q-7 | —NHCH$_2$CH=CH$_2$ |
| Q-8 | —NHCH$_2$C≡CH |
| Q-9 | —NHCH$_2$CH$_2$OCH$_3$ |
| Q-10 | —OCH$_3$ |
| Q-11 | —OCH$_2$CH$_2$ (c) C$_6$H$_{11}$ |
| Q-12 | —OCH$_2$CH=CH$_2$ |
| Q-13 | —OCH$_2$C≡CH |
| Q-14 | —OCH$_2$COOH |
| Q-15 | —OCH$_2$COOCH$_3$ |
| Q-16 | —OCH$_2$CONH$_2$ |
| Q-17 | —OCH$_2$CN |
| Q-18 | —OCH$_2$CH$_2$OH |
| Q-19 | —OCH$_2$CH$_2$OCH$_3$ |
| Q-20 | —OCH$_2$CH$_2$N(CH$_3$)$_2$ |
| Q-21 | —OCH$_2$COCH$_3$ |
| Q-22 | —OCOC$_6$H$_5$ |
| Q-23 | —OCH$_2$C$_6$H$_5$ |
| Q-24 | 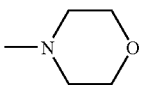 |
| Q-25 |  |
| Q-26 | 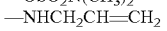 |

$T_{A0}$ and $T_A$ will be exemplified in Table T.

TABLE T

| No. | Group |
|---|---|
| T-1 | —H |
| T-2 | —CH$_3$ |
| T-3 | —CH$_2$CH$_2$ (c) C$_6$H$_{11}$ |
| T-4 | —CH$_2$CH=CH$_2$ |
| T-5 | —CH$_2$C≡CH |
| T-6 | —CH$_2$C$_6$H$_5$ |
| T-7 | —CH$_2$COOH |
| T-8 | —CH$_2$COOCH$_3$ |
| T-9 | —CH$_2$CONH$_2$ |
| T-10 | —CH$_2$CN |
| T-11 | —CH$_2$CH$_2$OH |
| T-12 | —CH$_2$CH$_2$OCH$_3$ |
| T-13 | —CH$_2$CH$_2$N(CH$_3$)$_2$ |
| T-14 | —CH$_2$COCH$_3$ |
| T-15 | —CH$_2$CF$_3$ |
| T-16 | —Ph |
| T-17 | (2-pyridyl) |

Examples of the present compound (I) include the compound wherein $Q_\alpha$ is a hydroxy group, a (b)-group ((b$_0$) is as defined above) or an $A_9$'-O-group ($A_9$' is as defined above) and, at the same time, $K_a$ is a hydrogen atom and $L_a$ is a methyl group, or $K_a$ and $L_a$ form a 1,3-butadienylene group.

Examples of the present compound (II) include the compound wherein $Q_{A0}$ is a hydroxy group, a (b$_0$)-group ((b$_0$) is as defined above) or an ($A_9$'-O-group ($A_9$' is as defined above) and, at the same time, $K_{A0}$ is a hydrogen atom and $L_{A0}$ is a methyl group, or $K_{A0}$ and $L_{A0}$ form a 1,3-butadienylene group.

Examples of the present compound (III) include the compound wherein $Q_A$ is a hydroxy group, a (b)-group ((b) is as defined above) or an $Q_9$'-O-group ($A_9$' is as defined above) and, at the same time, $K_A$ is a hydrogen atom and $L_A$ is a methyl group, or $K_A$ and $L_A$ form a 1,3-butadienylene group.

Examples of the present compound (IV) include the compound wherein $Q_A$ is a hydroxy group, a (b)-group ((b) is as defined above) or an $A_9$'-O-group ($A_9$' is as defined above) and, at the same time, $K_a$ is a hydrogen atom and $L_a$ is a methyl group.

Examples of the present compound (X) include the compound wherein $Q_A$ is a hydroxy group, a (b)-group ((b) is as defined above) or an $A_9$'-O-group ($A_9$' is as defined above) and, at the same time, r is 0.

Examples of the present compound (XV) include the compound wherein $Q_A$ is a hydroxy group, a (b)-group ((b) is as defined above) or an $A_9$'-O-group ($A_9$' is as defined above) and, at the same time, $K_a$ is a hydrogen atom and $L_a$ is a methyl group.

Examples of the present compound (XIX) include the case where $Q_A$ is a hydroxy group, a (b)-group ((b) is as defined above) or an $A_9$'-O-group ($A_9$' is as defined above) and, at the same time, r is 0.

Some of the present compounds are described in documents such as Tetrahedron (1973), 29, 1083, WO 01/79187, Zhurnal Prikladnoi Spektroskopii (1967), 7,638), Khimiya Geterotsiklicheskikh Soedinenii (1967), 4, 682, Chemical Papers (1997), 51, 33 and Synthetic Communications (2000), 30, 2735, and is known. However, in these publications, there is no description about the effect of suppressing transcription of I type collagen gene in a tissue, in its turn, the effect of suppressing an accumulated amount of collagen.

The present compounds (V), (VI), (XI), (XII), (XVI) and (XX) are novel compounds. Although WO 97/35565, JP09227547, WO 00/20371, JP2002371078, WO 01/79187 and WO 92/18483 disclose compounds having a certain conceptional skeleton, there is no specific description of a compound having a similar structure as that of the present compound. In addition, in the publications, there is no description regarding the effect of suppressing transcription of I type collagen gene in a tissue, in its turn, the effect of suppressing an accumulated amount of collagen.

The present compound (I) can be produced by reacting a compound represented by the formula ($\alpha$) (wherein A, $Y_a$ and q are as defined above) and a compound represented by the formula ($\alpha$') (wherein $Q_a$, $W_a$, $K_a$ and $L_a$ are as defined above) (see Russian J. General Chem. (2001), 71, 1257, Indian J. Chem. (1974), 12, 956 and JP50046666).

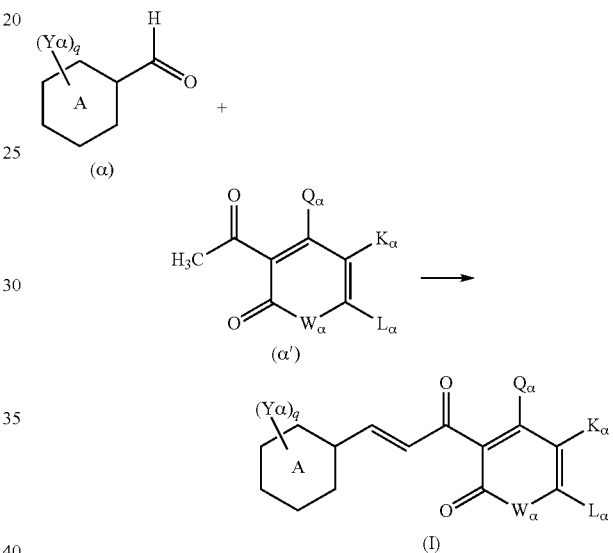

The present compound (II) can be produced by reacting a compound represented by the formula (A0) (wherein A, $Y_{A0}$ and q are as defined above) and a compound represented by the formula (A$_0$') (wherein $Q_{A0}$, $W_{A0}$, $K_{A0}$ and $L_{A0}$ are as defined above), as described above.

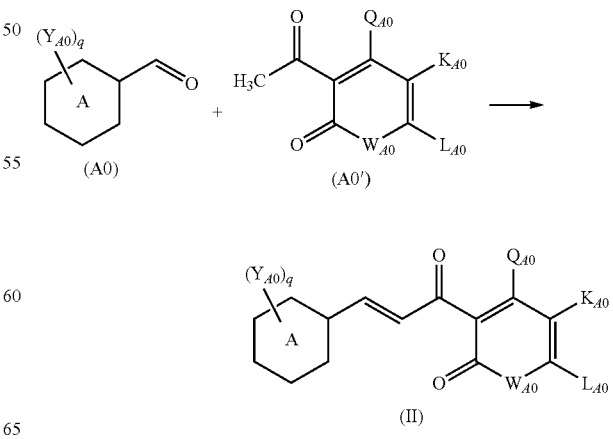

Among the present compounds, a cinnamoyl compound represented by the formula (II-1):

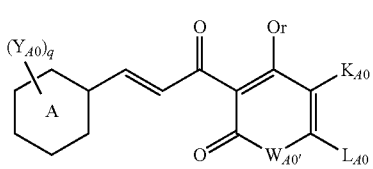

[wherein A, $Y_{A0}$, q, $K_{A0}$ and $L_{A0}$ are as defined above, r represents an $A_9'$-group ($A_9'$ is as defined above), $W_{A0}'$ represents an oxygen atom or a —$NT_A'$-group {$T_A'$ represents an $A_9'$-group ($A_9'$ is as defined above), a $D_5$-$R_4$-group ($D_5$ and $R_4$ are as defined above) or a $M_c$-group ($M_c$ is as defined above)}] can be produced by reacting a cinnamoyl compound represented by the formula (II-2):

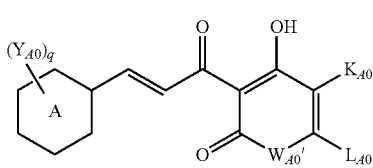

[wherein A, $Y_{A0}$, q, $K_{A0}$, $L_{A0}$ and $W_{A0}'$ are as defined above] (hereinafter, referred to as the present intermediate (II-2) in some cases) with a compound represented by the formula (II-3):

r-V         (II-3)

[r is as defined above, and V represents a leaving group.]

Examples of the reaction method include a method wherein the present intermediate (II-2) is reacted with a compound (II-3) in the presence of a base.

The reaction of the present intermediate (II-2) and a compound (II-3) in the presence of a base is performed usually in a solvent. Examples of the solvent used in the reaction include acid amides such as N,N-dimethylformamide, N,N-dimethylacetamide and the like, sulfoxides such as dimethyl sulfoxide and the like, phosphoric acid amide compounds such as hexamethylphosphoramide and the like, and ketones such as acetone, methyl ethyl ketone and the like.

Examples of the base used in the reaction include alkali metal hydroxides such as sodium hydroxide, potassium hydroxide and the like, and carbonates of an alkali metal such as sodium carbonate, potassium carbonate and the like.

Examples of the compound (II-3) include alkylsulfonic acid esters such as methyl methanesulfonate and the like, arylsulfonic acid esters such as p-toluenesulfonic acid methyl ester, p-toluenesulfonic acid 2-methoxyethyl ester and the like, sulfate esters such as dimethyl sulfate and the like, and halides such as methyl iodide, 2-chloroethyldimethylamine, allyl bromide, propargyl bromide, methyl bromoacetate, bromoacetonitrile, 2-bromoethanol, benzyl bromide, bromoacetone and the like.

The amount of the reagent used in the reaction is such a ratio that a base is usually 1 mole to 2 moles, and a compound (II-3) is usually 1 mole to 2 moles per 1 mole of the present intermediate (II-2).

The reaction temperature is usually in a range of 0° C. to 100° C., and a reaction time is usually in a range of 1 hour to 20 hours.

After completion of the reaction, the reaction mixture is extracted with an organic solvent, and the organic layer is subjected to a post-treatment procedure such as drying, concentration and the like, thereby, a cinnamoyl compound (II-1) can be isolated. The isolated cinnamoyl compound (II-1) can be also further purified by chromatography, recrystallization or the like.

The present intermediate (VI) can be produced by reacting a compound represented by the formula (VI-1) (wherein A, $X_c$, $Y_c$, p and q are as defined above) and a compound represented by the formula (VI-2) (wherein $K_a$ and $L_a$ are as defined above) as in the reaction of the compound (A0) and the compound (A0').

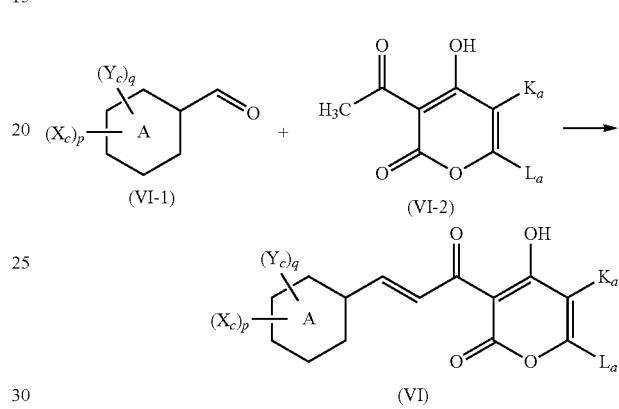

The present intermediate (XII) can be produced by reacting a compound represented by the formula (XII-1) (wherein A, $X_e$, $Y_e$, p and q are as defined above) and a compound represented by the formula (XII-2) (wherein $M_a'$ and r are as defined above) as in the reaction of a compound (A0) and a compound (A0').

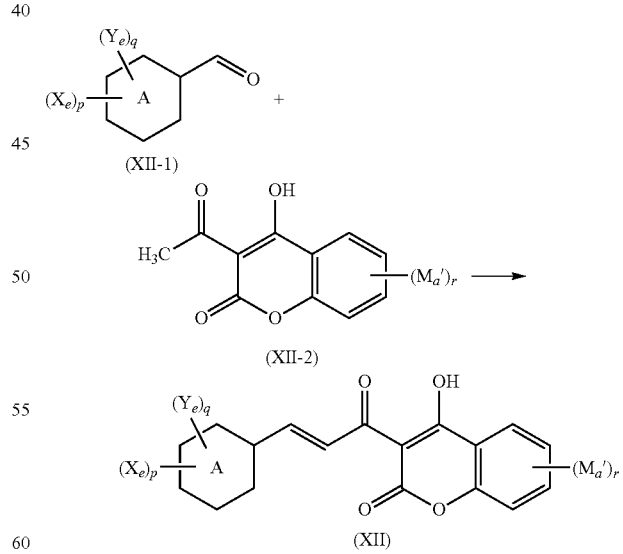

Among the present compounds, a 2H-pyran-2-one compound represented by the formula (VI-3) can be produced by reacting the present intermediate (VI) and the compound (II-3). The reaction can be performed as in the reaction of the present intermediate (II-2) and the compound (II-3).

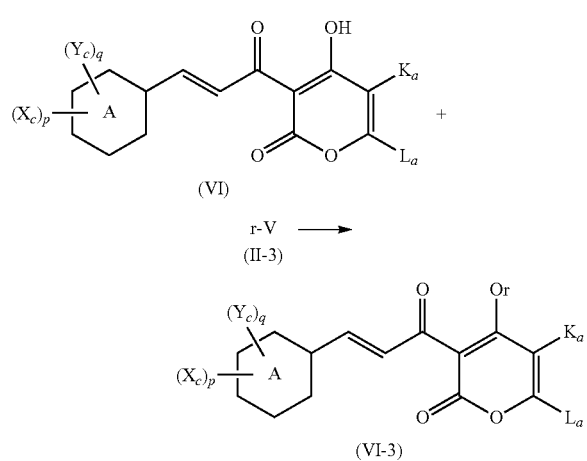

Among the present compounds, a 2H-1-benzopyran-3-one compound represented by the formula (XII-3) can be produced by reacting the present intermediate (XII) and the compound (II-3). The reaction can be performed as in the reaction of the present intermediate (II-2) and the compound (II-3).

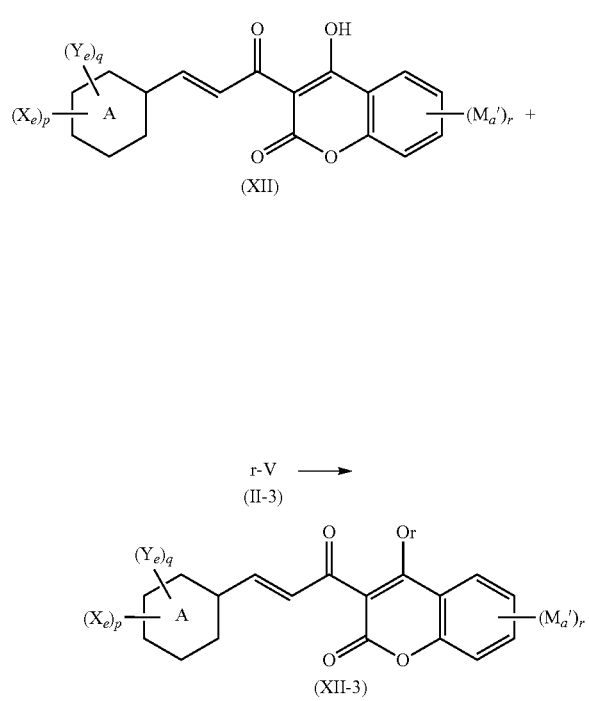

The present intermediates (VI) and (XII) are novel compounds. Although WO 97/35565, JP09227547, WO 00/20371, JP2002371078, WO 01/79187 and WO 92/18483 disclose compounds having a certain conceptional skeleton, there is no specific description of a compound having a similar structure as that of the present intermediates (VI) and (XII).

Among the present intermediate (II-2), the present intermediate (II-2a) represented by compound numbers (1a-1) to (1a-12) will be exemplified in Table 1a.

TABLE 1a

The present intermediate (II-2a)

(II-2a)

| Compound No. | $(Y_{A0})_q$ |
|---|---|
| (1a-1) | 3-CH=CHCH$_3$ |
| (1a-2) | 3-C≡CH |
| (1a-3) | 3-CON(CH$_3$)$_2$ |
| (1a-4) | 3-CH$_3$, 4-OCH$_3$ |
| (1a-5) | 3-CF$_3$, 4-Cl |
| (1a-6) | 3-Cl, 4-OCF$_3$ |
| (1a-7) | 3-F, 4,5-(OCH$_3$)$_2$ |
| (1a-8) | 3-COOCH$_3$ |

| Compound No. | $(Y_{A0})_q$ structure |
|---|---|
| (1a-9) | (1,3-dioxolane meta-methylphenyl) |
| (1a-10) | (2,3-dihydro-1,4-benzodioxine methyl) |
| (1a-11) | (oxazolidinone N-methylphenyl) |
| (1a-12) | (morpholinoethoxy methylphenyl) |

Among the present intermediate (II-2), the present intermediate (II-2b) represented by a compound number (1b-1) to (1b-4) will be exemplified in Table 1b.

TABLE 1b

The present intermediate (II-2b)

(II-2b) [Structure: H₃C-substituted phenyl-CH=CH-C(=O)- attached to pyranone ring with OH, K_{A0}, L_{A0} substituents]

| Compound No. | The present intermediate (II-2b) |
|---|---|
| (1b-1) | [Structure with H₃C-phenyl-CH=CH-C(=O)- attached to pyranone with OH, Br, CH₃] |
| (1b-2) | [Structure with H₃C-phenyl-CH=CH-C(=O)- attached to pyranone with OH, CH₃, CH₃] |
| (1b-3) | [Structure with H₃C-phenyl-CH=CH-C(=O)- attached to fused bicyclic pyranone with OH] |
| (1b-4) | [Structure with H₃C-phenyl-CH=CH-C(=O)- attached to pyranone with OH and phenyl] |

Among the present intermediate (II-2), the present intermediate (II-2c) represented by a compound number (1c-1) to (1c-12) will be exemplified in Table 1c.

TABLE 1c

The present intermediate (II-2c)

(II-2c) [Structure: $(Y_{A0})_q$-substituted phenyl-CH=CH-C(=O)- attached to coumarin with OH]

| Compound No. | $(Y_{A0})_q$ |
|---|---|
| (1c-1) | 3-CH=CHCH₃ |
| (1c-2) | 3-C≡CH |
| (1c-3) | 3-CON(CH₃)₂ |
| (1c-4) | 3-CH₃, 4-OCH₃ |
| (1c-5) | 3-CF₃, 4-Cl |
| (1c-6) | 3-Cl, 4-OCF₃ |

TABLE 1c-continued

The present intermediate (II-2c)

(II-2c) [Structure: $(Y_{A0})_q$-substituted phenyl-CH=CH-C(=O)- attached to coumarin with OH]

| (1c-7) | 3-F, 4,5-(OCH₃)₂ |
| (1c-8) | 3-COOCH₃ |

| Compound No. | $(Y_{A0})_q$ phenyl structure |
|---|---|
| (1c-9) | [1,3-dioxolane attached to 3-methylphenyl] |
| (1c-10) | [2,3-dihydro-1,4-benzodioxine with methyl] |
| (1c-11) | [oxazolidinone N-attached to 3-methylphenyl] |
| (1c-12) | [morpholine-N-CH₂CH₂-O-(3-methylphenyl)] |

Among the present compound (II), the present compound (IIa) represented by a compound number (2a-1) to (2a-28) will be exemplified in Table 2a.

TABLE 2a

The present compound (IIa)

(IIa)

[Structure: (Y$_{A0}$)$_q$-phenyl-CH=CH-C(=O)- attached to a 2H-pyran-2-one ring with 4-Or and 6-CH$_3$ substituents]

| Compound No. | (Y$_{AO}$)$_q$ | r |
|---|---|---|
| (2a-1) | 3-CH=CHCH$_3$ | CH$_3$ |
| (2a-2) | 3-C≡CH | C$_2$H$_5$ |
| (2a-3) | 4-SCH$_3$ | CH$_3$ |
| (2a-4) | 4-S(O)CH$_3$ | CH$_3$ |
| (2a-5) | 4-S(O)$_2$CH$_3$ | CH$_3$ |
| (2a-6) | 3-CN | CH$_3$ |
| (2a-7) | 4-COOH | CH$_2$CH=CH$_2$ |
| (2a-8) | 4-COOCH$_3$ | CH$_3$ |
| (2a-9) | 4-N(CH$_3$)$_2$ | CH$_3$ |
| (2a-10) | 3-NHCOCH$_3$ | CH$_2$C≡CH |
| (2a-11) | 3-NHCON(CH$_3$)$_2$ | CH$_3$ |
| (2a-12) | 3-CONH$_2$ | CH$_3$ |
| (2a-13) | 3-CON(CH$_3$)$_2$ | CH$_3$ |
| (2a-14) | 3, 4-Cl$_2$ | CH$_3$ |
| (2a-15) | 3-CH$_3$, 4-OCH$_3$ | CH$_3$ |
| (2a-16) | 3-CF$_3$, 4-Cl | CH$_3$ |
| (2a-17) | 3-Cl, 4-OCF$_3$ | CH$_3$ |
| (2a-18) | 3-F ,4,5-(OCH$_3$)$_2$ | CH$_3$ |
| (2a-19) | 3-COOCH$_3$ | CH$_3$ |

| Compound No. | (Y$_{A0}$)$_q$-phenyl structure | r |
|---|---|---|
| (2a-20) | 2-(3-methylphenyl)-1,3-dioxolane | CH$_3$ |
| (2a-21) | 6-methyl-2,3-dihydro-1,4-benzodioxine | CH$_3$ |
| (2a-22) | 3-(3-methylphenyl)-1,3-oxazolidin-2-one | CH$_3$ |
| (2a-23) | 4-[2-(3-methylphenoxy)ethyl]morpholine | CH$_3$ |
| (2a-24) | 3-CH$_3$ | CH$_2$CH$_2$OCH$_3$ |
| (2a-25) | 3-CH$_3$ | CH$_2$COOCH$_3$ |
| (2a-26) | 3-CH$_3$ | CH$_2$CH$_2$CH$_2$COCH$_3$ |
| (2a-27) | 3-CH$_3$ | CH$_2$CH$_2$OH |
| (2a-28) | 3-CH$_3$ | CH$_2$CH$_2$S(O)$_2$CH$_3$ |

Among the present compound (II), the present compound (IIb) represented by a compound number (2b-1) to (2b-3) will be exemplified in Table 2b.

TABLE 2b

The present compound (IIb)

(IIb) — structure: H3C-phenyl-CH=CH-C(=O)- attached to pyranone ring with OCH3, K_{A0}, L_{A0}, O, =O

| Compound No. | The present compound (IIb) |
|---|---|
| (2b-1) | structure with Br and CH3 substituents |
| (2b-2) | structure with CH3 and CH3 substituents |
| (2b-3) | fused bicyclic pyranone structure |

Among the present compound (II), the present compound (IIc) represented by a compound number (2c-1) to (2c-23) will be exemplified in Table 2c.

TABLE 2c

The present compound (IIc)

(IIc) — structure: $(Y_{A0})_q$-phenyl-CH=CH-C(=O)- attached to coumarin-like ring with Or substituent

| Compound No. | $(Y_{A0})_q$ | r |
|---|---|---|
| (2c-1) | 3-CH=CHCH$_3$ | CH$_3$ |
| (2c-2) | 3-C≡CH | C$_2$H$_5$ |
| (2c-3) | 4-SCH$_3$ | CH$_3$ |
| (2c-4) | 4-S(O)CH$_3$ | CH$_3$ |
| (2c-5) | 4-S(O)$_2$CH$_3$ | CH$_3$ |
| (2c-6) | 3-CN | CH$_3$ |
| (2c-7) | 4-COOH | CH$_2$CH=CH$_2$ |
| (2c-8) | 4-COOCH$_3$ | CH$_3$ |
| (2c-9) | 4-N(CH$_3$)$_2$ | CH$_3$ |
| (2c-10) | 3-NHCOCH$_3$ | CH$_2$C≡CH |
| (2c-11) | 3-NHCON(CH$_3$)$_2$ | CH$_3$ |
| (2c-12) | 3-CONH$_2$ | CH$_3$ |
| (2c-13) | 3-CON(CH$_3$)$_2$ | CH$_3$ |
| (2c-14) | 3, 4-Cl$_2$ | CH$_3$ |
| (2c-15) | 3-CH$_3$, 4-OCH$_3$ | CH$_3$ |
| (2c-16) | 3-CF$_3$, 4-Cl | CH$_3$ |
| (2c-17) | 3-Cl, 4-OCF$_3$ | CH$_3$ |
| (2c-18) | 3-F, 4,5-(OCH$_3$)$_2$ | CH$_3$ |
| (2c-19) | 3-COOCH$_3$ | CH$_3$ |

TABLE 2c-continued

The present compound (IIc)

| Compound No. | $(Y_{A0})_q$ | r |
|---|---|---|
| (2c-20) | 3-(1,3-dioxolan-2-yl) | CH$_3$ |
| (2c-21) | 2,3-dihydro-1,4-benzodioxin-6-yl substituent | CH$_3$ |
| (2c-22) | 3-(2-oxo-1,3-oxazolidin-3-yl) | CH$_3$ |
| (2c-23) | 3-O-CH$_2$CH$_2$-morpholino | CH$_3$ |

Among the present compound (II), the present compound (IIa') represented by a compound number (3a-1) to (3a-40) will be exemplified in Table 3a.

TABLE 3a

The present compound (IIa')

(IIa') — structure: $(Y_{A0})_q$-phenyl-CH=CH-C(=O)- attached to pyridinone ring with Or, CH$_3$, N-r'

| Compound No. | $(Y_{A0})_q$ | r | r' |
|---|---|---|---|
| (3a-1) | H | H | H |
| (3a-2) | H | H | CH$_3$ |
| (3a-3) | H | CH$_3$ | CH$_3$ |
| (3a-4) | 3-Cl | H | H |
| (3a-5) | 3-CH$_3$ | H | H |
| (3a-6) | 4-CF$_3$ | H | H |
| (3a-7) | 3-CH$_2$OCH$_3$ | H | H |
| (3a-8) | 3-CH=CHCH$_3$ | H | H |
| (3a-9) | 3-C≡CH | H | H |
| (3a-10) | 3-OC$_2$H$_5$ | H | H |
| (3a-11) | 4-SCH$_3$ | H | H |
| (3a-12) | 4-S(O)CH$_3$ | H | H |

TABLE 3a-continued

The present compound (IIa')

(IIa')

| Compound No. | (Y_{A0})_q-phenyl substituent | r | r' |
|---|---|---|---|
| (3a-13) | 4-S(O)$_2$CH$_3$ | H | H |
| (3a-14) | 4-NO$_2$ | H | H |
| (3a-15) | 3-CN | H | H |
| (3a-16) | 4-COOH | H | H |
| (3a-17) | 4-COOCH$_3$ | H | H |
| (3a-18) | 4-N(CH$_3$)$_2$ | H | H |
| (3a-19) | 3-NHCOCH$_3$ | H | H |
| (3a-20) | 3-NHCON(CH$_3$)$_2$ | H | H |
| (3a-21) | 3-CONH$_2$ | H | H |
| (3a-22) | 3-CON(CH$_3$)$_2$ | H | H |
| (3a-23) | 3-OCHF$_2$ | H | H |
| (3a-24) | 4-OCF$_3$ | H | H |
| (3a-25) | 4-OCF$_2$CHF$_2$ | H | H |
| (3a-26) | 2-SCF$_3$ | H | H |
| (3a-27) | 3,4-Cl$_2$ | H | H |
| (3a-28) | 2,4-(OCH$_3$)$_2$ | H | H |
| (3a-29) | 3-CH$_3$, 4-OCH$_3$ | H | H |
| (3a-30) | 3-OC$_2$H$_5$, 4-OH | H | H |
| (3a-31) | 3-CF$_3$, 4-Cl | H | H |
| (3a-32) | 3-Cl, 4-OCF$_3$ | H | H |
| (3a-33) | 3-F, 4,5-(OCH$_3$)$_2$ | H | H |
| (3a-34) | 3-COOCH$_3$ | H | CH$_3$ |

| Compound No. | (Y_{A0})_q-phenyl structure | r | r' |
|---|---|---|---|
| (3a-35) | 2-(1,3-dioxolan-2-yl)-phenyl | H | CH$_3$ |
| (3a-36) | 2,3-dihydro-1,4-benzodioxin-6-yl | H | CH$_3$ |
| (3a-37) | 3-(2-oxo-oxazolidin-3-yl)-phenyl | H | H |
| (3a-38) | 3-(2-oxo-oxazolidin-3-yl)-phenyl | H | CH$_3$ |
| (3a-39) | 3-(2-morpholinoethoxy)-phenyl | H | H |
| (3a-40) | 3-(2-morpholinoethoxy)-phenyl | H | CH$_3$ |

Among the present compound (II), the present compound (IIb') represented by a compound number (3b-1) to (3b-3) will be exemplified in Table 3b.

TABLE 3b

The present compound (IIb')

(IIb')

| Compound No. | The present compound (IIb') |
|---|---|
| (3b-1) | K$_{A0}$ = Br, L$_{A0}$ = CH$_3$ |
| (3b-2) | K$_{A0}$ = CH$_3$, L$_{A0}$ = CH$_3$ |
| (3b-3) | fused cyclohexane ring |

Among the present compound (II), the present compound (IIc') represented by a compound number (3c-1) to (3c-40) will be exemplified in Table 3c.

TABLE 3c

The present compound (IIc')

(IIc')

| Compound No. | $(Y_{A0})_q$ | r | r' |
|---|---|---|---|
| (3c-1) | H | H | H |
| (3c-2) | H | H | $CH_3$ |
| (3c-3) | H | $CH_3$ | $CH_3$ |
| (3c-4) | 3-Cl | H | H |
| (3c-5) | 3-$CH_3$ | H | H |
| (3c-6) | 4-$CF_3$ | H | H |
| (3c-7) | 3-$CH_2OCH_3$ | H | H |
| (3c-8) | 3-CH=$CHCH_3$ | H | H |
| (3c-9) | 3-C≡CH | H | H |
| (3c-10) | 3-$OC_2H_5$ | H | H |
| (3c-11) | 4-$SCH_3$ | H | H |
| (3c-12) | 4-S(O)$CH_3$ | H | H |
| (3c-13) | 4-S(O)$_2$$CH_3$ | H | H |
| (3c-14) | 4-$NO_2$ | H | H |
| (3c-15) | 3-CN | H | H |
| (3c-16) | 4-COOH | H | H |
| (3c-17) | 4-COO$CH_3$ | H | H |
| (3c-18) | 4-N($CH_3$)$_2$ | H | H |
| (3c-19) | 3-NHCO$CH_3$ | H | H |
| (3c-20) | 3-NHCON($CH_3$)$_2$ | H | H |
| (3c-21) | 3-CON$H_2$ | H | H |
| (3c-22) | 3-CON($CH_3$)$_2$ | H | H |
| (3c-23) | 3-OCH$F_2$ | H | H |
| (3c-24) | 4-O$CF_3$ | H | H |
| (3c-25) | 3-O$CF_2$CH$F_2$ | H | H |
| (3c-26) | 2-S$CF_3$ | H | H |
| (3c-27) | 3,4-$Cl_2$ | H | H |
| (3c-28) | 2,4-(O$CH_3$)$_2$ | H | H |
| (3c-29) | 3-$CH_3$, 4-O$CH_3$ | H | H |
| (3c-30) | 3-O$C_2H_5$, 44-OH | H | H |
| (3c-31) | 3-$CF_3$, 4-Cl | H | H |
| (3c-32) | 3-Cl, 4-O$CF_3$ | H | H |
| (3c-33) | 3-F, 4,5-(O$CH_3$)$_2$ | H | H |
| (3c-34) | 3-COO$CH_3$ | H | $CH_3$ |

| Compound No. | (structure) | r | r' |
|---|---|---|---|
| (3c-35) | (1,3-dioxolan-2-yl on 3-methylphenyl) | H | $CH_3$ |
| (3c-36) | (2,3-dihydro-1,4-benzodioxin-6-yl, methyl) | H | $CH_3$ |
| (3c-37) | (oxazolidin-2-one-N-yl on 3-methylphenyl) | H | H |
| (3c-38) | (oxazolidin-2-one-N-yl on 3-methylphenyl) | H | $CH_3$ |
| (3c-39) | (morpholinoethoxy on 3-methylphenyl) | H | H |
| (3c-40) | (morpholinoethoxy on 3-methylphenyl) | H | $CH_3$ |

The present compound has the ability to suppress transcription of a Type I collagen gene. The ability is important in improving tissue fibrosis because it decreases expression of a Type I collagen gene to induce a reduction in accumulation of collagen. Therefore, the present compound can be utilized as an active ingredient of a composition (medicament, cosmetic, food additive etc.) which can improve tissue fibrosis by decreasing expression of a Type I collagen gene to induce a reduction in accumulation of collagen.

A disease to which the transcription-suppressing composition of the present invention and the fibrosis-improving composition of the present invention can be applied includes, for example, a disease in which excessive accumulation of collagen causes fibrosis and then sclerosis of tissues, resulting in decreased function, cicatrization and the like in the tissues such as organs (i.e. fibrosing disease etc.). Specifically, the disease includes diseases and disorders such as hepatic cirrhosis, interstitial pulmonary disease, chronic renal failure (or disease resulting in chronic renal failure), hyperplasia scar after inflammation, postoperative scars or burn scars, scleroderma, arteriosclerosis, hypertension and the like. Incidentally, as an example of hepatic cirrhosis, it has been already known that C type or B type hepatitis virus induces chronic inflammation and then increased production of TGF-β, and thereby, hepatic fibrosis (particularly, accumulation of type I and type III collagen) is induced to cause hepatic cirrhosis (e.g. see Clin. Liver Dis., 7, 195-210 (2003)). As an example of interstitial pulmonary disease, it has been thought that pneumonia caused by mites, viruses, tubercle bacilli or the like induces increased production of TGF-β and then pulmonary fibrosis, and thereby interstitial pulmonary disease is caused. For chronic renal failure such as diabetic nephropathy and IgA nephropathy, it has been already suggested that diabetic nephropathy is caused by increased level of TGF-β in renal glomeruli due to hyperglycemia and thereby induction of renal fibrosis (particularly accumulation of Type I and Type IV collagen), and IgA nephropathy is caused by induction of nephritis due to accumulation of IgA in renal glomeruli followed by increased level of TGF-β, and thereby induction of renal fibrosis (particularly accumulation of Type I and Type IV collagen) (e.g. see Am. J. Physiol. Renal Phsiol., 278, F830-F838 (2000), Kidney Int. 64.149-159 (2003)). A db/db mouse, a diabetic nephropathy model animal, develops hyperglycemia by overeating because it has a mutation in a leptin receptor for suppressing ingestion, and then spontaneously develops diabetes. In the db/db mouse, the blood glucose concentration is about 4 times higher than a normal mouse, and fibrosis of renal glomeruli and increased level of TGF-β are found (e.g. see Am. J. Pathol., 158, 1653-1663 (2001)). An anti-Thy-1 rat, an IgA nephropathy model animal, is produced by administering an anti-Thy-1 antibody to a normal rat to artificially cause renal fibrosis. It has been shown that renal fibrosis is suppressed by administering an anti-TGF-β receptor antibody to the model animal (e.g. see Kidney Int., 60, 1745-1755 (2001)). Although the cause of scleroderma is unknown, it has been found that skin fibrosis is improved by administering a TGF-β inhibitor to a Tsk mouse, which is a model animal therefor (e.g. see J. Invest. Dermatol., 118.461-470 (2001)). Thus, a compound which suppresses the activity of TGF-β can be utilized as an active ingredient of a composition (medicament, cosmetic, food additive etc.) for inhibiting the collagen synthesis-promoting activity of TGF-β to suppress tissue fibrosis and thereby providing a fibrosing disease therapeutic effect.

Such transcription-suppressing composition and fibrosis-improving composition of the present invention comprise the present compound and an inert carrier. Such composition usually comprises 0.01% by weight to 99.99% by weight of the present compound and 99.99% by weight to 0.01% by weight of an inert carrier. The inert carrier is a pharmaceutically acceptable carrier or excipient. The transcription-suppressing composition and fibrosis-improving composition of the present invention may further comprise pharmaceutical additives, cosmetic additives, food additives and the like.

The present compound also inhibits the ability of TGF-β to promote transcription of a Type I collagen gene, as shown in Example 22 below. That is, the present compound is a TGF-β antagonist having the ability to suppress the activity of TGF-β. Therefore, the present compound can be also utilized as an active ingredient of a composition for suppressing the activity of TGF-β. It has been known that TGF-β has the ability to promote transition from a growth phase (hereinafter, also referred to as hair growth phase in some cases) to a regression phase (hereinafter, also referred to as a hair regression phase in some cases) in the hair life cycle [J. Invest. Dermatol., 111, 948-954 (1998), FASEB J., 16, 1967-1969 (2002)]. Further, it has been reported that an anti-TGF-β antibody, Fetuin, which is a TGF-β inhibitor, and the like antagonize the suppressing-activity of TGF-β on hair extension and exhibit a promoting-effect on hair extension [J. Invest. Dermaton., 118, 993-997 (2002), JP-A 2000-342296]. Therefore, the present compound (and a TGF-β activity-suppressing composition containing the present compound as an active ingredient) may be utilized for inhibiting a promoting effect of TGF-β on transition to a hair regression phase to induce extension of a hair growth phase and thereby providing a hair-growing effect.

Such TGF-β suppressing composition and hair-growing composition of the present invention comprise the present compound and an inert carrier. Such composition usually comprises 0.01% by weight to 99.99% by weight of the present compound and 99.99% by weight to 0.01% by weight of an inert carrier. The inert carrier is a pharmaceutically acceptable carrier or excipient. The TGF-β suppressing composition and hair-growing composition of the present invention may further comprise pharmaceutical additives, cosmetic additives, food additives and the like.

A pharmaceutically acceptable carrier, excipient, pharmaceutical additive, food additive, cosmetic additive, a medicament additive, and the like contained in the above-described composition can be appropriately selected depending on the specific use thereof. In addition, the composition may be in a form of various solids, liquids and the like depending on the specific use thereof.

For example, when the present compound is used as an active ingredient of a medicament, specific examples of the medicament include oral preparations such as powders, fine granules, granules, tablets, syrups, capsules, suspensions, emulsions, extracts and pills; and parenteral preparations such as injections, transdermal absorbing agents such as external liquids and ointments, suppositories and local preparations.

Oral preparations can be prepared using carriers or excipients, and pharmaceutical additives such as binders, disintegrants, surfactants, lubricants, glidants, diluents, preservatives, coloring agents, flavors, stabilizers, humectants, antiseptics, antioxidants and the like, for example, gelatin, sodium alginate, starch, corn starch, white sugar, lactose, glucose, mannit, carboxymethylcellulose, dextrin, polyvinylpyrrolidone, crystalline cellulose, soybean lecithin, sucrose, fatty acid ester, talc, magnesium stearate, polyethylene glycol, magnesium silicate, anhydrous silicic acid and the like, according to a conventional method.

A dose of the oral preparation varies depending on the age, sex and weight of a mammal to be administered, the severity of disease, the kind and dosage form of the composition of the present invention, and the like. Usually, in the case of oral administration, about 1 mg to about 2 g per day, preferably about 5 mg to about 1 g per day of the active ingredient may be administered to an adult human. The daily dose may be also administered at one time or in several divided doses.

Among parenteral preparations, an injection can be prepared using such as a water-soluble solvent such as physiological saline or sterilized water Ringer solution, a water-insoluble solvent such as vegetable oil or fatty acid ester, an isotonic agent such as glucose or sodium chloride, pharmaceutical additives such as a solubilizer, a stabilizer, an antiseptic, a suspending agent and an emulsifying agent, and the like, according to a conventional method. A transdermal absorbing agent such as external liquid or a gel-like ointment, a suppository for rectal administration and the like can be also prepared according to a conventional method. For administering such parenteral preparations, they may be administered by injection (subcutaneously, intravenously etc.), transdermally, or rectally. A local preparation can be prepared, for example, by incorporating the present compound into a pellet of a sustained-release polymer such as ethylene vinyl acetate polymer. The pellet may be surgically transplanted into a tissue to be treated.

A dose of the parenteral preparation varies depending on the age, sex and weight of a mammal to be administered, the severity of disease, the kind and dosage form of the composition of the present invention, and the like. Usually, in the case of administration by injection, about 0.1 mg to about 500 mg of the active ingredient may be administered to an adult human. The daily dose may be also administered at one time or in several divided doses.

When the present compound is used by adding to cosmetics, specific examples of the form of a cosmetic with comprises the present compound include liquid, emulsion, cream, lotion, ointment, gel, aerosol, mousse and the like. Lotion can be prepared using cosmetic additives such as a suspending agent, an emulsifier, a preservative and the like, according to a conventional method.

A dose of the cosmetic varies depending on the age, sex and weight of a mammal to be administered, the severity of disease, the kind and dosage form of the composition of the present invention, and the like. Usually, about 0.01 mg to about 50 mg of the active ingredient may be administered to an adult human. The daily dose may be also administered at one time or in several divided doses.

When the present compound is used as a food additive, specific examples of the form of a food which comprises the additive include powder, a tablet, a beverage, an edible gel or a mixed liquid of the gel and syrup, for example, general beverage and food and luxury food and beverage such as seasonings, Japanese confectioneries, western confectioneries, ice confectioneries, beverage, spreads, pastes, pickles, bottled or canned products, processed domestic animal meats, processed fish meats or marine product, processed dairy or egg products, processed vegetables, processed fruits, processed cereals and the like. Alternatively, the present compound can be also added to feeds or provenders for rearing animals such as livestocks, poultry, honey bee, silkworm, fish and the like.

A dose of the food varies depending on the age, sex and weight of a mammal to be administered, the severity of disease, the kind and dosage form of the composition of the present invention, and the like. Usually, about 0.1 mg to about 500 mg of the active ingredient may be administered to an adult human. The daily dose may be also administered at one time or in several divided doses.

EXAMPLES

The present invention will be further specifically explained below by way of Examples.

Example 1

Synthesis of the Present Intermediate (II-2a)
[Compound No. (1a-6)]

A mixture of 1.85 g of 3-acetyl-4-hydroxy-6-methyl-2H-pyran-2-one, 2.25 g of 3-chloro-4-(trifluoromethoxy)benzaldehyde, 20 ml of chloroform and 0.7 ml of piperidine was heated under refluxing for 4 hours. After cooling to room temperature, the reaction mixture was concentrated under reduced pressure, and the residue was subjected to column chromatography. Resulting crystals were washed with 40 ml of t-butyl methyl ether to obtain 0.40 g of 4-hydroxy-3-[3-[3-chloro-4-(trifluoromethoxy)phenyl]-1-oxo-2-propenyl]-6-methyl-2H-pyran-2-one [Compound No. (1a-6)] as a yellow crystal.

$^1$H-NMR (300 MHz, CDCl$_3$) δ (ppm): 2.31 (s, 3H), 5.70 (s, 1H), 7.38 (d, 1H), 7.61 (d, 1H), 7.78 (s, 1H), 7.80 (d, 1H, J=15.0 Hz), 8.27 (d, 1H, J=15.0 Hz)

Example 2

Synthesis of the Present Intermediate (II-2a)
[Compound No. (1a-9)]

According to the same manner as that of Example 1 except that 2.57 g of 3-([1,3]dioxolan-2-yl)benzaldehyde was used in place of 3-chloro-4-(trifluoromethoxy)benzaldehyde, 0.38 g of 4-hydroxy-3-[3-[3-([1,3]dioxolan-2-yl)phenyl]-1-oxo-2-propenyl]-6-methyl-2H-pyran-2-one [Compound No. (1a-9)] was obtained as a pale yellow crystal.

$^1$H-NMR (400 MHz, CDCl$_3$) δ (ppm): 2.29 (s, 3H), 4.04-4.17 (m, 4H), 5.84 (s, 1H), 5.96 (s, 1H), 7.44 (t, 1H, J=7.7 Hz), 7.54 (d, 1H, J=7.6 Hz), 7.70 (d, 1H, J=7.8 Hz), 7.78 (s, 1H), 7.97 (d, 1H, J=15.9 Hz), 8.32 (d, 1H, J=15.9 Hz)

Example 3

Synthesis of the Present Intermediate (II-2a)
[Compound No. (1a-10)]

According to the same manner as that of Example 1 except that 4.97 g of 2,3-dihydro-1,4-benzodioxin-6-carbaldehyde was used in place of 3-chloro-4-(trifluoromethoxy)benzaldehyde, 0.50 g of 4-hydroxy-3-[3-(2,3-dihydro-1,4-benzodioxin-6-yl)-1-oxo-2-propenyl]-6-methyl-2H-pyran-2-one [Compound No. (1a-10)] was obtained as a pale yellow crystal.

$^1$H-NMR (300 MHz, CDCl$_3$) δ (ppm): 2.27 (s, 3H), 4.28-4.31 (m, 4H), 5.94 (s, 1H), 6.90 (d, 1H, J=8.1 Hz), 7.21-7.24 (m, 2H), 7.88 (d, 1H, J=15.6 Hz), 8.17 (d, 1H, J=15.6 Hz), 12.19 (s, 1H)

Example 4

Synthesis of the Present Intermediate (II-2b)
[Compound No. (1b-1)]

According to the same manner as that of Example 1 except that n-tolualdehyde was used in place of 3-chloro-4-(trifluoromethoxy)benzaldehyde, and 3-acetyl-5-bromo-4-hydroxy-6-methyl-2H-pyran-2-one was used in place of 3-acetyl-4-hydroxy-6-methyl-2H-pyran-2-one, 5-bromo-4-hydroxy-3-[3-(3-methylphenyl)-1-oxo-2-propenyl]-6-methyl-2H-pyran-2-one [Compound No. (1b-1)] was obtained as a pale yellow crystal.

$^1$H-NMR (400 MHz, CDCl$_3$) δ (ppm): 2.40 (s, 3H), 2.50 (s, 3H), 7.25-7.34 (m, 2H), 7.49-7.51 (m, 2H), 8.05 (d, 1H, J=15.9 Hz), 8.30 (d, 1H, J=15.9 Hz)

Example 5

Synthesis of the Present Intermediate (II-2b)
[Compound No. (1b-4)]

According to the same manner as that of Example 1 except that 3-acetyl-4-hydroxy-6-phenyl-2H-pyran-2-one was used in place of 3-acetyl-4-hydroxy-6-methyl-2H-pyran-2-one, 4-hydroxy-3-[3-(3-methylphenyl)-1-oxo-2-propenyl]-6-phenyl-2H-pyran-2-one [Compound No. (1b-4)] was obtained.

$^1$H-NMR (400 MHz, CDCl$_3$) δ (ppm): 2.40 (s, 3H), 6.59 (s, 1H), 7.22-7.28 (1H), 7.32 (t, 1H, J=7.6 Hz), 7.48-7.58 (m, 5H), 7.86-7.93 (m, 2H), 7.97 (d, 1H, J=15.6 Hz), 8.35 (d, 1H, J=15.8 Hz), 12.06 (s, 1H)

Example 6

Synthesis of the Present Intermediate (II-2c)
[Compound No. (1c-6)]

A mixture of 2.25 g of 3-acetyl-4-hydroxy-2H-1-benzopyran-2-one, 2.25 g of 3-chloro-4-(trifluoromethoxy)benzaldehyde, 20 ml of chloroform and 0.7 ml of piperidine was heated under refluxing for 2 hours and 30 minutes. After cooled to room temperature, the reaction mixture was concentrated under reduced pressure, and the residue was subjected to column chromatography. Resulting crystals were washed with 40 ml of t-butyl methyl ether to obtain 1.49 g of 4-hydroxy-3-[3-[3-chloro-4-(trifluoromethoxy)phenyl]-1- oxo-2-propenyl]-2H-1-benzopyran-2-one [Compound No. (1c-6)] was obtained as a yellow crystal.

$^1$H-NMR (270 MHz, CDCl$_3$) δ (ppm): 7.30-7.40 (3H), 7.63 (dd, 1H, J=2.2, 8.6 Hz), 7.72 (t, 1H, J=7.8 Hz), 7.81 (d, 1H, J=2.2 Hz), 7.91 (d, 1H, J=15.4 Hz), 8.10 (dd, 1H, J=1.6, 7.6 Hz), 8.41 (d, 1H, J=15.9 Hz), 18.64 (s, 1H)

Example 7

Synthesis of the Present Compound (IIa) [Compound No. (2a-17)]

In 4 ml of hexamethylphosphoramide was dissolved 0.33 g of 4-hydroxy-3-[3-[3-chloro-4-(trifluoromethoxy)phenyl]-1-oxo-2-propenyl]-6-methyl-2H-pyran-2-one, to this solution was added 50 mg of sodium hydride (60% oily), and the mixture was stirred at room temperature for 30 minutes. Then, 0.2 ml of dimethyl sulfate was added, and the mixture was stirred at 65° C. for 1 hour, and at room temperature overnight. Thereafter, the reaction mixture was added to ice water, and this was extracted with ethyl acetate. The organic layer was washed with an aqueous saturated sodium chloride solution, dried with anhydrous magnesium sulfate, and concentrated. The residue was subjected to silica gel column chromatography to obtain 0.13 g of 4-methoxy-3-[3-[3-chloro-4-(trifluoromethoxy)phenyl]-1-oxo-2-propenyl]-6-methyl-2H-pyran [Compound No. (2a-17)] as a pale yellow crystal.

$^1$H-NMR (270 MHz, CDCl$_3$) δ (ppm): 2.31 (s, 3H), 3.95 (s, 3H), 5.99 (s, 1H), 7.16 (d, 1H, J=15.9 Hz), 7.32 (d, 1H, J=7.6 Hz), 7.47 (d, 1H, J=6.5 Hz), 7.53 (d, 1H, J=15.9 Hz), 7.68 (d, 1H, J=1.9 Hz)

Example 8

Synthesis of the Present Compound (IIa) [Compound No. (2a-20)]

According to the same manner as that of Example 7 except that 0.35 g of 4-hydroxy-3-[3-[3-([1,3]dioxolan-2-yl)phenyl]-1-oxo-2-propenyl]-6-methyl-2H-pyran-2-one was used in place of 4-hydroxy-3-[3-[3-chloro-4-(trifluoromethoxy)phenyl]-1-oxo-2-propenyl]-6-methyl-2H-pyran-2-one, 0.18 g of 4-methoxy-3-[3-[3-([1,3]dioxolan-2-yl)phenyl]-1-oxo-2-propenyl]-6-methyl-2H-pyran-2-one [Compound No. (2a-20)] was obtained as a pale yellow oil.

$^1$H-NMR (400 MHz, CDCl$_3$) δ (ppm): 2.35 (s, 3H), 3.93 (s, 3H), 4.03-4.18 (m, 4H), 5.82 (s, 1H), 6.12 (s, 1H), 7.15 (d, 1H, J=16.0 Hz), 7.39 (t, 1H, J=7.7 Hz), 7.49 (d, 1H, J=7.6 Hz), 7.57 (d, 1H, J=7.6 Hz), 7.62 (d, 1H, J=16.0 Hz), 7.68 (s, 1H)

Example 9

Synthesis of the Present Compound (II-a) [Compound No. (2a-24)]

To a mixture of 0.81 g of 4-hydroxy-3-[3-(3-methylphenyl)-1-oxo-2-propenyl]-6-methyl-2H-pyran-2-one, 10 ml of tetrahydrofuran, 0.25 ml of 2-methoxyethanol, and 0.87 g of triphenylphosphine was added dropwise a solution of 0.57 g of diethyl azodicarboxylate in 6 ml of tetrahydrofuran, and this was stirred at room temperature overnight. The solvent was distilled off under reduced pressure, and the resulting residue was subjected to silica gel column chromatography to obtain 389 mg of 4-(2-methoxyethoxy)-3-[3-(3-methylphenyl)-1-oxo-2-propenyl]-6-methyl-2H-pyran-2-one [Compound No. (2a-24)] as a yellow oil.

$^1$H-NMR (400 MHz, CDCl$_3$) δ (ppm): 2.32 (s, 3H), 2.36 (s, 3H), 3.33 (s, 3H), 3.66 (t, 2H, J=4.6 Hz), 4.25 (t, 2H, J=4.6 Hz), 6.12 (s, 1H), 7.09 (d, 1H, J=15.9 Hz), 7.15-7.40 (4H), 7.56 (d, 1H, J=15.9 Hz)

Example 10

Synthesis of the Present Compound (IIa) [Compound No. (2a-25)]

According to the same manner as that of Example 9 except that 0.25 ml of methyl glycolate was used in place of 2-methoxyethanol, 470 mg of 4-methoxycarbonylmethoxy-3-[3-(3-methylphenyl)-1-oxo-2-propenyl]-6-methyl-2H-pyran-2-one [Compound No. (2a-25)] was obtained.

$^1$H-NMR (400 MHz, CDCl$_3$) δ (ppm): 2.30 (s, 3H), 2.35 (s, 3H), 3.79 (s, 3H), 4.75 (s, 2H), 5.95 (s, 1H), 7.06 (d, 1H, J=16.2 Hz), 7.20-7.80 (5H)

Example 11

Synthesis of the Present Compound (IIa) [Compound No. (2a-26)]

According to the same manner as that of Example 9 except that 0.34 ml of 3-acetyl-1-propanol was used in place of 2-methoxyethanol, 98 mg of 4-(3-acetylpropoxy)-3-[3-(3-methylphenyl)-1-oxo-2-propenyl]-6-methyl-2H-pyran-2-one [Compound No. (2a-26)] was obtained.

$^1$H-NMR (400 MHz, CDCl$_3$) δ (ppm): 1.95-2.05 (m, 2H), 2.07 (s, 3H), 2.33 (s, 3H), 2.36 (s, 3H), 2.61 (t, 2H, J=6.6 Hz), 4.15 (t, 2H, J=6.1 Hz), 6.12 (s, 1H), 7.09 (d, 1H, J=16.2 Hz), 7.15-7.40(4H), 7.54 (d, 1H, J=16.2 Hz)

Example 12

Synthesis of the Present Compound (IIa) [Compound No. (2a-27)]

According to the same manner as that of Example 9 except that 0.52 ml of ethylene glycol monoacetate was used in place of 2-methoxyethanol, 40 mg of 4-(2-hydroxyethoxy)-3-[3-(3-methylphenyl)-1-oxo-2-propenyl]-6-methyl-2H-pyran-2-one [Compound No. (2a-27)] was obtained.

$^1$H-NMR (400 MHz, CDCl$_3$) δ (ppm): 2.34 (s, 3H), 2.36 (s, 3H), 3.34 (t, 2H, J=6.4 Hz), 3.88-3.92 (m, 2H), 4.26 (t, 2H, J=4.6 Hz), 6.09 (s, 1H), 7.15-7.45 (m, 5H), 7.64 (d, 1H, J=16.1 Hz)

Example 13

Synthesis of the Present Compound (IIa) [Compound No. (2a-28)]

According to the same manner as that of Example 9 except that 0.32 ml of 2-(methylsulfonyl)ethanol was used in place of 2-methoxyethanol, 137 mg of 4-(2-methylsulfonylethoxy)-3-[3-(3-methylphenyl)-1-oxo-2-propenyl]-6-methyl-2H-pyran-2-one [Compound No. (2a-28)] was obtained.

$^1$H-NMR (400 MHz, CDCl$_3$) δ (ppm): 2.38 (s, 6H), 3.05 (s, 3H), 3.42 (t, 2H, J=5.6 Hz), 4.56 (t, 2H, J=5.2 Hz), 6.12 (s, 1H), 7.13 (d, 1H, J=16.1 Hz), 7.15-7.40 (4H), 7.55 (d, 1H, J=15.9 Hz)

Example 14

Synthesis of the Present Compound (IIc) [Compound No. (2c-17)]

In 15 ml of hexamethylphosphoramide was dissolved 1.37 g of 4-hydroxy-3-[3-[3-chloro-4-(trifluoromethoxy)phenyl] 1-oxo-2-propenyl]-2H-1-benzopyran-2-one, to this solution was added 0.17 g of sodium hydride (60% oily), and this was stirred at room temperature for 30 minutes. Then, 0.8 ml of dimethyl sulfate, and this was stirred at 65° C. for 2 hours. Thereafter, the reaction mixture was added to ice water, and this was extracted with ethyl acetate. The organic layer was washed with an aqueous saturated sodium chloride solution, dried with anhydrous magnesium sulfate, and concentrated. The residue was washed with t-butyl methyl ether to obtain 0.38 g of 4-methoxy-3-[3-[3-chloro-4-(trifluoromethoxy) phenyl]-1-oxo-2-propenyl]-2H-1-benzopyran-2-one [Compound No. (2c-17)] as a pale yellow crystal.

$^1$H-NMR (270 MHz, CDCl$_3$) δ (ppm): 3.97 (s, 3H), 7.16 (d, 1H, J=15.9 Hz), 7.30-7.40 (2H), 7.48-7.55 (1H), 7.54 (d, 1H, J=15.9 Hz), 7.55-7.65 (2H), 7.71 (d, 1H, J=1.9 Hz), 7.92 (dd, 1H, J=1.4, 7.8 Hz)

Example 15

Synthesis of the Present Compound (IIa') [Compound No. (3a-32)]

A mixture of 0.50 g of 3-acetyl-4-hydroxy-6-methyl-2 (1H)-pyridinone, 0.74 g of 3-chloro-4-(trifluoromethoxy) benzaldehyde, 6 mg of pyridine and 0.1 ml of piperidine was heated under refluxing for 4 hours. After cooled to room temperature, 40 ml of water was added to the reaction mixture, precipitated crystals were filtered, and this was washed with tetrahydrofuran, then with ethyl acetate to obtain 0.41 g of 4-hydroxy-3-[3-[3-chloro-4-(trifluoromethoxy)phenyl]-1-oxo-2-propenyl]-6-methyl-2(1H)-pyridinone [Compound No. (3a-32)] as a yellow crystal.

$^1$H-NMR (270 MHz, DMSO-d$_6$) δ (ppm): 2.22 (s, 3H), 5.90 (s, 1H), 7.60-7.70 (2H), 7.76 (d, 1H, J=16.2 Hz), 8.01 (s, 1H), 8.49 (d, 1H, J=15.9 Hz), 11.62 (s, 1H), 16.14 (s, 1H)

Example 16

Synthesis of the Present Compound (IIa') [Compound No. (3a-34)]

In a mixture of 2 ml of pyridine and 0.05 ml of piperidine were dissolved 0.23 g of 3-acetyl-4-hydroxy-1,6-dimethyl-2 (1H)-pyridinone and 0.23 g of 3-(methoxycarbonyl)benzaldehyde, and the solution was heated under refluxing for 2 hours. After cooled to room temperature, this was concentrated under reduced pressure, and the residue was subjected to silica gel column chromatography to obtain 0.06 g of 4-hydroxy-3-[3-[3-(methoxycarbonyl)phenyl]-1-oxo-2-propenyl]-1,6-dimethyl-2(1H)-pyridinone [Compound No. (3a-34)] as a yellow crystal.

$^1$H-NMR (270 MHz, DMSO-d$_6$) δ (ppm): 2.41 (s, 3H), 3.41 (s, 3H), 3.89 (s, 3H), 6.07 (s, 1H), 7.63 (t, 1H, J=7.8 Hz), 7.85 (d, 1H, J=15.8 Hz), 7.96-8.03 (m, 2H), 8.25 (s, 1H), 8.54 (d, 1H, J=15.8 Hz), 15.92 (broads, 1H)

Example 17

Synthesis of the Present Compound (IIa') [Compound No. (3a-37)]

To a solution of 2.93 g of 3-[N-(t-butoxycarbonyl)amino] benzaldehyde in 20 ml of dimethylformamide was added 0.58 g of sodium hydride (60% oily) under ice-cooling. After stirring at room temperature for 1 hour, a solution of 0.93 ml of 2-bromoethanol in 5 ml of dimethylformamide was added dropwise under ice-cooling. After stirring at room temperature for 14 hours, the mixture was heated to stir at 115° C. for 6 hours. Ethyl acetate was added, and this was washed successively with water and an aqueous saturated sedum chloride solution, dried with anhydrous sodium sulfate, and concentrated. The residue was subjected to silica gel column chromatography to obtain 0.75 g of oily 3-(2-oxo-oxazolidin-3-yl)benzaldehyde.

$^1$H-NMR (270 MHz, DMSO-d$_6$) δ (ppm): 4.10-4.16 (m, 2H), 4.44-4.51 (m, 2H), 7.61-7.71 (m, 2H), 7.86-7.91 (m, 1H), 8.10-8.12 (m, 1H), 10.03 (s, 1H)

According to the same manner as that of Example 16 except that 0.33 g of 3-acetyl-4-hydroxy-6-methyl-2(1H)-pyridinone was used in place of 3-acetyl-4-hydroxy-1,6-dimethyl-2(1H)-pyridinone, and 0.30 g of 3-(2-oxo-oxazolidin-3-yl)benzaldehyde was used in place of 3-(methoxycarbonyl) benzaldehyde, 0.22 g of 4-hydroxy-3-[3-[3-(2-oxo-oxazolidin-3-yl)phenyl]-1-oxo-2-propenyl]-6-methyl-2 (1H)-pyridinone [Compound No. (3a-37)] was obtained as a yellow crystal.

$^1$H-NMR (300 MHz, DMSO-d$_6$) δ (ppm): 2.21 (s, 3H), 4.11 (t, 2H, J=7.5 Hz), 4.47 (t, 2H, J=7.5 Hz), 5.89 (s, 1H), 7.38-7.53 (m, 2H), 7.65-7.69 (m, 1H), 7.81 (d, 1H, J=15.0 Hz), 7.89 (s, 1H), 8.53 (d, 1H, J=15.0 Hz), 11.57 (broads, 1H)

Example 18

Synthesis of the Present Compound (IIa') [Compound No. (3a-38)]

According to the same manner as that of Example 16 except that 0.42 g of 3-(2-oxo-oxazolidin-3-yl)benzaldehyde was used in place of 3-(methoxycarbonyl)benzaldehyde, 0.25 g of 4-hydroxy-3-[3-[3-(2-oxo-oxazolidin-3-yl)phenyl]-1-oxo-2-propenyl]-1,6-dimethyl-2(1H)-pyridinone [Compound No. (3a-38)] was obtained as a yellow crystal.

$^1$H-NMR (270 MHz, DMSO-d$_6$) δ (ppm): 2.41 (s, 3H), 3.40 (s, 3H), 4.09-4.15 (m, 2H), 4.44-4.50 (m, 2H), 6.06 (s, 1H), 7.48-7.53 (m, 2H), 7.65-7.69 (m, 1H), 7.80 (d, 1H, J=16.1 Hz), 7.89 (s, 1H), 8.50 (d, 1H, J=16.1 Hz), 16.03 (broads, 1H)

Example 19

Synthesis of the Present Compound (IIa') [Compound No. (3a-39)]

According to the same manner as that of Example 16 except that 1.09 g of 3-acetyl-4-hydroxy-6-methyl-2(1H)-pyridinone was used in place of 3-acetyl-4-hydroxy-1,6-dimethyl-2(1H)-pyridinone, and 1.68 g of 3-(2-morpholinoethoxy)benzaldehyde was used in place of 3-(methoxycarbonyl)benzaldehyde, 0.27 g of 4-hydroxy-3-[3-[3-(2-morpholinoethoxy)phenyl]-1-oxo-2-propenyl]-6-methyl-2(1H)-pyridinone [Compound No. (3a-39)] was obtained as a yellow crystal.

$^1$H-NMR (270 MHz, DMSO-d$_6$) δ (ppm): 2.21 (s, 3H), 2.47-2.50 (m, 4H), 2.71 (t, 2H, J=5.4 Hz), 3.58 (t, 4H, J=4.6 Hz), 4.14 (t, 2H, J=5.4 Hz), 5.88 (s, 1H), 7.05 (d, 1H, J=8.4 Hz), 7.24-7.41 (m, 3H), 7.77 (d, 1H, J=16.2 Hz), 8.50 (d, 1H, J=16.2 Hz), 11.56 (s, 1H), 16.42 (s, 1H)

Example 20

Synthesis of the Present Compound (IIa')
[Compound No. (3a-40)]

According to the same manner as that of Example 16 except that 4.87 g of 3-(2-morpholinoethoxy)benzaldehyde was used in place of 3-(methoxycarbonyl)benzaldehyde, 0.86 g of 4-hydroxy-3-[3-[3-(2-morpholinoethoxy)phenyl]-1-oxo-2-propenyl]-1,6-dimethyl-2(1H)-pyridinone [Compound No. (3a-40)] was obtained as a yellow crystal.

$^1$H-NMR (300 MHz, DMSO-$d_6$) δ (ppm): 2.38 (s, 3H), 2.41-2.50 (m, 4H), 2.71 (t, 2H, J=5.4 Hz), 3.32 (s, 3H), 3.57-3.60 (m, 4H), 4.14 (t, 2H, J=5.4 Hz), 6.06 (s, 1H), 7.03-7.07 (m, 1H), 7.25-7.54 (m, 3H), 7.77 (d, 1H, J=13.5 Hz), 8.46 (d, 1H, J=16.2 Hz)

Example 21

Synthesis of the Present Compound (IIc')
[Compound No. (3c-32)]

A mixture of 0.60 g of 3-acetyl-4-hydroxy-2(1H)-quinolinone, 1.99 g of 3-chloro-4-(trifluoromethoxy)benzaldehyde, 10 ml of pyridine and 88 μl of piperidine was heated under refluxing overnight. After cooling to room temperature, 50 ml of water was added to the reaction mixture, and precipitated crystals were filtered, and washed with 40 ml of tetrahydrofuran, and 60 ml of hexane to obtain 0.92 g of 4-hydroxy-3-[3-[3-chloro-4-(trifluoromethoxy)phenyl]-1-oxo-2-propenyl]-2(1H)-quinolinone [Compound No. (3c-32)] as a yellow crystal.

$^1$H-NMR (270 MHz, DMSO-$d_6$) δ (ppm): 7.26 (t, 1H, J=7.8 Hz), 7.32 (d, 1H, J=8.4 Hz), 7.65-7.75 (2H), 7.87 (d, 1H, J=8.4 Hz), 7.87 (d, 1H, J=17.0 Hz), 8.03 (d, 1H, J=7.8 Hz), 8.07 (s, 1H), 8.60 (d, 1H, J=15.9 Hz), 11.56 (s, 1H), 17.71 (s, 1H)

Example 22

Preparation of a Plasmid Having a Reporter Gene Linked to a Transcription Regulatory Region for a Type I Collagen Gene 1×10$^8$ cells of a normal human fetal skin fibroblast (Clontech, catalogue No. CC-2509) were cultured at 37° C. overnight under 5% CO$_2$ atmosphere. After the cultured cells were washed with a sodium phosphate buffer (hereinafter, referred to as PBS) twice, 3 ml of PBS was added thereto and the cells were scraped away the wall of a vessel using a cell scraper (Nalgen, catalogue No. 179693). The scraped cells were collected by centrifugation (1,500 rpm, 4° C., 15 min), and these were suspended in 20 ml of PBS and centrifuged again. To the resulting precipitates were added 11 ml of Solution 2 and 4.8 μl of pronase of DNA Extraction Kit (Stratagene, catalogue No. 200600). After shaken at 60° C. for 1 hour, the resulting mixture was allowed to stand in ice for 10 minutes. Then, 4 ml of Solution 3 of the kit was added to the mixture. After mixed, the mixture was allowed to stand in ice for 5 minutes and then centrifuged (3,000 rpm, 4° C., 15 min) to recover a supernatant. To the recovered supernatant was added 2 μl of RNase per 1 ml of the supernatant and the mixture was allowed to stand at 37° C. for 15 minutes. To the mixture was added 2-fold volume of ethanol. After mixed, a white thread-like substance (genomic DNA) appeared and the substance was recovered. The recovered genomic DNA was washed with 70% ethanol and then air-dried. The air-dried genomic DNA was dissolved in 500 μl of 10 mM Tris-HCl, 1 mM EDTA (pH 8.0) (hereinafter, referred to as TE).

The resulting genomic DNA solution (the amount equivalent to 1 μg of genomic DNA), each 1 μl (10 μmol/μl) of an oligonucleotide consisting of the nucleotide sequence represented by SEQ ID No:1 and an oligonucleotide consisting of the nucleotide sequence represented by SEQ ID No: 2, 29 μL of distilled water, 5 μl of the buffer attached to TaKaRa LA Taq (TAKARA SHUZO, catalogue No. RR002A), 5 μL of a Mg$^{2+}$ solution, 5 μL of a dNTP mixture and 0.5 μl of TaKaRa LA Taq (TAKARA SHUZO, catalogue No. RR002A) were mixed. After the resulting mixed solution was incubated at 94° C. for 5 minutes, the mixed solution was subjected to 30 cycles, in which one cycle consists of incubation at 94° C. for 1 minute, at 60° C. for 1 minute and then at 72° C. for 1 minute. The mixed solution was electrophoresed on a 2% agarose gel to recover about 0.5 kb of a DNA. The recovered DNA was treated with phenol/chloroform and then precipitated with ethanol to recover the DNA. The resulting DNA was dissolved in ultrapure water. To this solution were added 2.5 μl of NheI and 2.5 μl of HindIII, and then incubated at 37° C. for 3 hours. Then, the solution was electrophoresed on a 2% agarose gel to recover about 3.5 kb of a DNA. The recovered DNA was precipitated with ethanol to recover again the DNA (hereinafter, referred to as the collagen promoter DNA).

On the other hand, the vector pGL3 (Promega, catalogue No. E1751) having the nucleotide sequence encoding firefly luciferase was digested with NheI and HindIII, and then subjected to agarose gel electrophoresis as described above to recover about 5 kb of a DNA. The recovered DNA was precipitated with ethanol to recover the DNA again. To the recovered DNA were added 44 μl of distilled water, 5 μl of Buffer attached to Alkaline Phosphatase (TAKARA SHUZO, catalogue No. 2120A) and 1 μl of Alkaline Phosphatase (TAKARA SHUZO, catalogue No. 2120A). The mixed solution was incubated at 65° C. for 30 minutes. Then, the mixed solution was treated with phenol/chloroform twice, and precipitated with ethanol to recover the DNA (hereinafter referred to as the Luc vector DNA). Then, after about 20 ng of the collagen promoter DNA and about 20 ng of the Luc vector DNA were mixed, the same amount of a DNA Ligation kit Ver2 enzyme solution was added and this was incubated overnight at 16° C. To the mixed solution was added *Escherichia coli* 5Hdα (TOYOBO, catalogue No. DNA-903), this was allowed to stand in ice for 30 minutes, and then incubated at 42° C. for 45 seconds. The resulting *Escherichia coli* was seeded on a LB plate containing 50 μg/ml ampicillin sodium (Nacalai, catalogue No. 027-39), and this was allowed to stand at 37° C. for 1 day. A single colony appeared and the colony was cultured in 2 ml of a LB medium containing 50 μg/ml ampicillin at 37° C. for 12 hours. From the resulting culture solution, a plasmid DNA was prepared using AUTOMATIC DNA ISOLATION SYSTEM PI-50 (KURABO). The nucleotide sequence of the prepared plasmid DNA was analyzed with a DNA sequencer. As a result, it was confirmed that the plasmid (hereinafter, referred to as COL-Luc) had a nucleotide sequence comprising a nucleotide sequence encoding the amino acid sequence of firefly luciferase as a reporter gene linked downstream of the nucleotide sequence −3500 to +57 (the transcription initiation point is +1) of a transcription regulatory region for a human-derived Type I collagen α2 chain gene.

Example 23

Measurement of the Ability of a Test Compound to Regulate Transcription of a Type I Collagen Gene Using the Expression Level of a Report Gene as an Index $1 \times 10^6$ cells of a normal human fetal skin fibroblast were seeded on a 100 mm dish and cultured at 37° C. overnight under 5% $CO_2$ atmosphere in a Dulbecco's-MEM (Nissui Seiyaku, catalogue No. 05919) medium containing 10 (v/v) % heat-inactivated bovine fetal serum (hereinafter, referred to as FBS; Gibco, catalogue No. 21140-079) (hereinafter, this medium is referred to as D-MEM(+)). Then, the medium was replaced with a Dulbecco's-MEM medium not containing FBS (hereinafter, this medium is referred to as D-MEM(−)). To 300 μl of D-MEM(−) were added 5 μg of COL-Luc and 5 μg of pCMV-β-gal (Invitrogen, catalogue No. 10586-014), and the resulting mixed solution was allowed to stand at room temperature for 5 minutes (solution 1). To 300 μl of D-MEM (−) was added 20 μl of Lipofectine (Gibco, catalogue No. 18292-011), and the resulting mixed solution was allowed to stand at room temperature for 45 minutes (solution 2). Then, the solution 1 and the solution 2 were mixed. After the mixture was allowed to stand at room temperature for 10 minutes, 5.4 ml of D-MEM(−) was added to thereto, followed by mixing. The mixed solution was added to the normal human fetal skin fibroblasts, and the cells were cultured at 37° C. under 5% $CO_2$ atmosphere. After 6 hours, the culture supernatant was removed from the dish, and the cells were washed with PBS twice. To the dish was added 1 ml of PBS containing 0.25% trypsin, and the cells were scraped off the dish. To the scraped cells was added D-MEM(+), and these were mixed well. The mixture was dispensed into a 12-well plate at 1 ml per well, and the plate was incubated at 37° C. overnight under 5% $CO_2$ atmosphere. On the next day, each well was washed with D-MEM(−) twice, and this was replaced with 1 ml of a Dulbecco's-MEM medium containing 0.1% FBS (hereinafter, this medium is referred to as D-MEM (0.1%)).

To the thus cultured cells was added 10 μl of a 100 μM solution of the present compound represented by the compound number (2a-17), (2c-17), (3a-32) or (3c-32) in dimethyl sulfoxide (hereinafter, DMSO) (final concentration 1 μM). As a control, only 10 μl of DMSO was added.

After one hour, 10 μl of a 0.5 μg/ml aqueous solution of TGF-β (Pepro Tech) or distilled water was added to the well, and the plate was further incubated at 37° C. for 40 hours under 5% $CO_2$ atmosphere. After the incubated cells were washed with PBS twice, 200 μl of a cell lysing agent (Toyo Inc., catalogue No. PD10) was added thereto and the cells were scraped. The scraped cells were recovered as a cell suspension, and the suspension was centrifuged (15,000 rpm, 4° C., 5 min) to recover a supernatant. The recovered supernatant was transferred to a 96-well plate at 50 μl per well, and then 50 μl of a Luc assay solution (20 mM Tricine (pH 7.8), 2.67 mM $MgSO_4$, 0.1 mM EDTA, 33.3 mM DTT, 270 μM Coenzyme A, 530 μM ATP, 470 μM Luciferin) was automatically dispensed into the plate using MICROLUMAT LB96P (manufactured by EG&G BERTHOLD). Luminescence in each well was measured (Delay: 1.6 second, Meas. Interval: 20 second).

On the other hand, 50 μl of the recovered supernatant or the cell lysing agent was added to 50 μl of a β-gal substrate solution (5.8 mM o-nitrophenyl-beta-D-galactopyranoside, 1 mM $MgCl_2$, 45 mM 2-mercaptoethanol) which had been dispensed into a 96-well plate in advance, and the plate was incubated at 37° C. for 2 hours. Then, an absorbance in each well was measured using a microplate reader at 420 nm. Based on the resulting value, the transcription activity was calculated according to the following equation:

Transcription activity=[luminescence amount (supernatant-added section)−luminescence amount (cell lysing agent-added section)]/[420 nm absorbance (supernatant-added section)−420 nm absorbance (cell lysing agent-added section)]

Then, based on the calculated transcription activity, an inhibitory effect of a test compound on the ability of TGF-β to promote transcription of a Type I collagen gene was calculated as an inhibition percentage according to the following equation:

Inhibition percentage=[transcription activity (DMSO and TGF-β-added test section)−transcription activity (compound and TGF-β-added test section)]/[transcription activity (DMSO and TGF-β-added test section)−transcription activity (DMSO and TGF-β non-added test section)]×100

The inhibition percentages of the present compounds represented by the compound number (2a-17), (2c-17), (3a-32) and (3c-32) were 70 or more. It was found that these compounds can inhibit the ability of TGF-β to promote transcription of a Type I collagen gene, and then can suppress transcription of a Type I collagen gene.

Industrial Applicability

According to the present invention, it is possible to develop and provide a composition which decreases expression of a Type I collage gene in a tissue to induce a reduction in accumulation of collagen and thereby improves tissue fibrosis (i.e. a collagen accumulation-suppressing agent and a fibrosing disease-treating agent).

Sequence Listing Free Text

SEQ ID NO: 1
Oligonucleotide primer designed for amplifying a collagen promoter DNA SEQ ID NO: 2
Oligonucleotide primer designed for amplifying a collagen promoter DNA SEQ ID NO: 3
Oligonucleotide primer designed for detecting a collagen DNA SEQ ID NO: 4
Oligonucleotide primer designed for detecting a collagen DNA SEQ ID NO: 5
Oligonucleotide probe designed for detecting a collagen DNA

---

The invention claimed is:

1. A composition comprising a 2(1H)-pyridinone compound represented by the formula (XVIII):

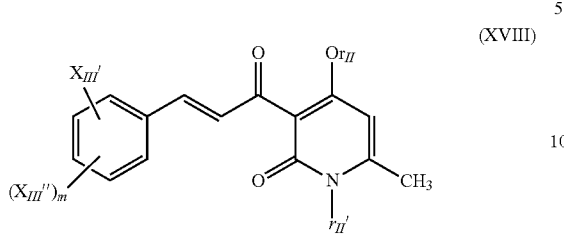

(XVIII)

wherein $X_{III}'$ represents a C2-C4 alkyl group, or a C1-C4 alkyl group substituted with a halogen atom or a C1-C4 alkoxy group, or a C2-C4 alkenyl group, or a C2-C4 alkenyl group, or a C2-C4 alkoxy group, or a $R_I$—S(O)$_l$-group (wherein $R_I$ represents a C1-C4 alkyl group, and l represents an integer of 0 to 2), or a cyano group, or a carboxy group, or a C1-C4 alkoxycarbonyl group, a $(R_{II})_2$N-group (wherein $R_{II}$ represents a C2-C4 alkyl group), or a $R_I$—CO—NH-group (wherein $R_I$ is as defined above), or a $R_I$O—CO—NH-group (wherein $R_I$ is as defined above), or a $R_I$NH—CO—NH-group (wherein $R_I$ is as defined above), or a $(R_I')_2$N—CO-group (wherein $R_I'$ represents a hydrogen atom or a C1-C4 alkyl group), or a RB-group (wherein B represents an oxygen atom or a sulfur atom, and R represents a C1-C4 alkyl group substituted with a halogen atom), $X_{III}''$ represents a hydrogen atom, a halogen atom, a C1-C4 alkyl group, or a C1-C4 alkoxy group, m represents 1 or 2, when m is 2, $X_{III}'''$s may be different, and $r_{II}$ and $r_{II}'$ are the same or different, and represent a hydrogen atom or a C1-C4 alkyl group; and an inert carrier.

2. A 2(1H)-pyridinone compound represented by the formula (XVIII):

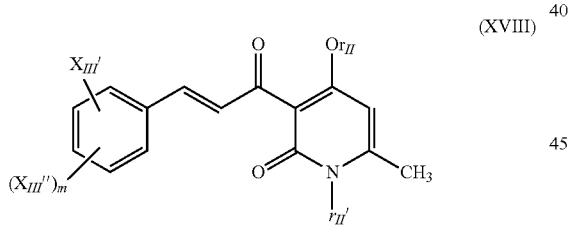

(XVIII)

wherein $X_{III}'$ represents a C2-C4 alkyl group, or a C1-C4 alkyl group substituted with a halogen atom or a C1-C4 alkoxy group, or a C2-C4 alkenyl group, or a C2-C4 alkynyl group, or a C2-C4 alkoxy group, or a $R_I$—S(O)$_l$-group (wherein $R_I$ represents a C1-C4 alkyl group, and l represents an integer of 0 to 2), or a cyano group, or a carboxy group, or a C1-C4 alkoxycarbonyl group, a $(R_{II})_2$N-group (wherein $R_{II}$ represents a C2-C4 alkyl group), or a $R_I$—CO—NH-group (wherein $R_I$ is as defined above), or a $R_I$O—CO—NH-group (wherein $R_I$ is as defined above), or a $R_I$NH—CO—NH-group (wherein $R_I$ is as defined above), or a $(R_I')_2$N—CO-group (wherein $R_I'$ represents a hydrogen atom or a C1-C4 alkyl group), or a RB-group (wherein B represents an oxygen atom or a sulfur atom, and R represents a C1-C4 alkyl group substituted with a halogen atom), $X_{III}''$ represents a hydrogen atom, a halogen atom, a C1-C4 alkyl group, or a C1-C4 alkoxy group, m represents 1 or 2, when m is 2, $X_{III}'''$s may be different, and $r_{II}$ and $r_{II}'$ are the same or different, and represent a hydrogen atom or a C1-C4 alkyl group.

3. A method for improving tissue fibrosis, which comprises administering an effective amount of the composition according to claim 1 to a mammal in need thereof.

4. A method for suppressing the activity of TGF-β, which comprises administering an effective amount of the composition according to claim 1 to a mammal in need thereof.

5. A method for suppressing transcription of a type I collagen gene, which comprises administering an effective amount of the composition according to claim 1 to a mammal in need thereof 6. A compound represented by the formula:

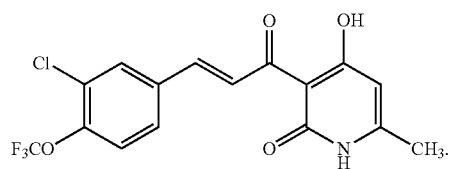 [SMILES: Cc1cc(O)c(C(=O)/C=C/c2ccc(OC(F)(F)F)c(Cl)c2)c(=O)[nH]1]

* * * * *

UNITED STATES PATENT AND TRADEMARK OFFICE
CERTIFICATE OF CORRECTION

| | | |
|---|---|---|
| PATENT NO. | : 8,524,729 B2 | Page 1 of 1 |
| APPLICATION NO. | : 10/572705 | |
| DATED | : September 3, 2013 | |
| INVENTOR(S) | : Tomigahara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2073 days.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 5

<210> SEQ ID NO 1
<211> LENGTH: 32
```

```
<212> TYPE: DNA
<213> ORGANISM: Artificial Sequence
<220> FEATURE:
<223> OTHER INFORMATION: Designed oligonucleotide primer to amplify
      collagen promoter DNA

<400> SEQUENCE: 1
ccaagctagc gaaattatct tttctttcat ag                                32

<210> SEQ ID NO 2
<211> LENGTH: 28
<212> TYPE: DNA
<213> ORGANISM: Artificial Sequence
<220> FEATURE:
<223> OTHER INFORMATION: Designed oligonucleotide primer to amplify
      collagen promoter DNA

<400> SEQUENCE: 2
ccaaaagctt gcagtcgtgg ccagtacc                                     28

<210> SEQ ID NO 3
<211> LENGTH: 19
<212> TYPE: DNA
<213> ORGANISM: Artificial Sequence
<220> FEATURE:
<223> OTHER INFORMATION: Designed oligonucleotide primer to detect
      collagen DNA

<400> SEQUENCE: 3
atggtggcag ccagtttga                                               19

<210> SEQ ID NO 4
<211> LENGTH: 22
<212> TYPE: DNA
<213> ORGANISM: Artificial Sequence
<220> FEATURE:
<223> OTHER INFORMATION: Designed oligonucleotide primer to detect
      collagen DNA

<400> SEQUENCE: 4
caggtacgca atgctgttct tg                                           22

<210> SEQ ID NO 5
<211> LENGTH: 23
<212> TYPE: DNA
<213> ORGANISM: Artificial Sequence
<220> FEATURE:
<223> OTHER INFORMATION: Designed oligonucleotide probe to detect
      collagen DNA

<400> SEQUENCE: 5
ctcgccttca tgcgcctgct agc                                          23
```